(12) United States Patent
Alleyne et al.

(10) Patent No.: US 12,102,367 B2
(45) Date of Patent: Oct. 1, 2024

(54) METHOD, COMPOSITION, AND APPARATUS FOR STABILIZATION OF VERTEBRAL BODIES

(71) Applicant: Osteoagra LLC, La Jolla, CA (US)

(72) Inventors: Neville Alleyne, La Jolla, CA (US); Jeffrey C. Fernyhough, Boca Raton, FL (US); Clark H. Hutton, La Jolla, CA (US)

(73) Assignee: Osteoagra LLC, La Jolla, CA (US)

( * ) Notice: Subject to any disclaimer, the term of this patent is extended or adjusted under 35 U.S.C. 154(b) by 1071 days.

(21) Appl. No.: 16/708,373

(22) Filed: Dec. 9, 2019

(65) Prior Publication Data
US 2020/0146737 A1    May 14, 2020

Related U.S. Application Data

(60) Continuation-in-part of application No. 16/600,976, filed on Oct. 14, 2019, which is a division of
(Continued)

(51) Int. Cl.
*A61B 17/88*       (2006.01)
*A61F 2/28*        (2006.01)
(Continued)

(52) U.S. Cl.
CPC ........ *A61B 17/8855* (2013.01); *A61F 2/2846* (2013.01); *A61F 2/4601* (2013.01);
(Continued)

(58) Field of Classification Search
CPC ............ A61B 17/8825; A61B 17/8816; A61B 17/8805; A61F 2002/2839; A61F 2/4601; A61M 2005/004; A61M 2005/005
See application file for complete search history.

(56) References Cited

U.S. PATENT DOCUMENTS 4,462,394 A     7/1984    Jacobs
5,472,445 A     12/1995   Yakimicki et al.
(Continued)

FOREIGN PATENT DOCUMENTS

WO    2018232100 A1    12/2018

OTHER PUBLICATIONS

U.S. Appl. No. 16/600,976, filed Oct. 14, 2019, Neville Alleyne M.D.
(Continued)

*Primary Examiner* — David W Bates
(74) *Attorney, Agent, or Firm* — Veros Legal Solutions, LLP

(57) ABSTRACT

A method for stabilizing a vertebral body is provided. The method includes creating one or more openings into a central region of the vertebral body and dispose at least one cannula in the one or more openings. The method includes forming an internal cavity within the vertebral body through at least one of the one or more openings. The method includes injecting bone particles into the internal cavity of the vertebral body through a bone particle catheter disposed within the at least one cannula. The method includes applying pressure to the bone particles within the internal cavity of the vertebral body, thereby compressing them against a sidewall of the internal cavity. The method includes removing the at least one cannula and closing the one or more openings, thereby sealing the bone particles within the internal cavity of the vertebral body. A system for stabilizing a vertebral body is also provided.

11 Claims, 42 Drawing Sheets

Related U.S. Application Data application No. 16/016,635, filed on Jun. 24, 2018, now Pat. No. 10,441,336, which is a continuation-in-part of application No. PCT/US2018/037509, filed on Jun. 14, 2018.

(60) Provisional application No. 62/519,409, filed on Jun. 14, 2017, provisional application No. 62/782,290, filed on Dec. 19, 2018, provisional application No. 62/777,647, filed on Dec. 10, 2018.

(51) Int. Cl.
*A61F 2/46* (2006.01)
*A61B 17/56* (2006.01)

(52) U.S. Cl.
CPC ....... *A61F 2/4611* (2013.01); *A61B 2017/564* (2013.01); *A61B 2217/005* (2013.01); *A61F 2002/2835* (2013.01); *A61F 2310/00359* (2013.01)

(56) References Cited

U.S. PATENT DOCUMENTS

| | | | |
|---|---|---|---|
| 5,702,454 A * | 12/1997 | Baumgartner | A61F 2/4611 623/908 |
| 5,814,084 A * | 9/1998 | Grivas | A61B 17/1635 623/23.48 |
| 5,849,014 A | 12/1998 | Mastrorio et al. | |
| 5,989,256 A | 11/1999 | Kuslich et al. | |
| 5,997,580 A | 12/1999 | Mastrorio et al. | |
| 6,056,749 A | 5/2000 | Kuslich | |
| 6,217,581 B1 * | 4/2001 | Tolson | B27G 11/00 606/86 R |
| 6,248,110 B1 * | 6/2001 | Reiley | A61B 17/8805 606/92 |
| RE37,479 E | 12/2001 | Kuslich | |
| 6,383,188 B2 | 5/2002 | Kuslich et al. | |
| D464,135 S * | 10/2002 | Hawkins | D24/155 |
| 6,575,978 B2 | 6/2003 | Peterson et al. | |
| 6,620,162 B2 | 9/2003 | Kuslich et al. | |
| 6,656,185 B2 | 12/2003 | Gleason et al. | |
| 6,695,852 B2 | 2/2004 | Gleason | |
| 6,706,044 B2 | 3/2004 | Kuslich et al. | |
| 6,712,853 B2 | 3/2004 | Kuslich | |
| 7,056,345 B2 | 6/2006 | Kuslich | |
| 7,220,282 B2 | 5/2007 | Kuslich | |
| 7,226,481 B2 * | 6/2007 | Kuslich | A61B 17/7098 623/17.11 |
| 7,351,262 B2 * | 4/2008 | Bindseil | A61F 2/4455 623/17.11 |
| 7,803,188 B2 * | 9/2010 | Justis | A61B 17/7095 623/17.11 |
| 7,931,689 B2 * | 4/2011 | Hochschuler | A61B 17/7097 623/17.12 |
| 7,959,683 B2 | 6/2011 | Semler et al. | |
| RE42,757 E | 9/2011 | Kuslich et al. | |
| 8,012,211 B2 | 9/2011 | Kuslich | |
| 8,034,109 B2 * | 10/2011 | Zwirkoski | A61F 2/442 606/86 R |
| 8,110,212 B2 | 2/2012 | Marcolongo et al. | |
| 8,690,883 B2 * | 4/2014 | Collins | A61F 2/4611 604/165.01 |
| 8,747,475 B2 | 6/2014 | Kuslich | |
| 8,906,094 B2 | 12/2014 | Roche et al. | |
| 9,078,884 B2 | 7/2015 | Lally | |
| 9,179,959 B2 | 11/2015 | Rabiner et al. | |
| 9,387,088 B2 | 7/2016 | Roche et al. | |
| 9,387,277 B2 | 7/2016 | Buckland et al. | |
| 9,526,621 B2 | 12/2016 | Kuslich | |
| 9,550,010 B2 | 1/2017 | Schulz et al. | |
| 9,833,332 B2 | 12/2017 | Neubardt | |
| 9,844,444 B2 | 12/2017 | Wolfe et al. | |
| 9,913,725 B2 | 3/2018 | Roche et al. | |
| 9,925,058 B2 | 3/2018 | Wolfe et al. | |
| 10,376,648 B1 * | 8/2019 | Hensler | A61B 17/8811 |
| 10,441,336 B2 | 10/2019 | Alleyne | |
| 10,478,522 B2 | 11/2019 | Francaviglia et al. | |
| 11,013,609 B2 | 5/2021 | Srour et al. | |
| 2002/0147496 A1 * | 10/2002 | Belef | A61F 2/02 623/17.12 |
| 2004/0138703 A1 | 7/2004 | Alleyne | |
| 2005/0278023 A1 * | 12/2005 | Zwirkoski | A61B 17/8635 623/11.11 |
| 2006/0100706 A1 | 5/2006 | Shadduck et al. | |
| 2006/0122621 A1 | 6/2006 | Truckai et al. | |
| 2006/0149268 A1 | 7/2006 | Truckai et al. | |
| 2006/0229625 A1 | 10/2006 | Truckai et al. | |
| 2006/0265077 A1 * | 11/2006 | Zwirkoski | A61F 2/442 623/17.14 |
| 2007/0093846 A1 | 4/2007 | Frigg et al. | |
| 2007/0162132 A1 * | 7/2007 | Messerli | A61F 2/447 623/17.11 |
| 2007/0185496 A1 | 8/2007 | Beckman et al. | |
| 2007/0233146 A1 * | 10/2007 | Henniges | A61B 17/8816 606/91 |
| 2008/0033572 A1 | 2/2008 | D'Antonio et al. | |
| 2008/0188945 A1 | 8/2008 | Boyce et al. | |
| 2008/0249481 A1 * | 10/2008 | Crainich | A61B 17/8805 606/80 |
| 2009/0098092 A1 | 4/2009 | Meredith | |
| 2009/0176193 A1 * | 7/2009 | Kaigler, Sr. | A61C 8/0006 433/199.1 |
| 2009/0299282 A1 * | 12/2009 | Lau | A61M 29/02 604/99.01 |
| 2010/0076445 A1 | 3/2010 | Pagano | |
| 2010/0198140 A1 * | 8/2010 | Lawson | A61B 17/7095 604/264 |
| 2011/0112588 A1 | 5/2011 | Linderman et al. | |
| 2011/0245866 A1 * | 10/2011 | Cassingham | A61B 17/00491 606/213 |
| 2012/0116515 A1 | 5/2012 | Semler et al. | |
| 2012/0245703 A1 | 9/2012 | Meredith | |
| 2012/0265209 A1 | 10/2012 | Druma et al. | |
| 2013/0012951 A1 | 1/2013 | Linderman | |
| 2014/0257483 A1 | 9/2014 | Swann | |
| 2018/0000595 A1 * | 1/2018 | Carter | A61L 27/3608 |

OTHER PUBLICATIONS

U.S. Appl. No. 62/782290, filed Dec. 19, 2018, Neville Alleyne M.D.

He, et al. (2015). Bone cements for percutaneous vertebroplasty and balloon kyphoplasty: Current status and future developments. Journal of Orthopaedic Translation. 3. 10.1016/j.jot.2014.11.002.

International Search Report and Written Opinion mailed Sep. 7, 2018 in International Patent Application No. PCT/US2018/037509.

Wang, et al. Clinical measurement of intravertebral pressure during vertebroplasty and kyphoplasty. Pain Physician. Jul.-Aug. 2013;16(4):E411-8. ISSN 2150-1149.

* cited by examiner

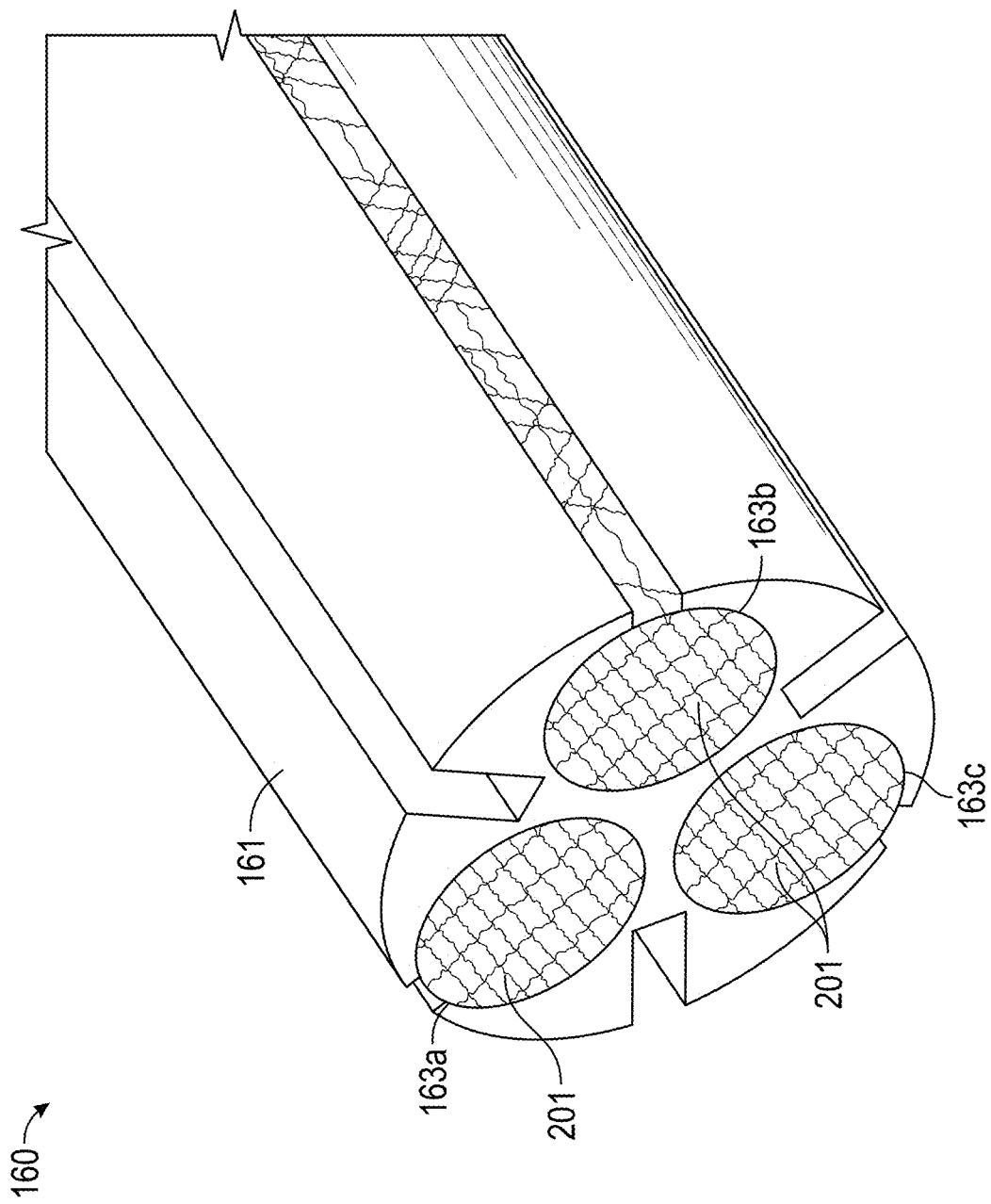

METHOD, COMPOSITION, AND APPARATUS FOR STABILIZATION OF VERTEBRAL BODIES

CROSS-REFERENCE TO RELATED APPLICATIONS

This application is a continuation of U.S. patent application Ser. No. 16/600,976 filed Oct. 14, 2019, which is a divisional of U.S. application Ser. No. 16/016,635 filed Jun. 24, 2018, which is a continuation-in-part of International Application No. PCT/US2018/037509 filed Jun. 14, which claims the benefit under 35 U.S.C. § 119(e) of U.S. Provisional Application No. 62/519,409 filed Jun. 14, 2017. This application also claims priority to U.S. Provisional Application No. 62/777,647, filed on Dec. 10, 2018, and U.S. Provisional Application No. 62/782,290, filed on Dec. 19, 2018. The entire contents of all of the above applications are hereby incorporated by reference.

BACKGROUND

Osteoporosis has continued to be a ubiquitous problem, especially in the elderly population. It is said that osteoporosis sufferers outnumber patients in the United States who have had MI's, stroke, and breast cancer combined. Osteoporosis can result in compression fractures of the vertebral bodies of the spinal column. As shown in FIG. 1, these fractures 10 generally occur in the anterior portion of the vertebra, with this portion compressing to a smaller height than a normal vertebral body. With increasing numbers of osteoporotic compression fractures of the thoracic and lumbar spine, it is felt that 1 in 3 women and 1 in 5 men will have an osteoporotic fracture in their lifetime. By 2020, osteoporosis is expected to affect approximately 14 million people in the United States. These fractures become more common obviously in older population and current treatment recommendations include vertebroplasty which can be done as an outpatient and kyphoplasty, which requires an in hospital stay of approximately one day.

PMMA, poly methacrylate, is the substance used in both vertebroplasty and kyphoplasty. This material has been used throughout orthopedics for over 35 years. The first total hip replacements done by Dr. Charnley in Boston utilized a methacrylate. This material is also known as bone cement and its modulus of elasticity is much higher than that of cancellous or cortical bone. When this material is placed into a vertebral body and is allowed to cure, it creates an exothermic reaction, which can sometimes deaden or destroy nociceptin fibers and once it is hardened, it provides rigid support of the vertebra. Unfortunately, the remaining part of the vertebra and the part in which the cement has been placed cannot grow new bone. The exothermic reaction, if it is close to the endplate, can cause avascular necrosis and result in endplate fracture and adjacent segment collapse. Some of the issues that are associated with the use of PMMA include, but are not limited to, cord compression from ectopic cement extending from the vertebral body into the spinal canal, extrusion of cement through the cartilaginous endplate into the disc, allergic reaction to PMMA, coagulopathy, PMMA getting into the basivertebral sinus resulting in pulmonary emboli and infection because of the foreign body. These are some of the related complications that can occur with vertebroplasty or kyphoplasty. Furthermore, what we have seen over the years is that the cement, which does decrease pain, also appears to cause adjacent segment fractures at a later date. Some as early as a few months and others within a few years. The reason for these compression fractures is: 1) underlying osteoporosis throughout the vertebral bodies. 2) cement having a higher density than the cortical or cancellous bone and adjacent microfracturing, which may not have been detected at the time of the initial procedure involving the adjacent vertebra. In addition, compression fractures at T5 or above are technically difficult due to the small pedicle and the parallel orientation of these pedicles. The thoracic spine is also very vulnerable in the event the cement is extruded, which could result in myelopathy or paresis or plegia.

It should be noted that this Background is not intended to be an aid in determining the scope of the claimed subject matter nor be viewed as limiting the claimed subject matter to implementations that solve any or all of the disadvantages or problems presented above. The discussion of any technology, documents, or references in this Background section should not be interpreted as an admission that the material described is prior art to any of the subject matter claimed herein.

SUMMARY

It is understood that various configurations of the subject technology will become apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

According to some embodiments, a method for stabilizing a vertebral body is provided. The method includes creating one or more openings into a central region of the vertebral body and dispose at least one cannula in the one or more openings. The method includes forming an internal cavity within the vertebral body through at least one of the one or more openings. The method includes injecting bone particles into the internal cavity of the vertebral body through a bone particle catheter disposed within the at least one cannula. The method includes applying pressure to the bone particles within the internal cavity of the vertebral body, thereby compressing them against a sidewall of the internal cavity. The method includes removing the at least one cannula and closing the one or more openings, thereby sealing the bone particles within the internal cavity of the vertebral body.

According to some other embodiments, a system for stabilizing a vertebral body is provided. The system includes at least one cannula configured to be disposed at least partially into a central region of the vertebral body through an opening in the vertebral body. The system includes at least one catheter configured to be disposed at least partially into the central region of the vertebral body through the at least one cannula. The system includes a bone particle dispenser. The bone particle dispenser includes at least one of a bone particle reservoir or a bone particle cartridge comprising at least one barrel configured to hold bone particles. The bone particle dispenser includes at least one plunger configured to push bone particles from the at least one of the bone particle reservoir or from the at least one barrel of the bone particle cartridge through the at least one catheter into an internal cavity in the central region of the vertebral body.

BRIEF DESCRIPTION OF THE DRAWINGS

Various embodiments are discussed in detail in conjunction with the Figures described below, with an emphasis on highlighting the advantageous features. These embodiments are for illustrative purposes only and any scale that may be illustrated therein does not limit the scope of the technology disclosed. These drawings include the following figures, in which like numerals indicate like parts.

FIG. 23 illustrates a magnified portion of the cartridge of FIG. 22 showing the bone particles disposed in the barrels, in accordance with some embodiments;

DETAILED DESCRIPTION

Figure 1:
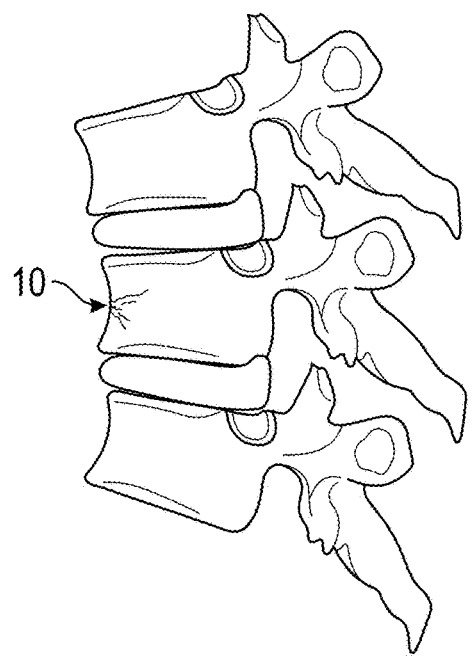
FIG. 1 illustrates a vertebral body with a compression fracture.

The following description and examples illustrate some exemplary implementations, embodiments, and arrangements of the disclosed invention in detail. Those of skill in the art will recognize that there are numerous variations and modifications of this invention that are encompassed by its scope. Accordingly, the description of a certain example embodiment should not be deemed to limit the scope of the present invention.

General Considerations

In order to be successful in stabilizing these fractures, bone should be inserted, rather than a foreign body like PMMA. By inserting cortical allograft or autologous bone particles, we are able to gradually, steadily, increase the bone density within the vertebral body and allow the body to perform its normal healing by not destroying the bone matrix within the vertebral body. PMMA, when it is allowed to cure, creates an exothermic reaction, which then destroys the bone and does not allow new bone to incorporate into it. In contrast, allograft or autologous bone will allow the natural healing processes of bone to not only stabilize the fracture, but to heal the fracture with new bone. The vertebral bodies receive their blood supply from surrounding tissues and the lumbar spine, lumbar vertebral arteries, the segmental arteries, come off the aorta and supply the blood to the vertebral body to allow it to heal. When PMMA is introduced into a compressed vertebra it does help to stabilize that vertebra, but in the end, there is no healing that occurs and if the PMMA is very close to the cartilaginous endplate, it may create fractures due to migration of the PMMA or the heat may create osteonecrosis which will then lead to fracturing of the endplate and adjacent segment collapse.

In addition, on complex deformity, correction, in which thoracolumbar or thoracolumbar sacral or thoracolumbar sacroiliac fixation is utilized. The cephalad vertebra can also undergo collapse, kyphosis and fracture. On these long constructs, orthopedic and neurosurgeons have angled the most cephalad screws in a more angled trajectory pointing down at the inferior endplate of the top vertebral body. This angulation of screw is to minimize the forces at the apex and minimize the cut out of these pedicle screws in this very fragile osteoporotic bone for surgical procedures that are directed to complex deformity correction. In addition, some surgeons have extended bone graft above the level of the top screw to minimize fracturing or proximal junctional kyphosis. However, none of these are foolproof because of the diffuse osteopenia or osteoporosis in all of the vertebral bodies. It is therefore contemplated that stabilization above the level of a long construct may prove to be beneficial by inserting PMMA, polymethylmethacrylate, either as a vertebroplasty augmentation or kyphoplasty augmentation. It is our thought process that PMMA will not allow that fracture to heal or that vertebral body to heal. It is purely for stability. Therefore, it is much more prudent to insert autologous or allograft bone into the vertebral body to minimize proximal junctional kyphosis. In addition, this bone graft material can be inserted into the sacrum in order to help increase the bone density in the sacrum or into the ilium or any other bone. Osteoporosis can occur in any bone in the human body. There are 206 bones in the adult of which bones in the foot and ankle are susceptible to fracture and complex open reduction internal fixation is required with bone graft and sometimes methacrylate. In those cases, instead of methacrylate, bone particles can be used to strengthen the fracture.

Most thoracic and lumbar burst fractures are not treated and, as a matter of fact, is contraindicated for vertebroplasty or kyphoplasty. However, in stable burst fractures inserting allograft or autologous bone under pressure can be done safely to stabilize burst fractures and minimize the need for surgery. Unstable burst fractures with bone fragments in the canal may still be a contraindication even for bone particle insertion; however, once the stability has been achieved, the adjacent segments to the fracture, if osteoporotic, can be augmented with particles of bone whether it be autologous or allograft.

Given the 700,000 to 800,000 vertebral compression fractures that occur each year, the estimated cost for their treatment is anywhere from 13-21 billion dollars per year. The ability to treat these in an effort to allow the natural processes of healing to occur within the vertebral body will allow the vertebral body itself to fill in with bone. Given the blood supply and the compression that exist by placing these particles pressurized through the interstices of the cancellous marrow of the said vertebra, the vertebra may gradually increase its vertebral height and its vertebral bone density. In addition, the vertebral body can be expanded by gradual, steady pressure and be seen under visualization by fluoroscopy, x-ray, CT, ultrasound, MRI. In addition, the particles can, but need not necessarily, be impregnated with a barium compound such as ISOVUE which will allow the vertebral body to be well visualized when the particles are being injected into the vertebra. Moreover, the use of ultrasound to show improved bone density can be performed to look at pre- and post-procedure bone density and vertebral height. With some of the kyphoplasties, early and/or late collapse of the vertebra can occur due to loss of the distraction by the cement or adjacent fracturing of the superior and inferior endplate of said vertebra. With the installation of bone particles, autologous or allograft, vertebral body height and density may be maintained since bone will attempt to heal within the interstices of the particles.

The present intervention comprises a method and apparatus for spinal stabilization of weak or fractured vertebral bodies or any bone with autologous or allograft bone particles via a novel injection apparatus that may further be capable of measuring pressure and density of the vertebral body. The particles can come in a plurality of geometric shapes that can vary in size or be uniform. The diameter of these microspheres can vary from one micron to 1000 microns diameter, with about 100-200 microns diameter being one specific example size range. In addition, these microspheres can be embedded with barium to allow for better visualization and can vary in the diameter depending on the degree of osteoporosis or collapse. Utilizing bone particle augmentation we will be able to deliver significant enough bone material to stabilize the fracture and also increase some of the vertebral height, if not all, as well as allowing the fracture to heal with bone and not allowing the fracture to remain unhealed because of a foreign material, poly methacrylate, in the center or within the vertebral body, which would inhibit in healing.

Example Systems and Methods—Bone Slurry Injection

Figure 2:
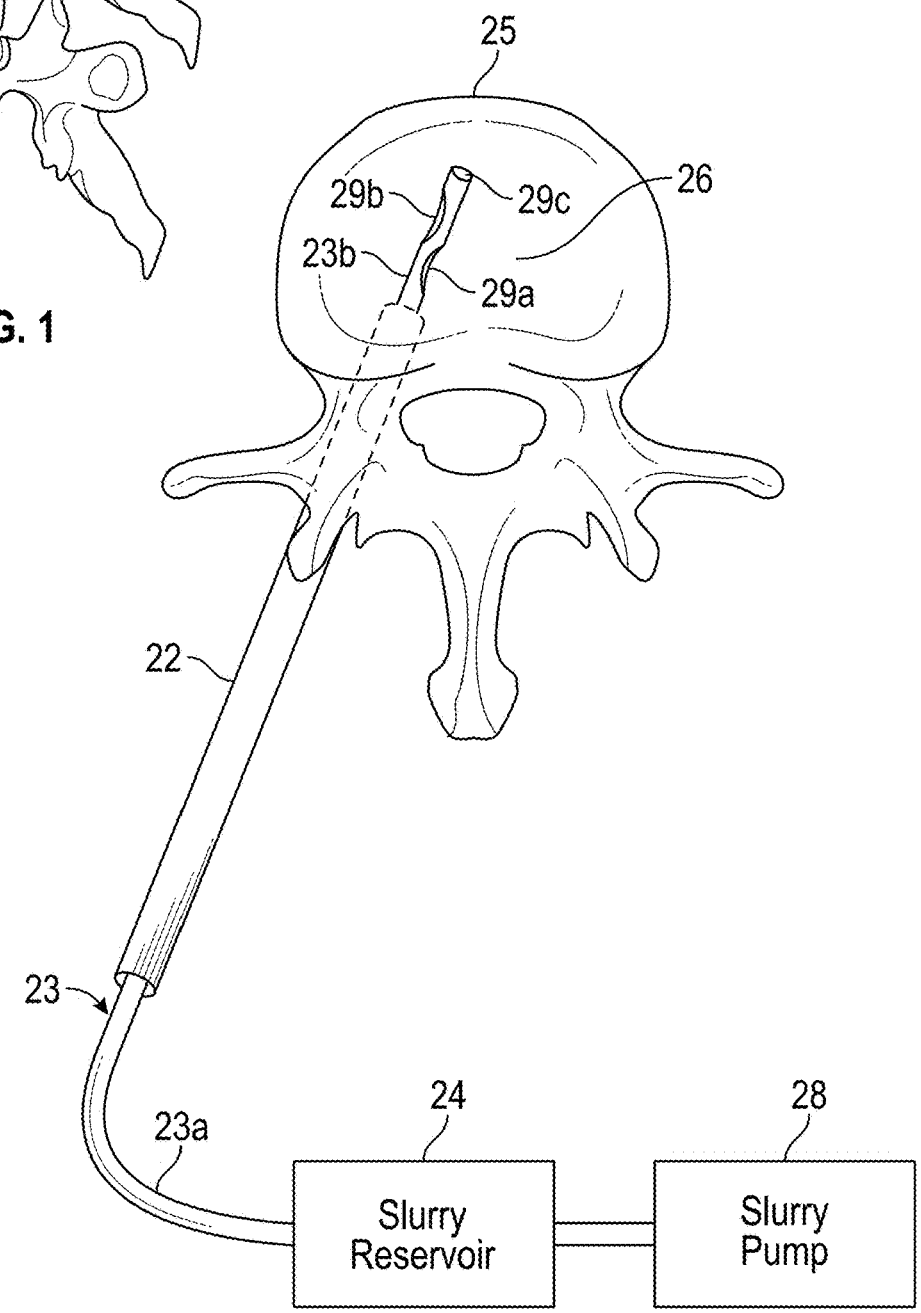
FIG. 2 is a schematic block diagram of one implementation of a system in accordance with some example embodiments.
Figure 3:
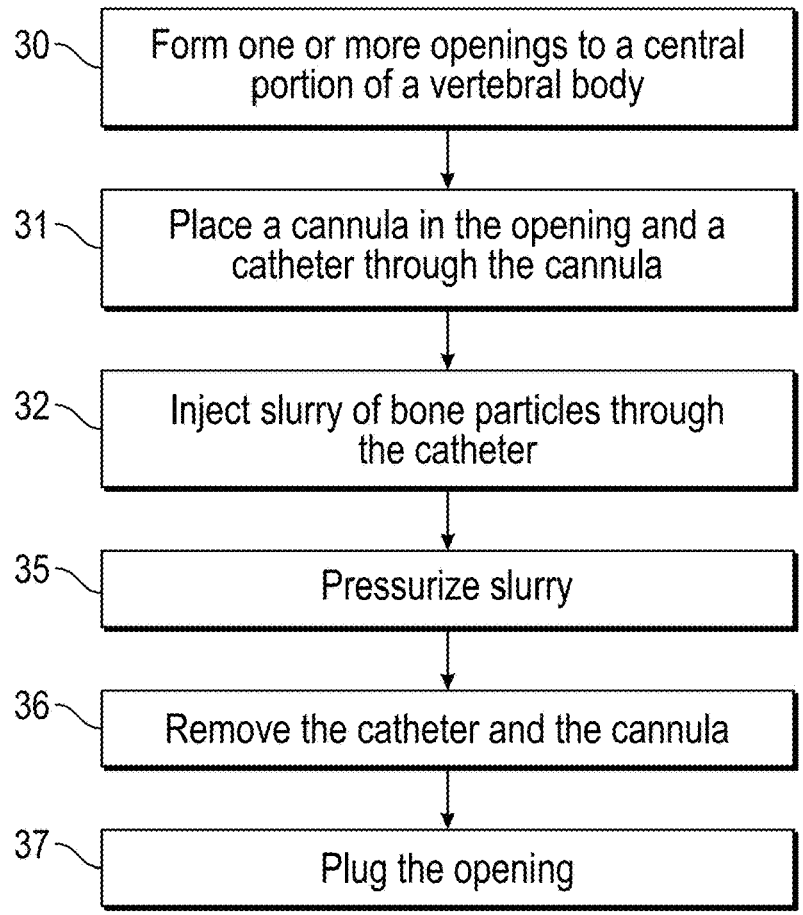
FIG. 3 is a block diagram of a method that may be performed with any system described herein, in accordance with some embodiments.

Referring now to FIGS. 2 and 3, one exemplary apparatus and method of vertebral body stabilization will be described. The system of FIG. 2 includes a cannula 22 and a catheter 23 having a proximal end 23a and a distal end 23b. The cannula 22 is configured for accessing the interior portion of a human vertebral body. The cannula 22 may have an inner diameter in the range of 2.5 to 5 mm, 8 or 10-gauge rigid tubing for example, which is in the range used in conventional vertebroplasty and kyphoplasty procedures. FIG. 2 shows the cannula 22 installed through a transpedicular opening into the interior portion 26 of a vertebral body 25. This is a common location for cannula insertion in currently performed vertebroplasty and kyphoplasty procedures, although a more lateral approach is sometimes utilized. It is also conceived that such a cannula can be inserted through the cartilaginous endplate into the vertebral body.

The catheter 23 is configured to be inserted into the central portion 26 of the vertebral body 25 through the cannula 22 and FIG. 2 illustrates the catheter 23 so positioned. The term catheter as used herein means any form of tube, rigid or flexible, made of any suitable material, whether polymer or metal or both. The catheter may have an inner diameter in the range of 1.5 to 3 mm. At least the distal portion may be formed as a 12, 13, or 14-gauge metal needle for example. The distal end 23b of the catheter 23 includes one or more openings 29a, 29b, 29c. One or more of these openings, such as opening 29a and 29b may be in the side of the catheter to inject material substantially perpendicular to the longitudinal extend of the catheter. An opening 29c may also be provided in the distal tip to inject material parallel with the longitudinal axis of the catheter.

The system of FIG. 2 also includes a slurry reservoir 24. The slurry reservoir 24 contains a slurry of bone particles to be implanted into the inner portion 26 of the vertebral body. A slurry pump 28 may be coupled to the slurry reservoir 24 and catheter 23 to force at least some of the slurry of bone particles down the catheter and into the interior portion 26 of the vertebral body 25. In use, the components of FIG. 2 including the cannula 22, catheter 23, slurry of bone particles 24 and slurry pump 28 may be provided to a physician as part or all of a surgical kit. In such a kit, the slurry reservoir could be made part of the catheter 23 or the slurry pump 28 and be pre-filled with a slurry of bone particles. The volume needed for such a reservoir is the volume of slurry that contains about 5 cc volume of bone particles.

FIG. 3 is a block diagram of a surgical method that can be performed with at least the apparatus of FIG. 2. At block 30, one or more openings to a central region of a vertebral body are created. This can be done by the same methods that are used in conventional arthroplasty and kyphoplasty procedures such as with a stylet or trocar and/or a bone drill. At block 31, this procedure will leave a cannula behind extending through the opening as shown, for example, in FIG. 2. Also at block 31, a catheter is positioned inside the vertebral body through the cannula. At block 32, a slurry of bone particles is injected into the vertebral body through the catheter. At block 35, the slurry is pressurized. This may occur in conjunction with the injecting of block 32. Pressurizing the slurry can increase the height of the vertebral body as slurry is injected. It is advantageous if this is performed without a bag or other structure enclosing or confining the slurry that is being injected. This can allow direct contact and healing between the implanted bone particles and the bone tissue inside the fractured and/or weakened vertebral body in, for example, a spinal compression fracture, while additionally providing immediate stabilization resulting from the compressed bone particles interlocked in a 'granular mechanic' structure of packed granules resisting further compression or movement and enclosed by the spinal bony fracture fragments and the remainder of the outer shell of the vertebral body.

It is beneficial to monitor the slurry injection under fluoroscopy to visualize the increased density in the vertebral body interior as well as the expansion of the endplates. This may be done without a contrast medium as the accumulation of the denser cortical bone will be visible under fluoroscopy. As explained further below, it is also possible to incorporate a radiopaque contrast medium to the slurry to enhance this visualization.

At the conclusion of the injection, the bone particles will support the vertebral body in its expanded state. Advantageously, this support function can be essentially immediate, similar to a conventional kyphoplasty where the PMMA curing process takes a few hours or even less. After injecting the slurry, the catheter and cannula are removed at block 36. If desired, as shown in block 37, a plug may be placed in the opening that the cannula entered the vertebral body through. Such a plug can be made of a variety of materials including, but not limited to, stainless steel, titanium, cobalt chrome molybdenum, TLA, PGA, PMMA, methylcellulose, or cortical allograft bone.

It may be noted here that the procedure may optionally include the insertion of an inflatable balloon bone tamp prior to injecting slurry. The use of such a bone tamp to create a cavity inside the vertebral body is a familiar part of conventional kyphoplasty procedures.

The slurry of bone particles can take a variety of forms. As used herein, the term "slurry" refers to a flowable mixture of solid particles in a liquid carrier. With respect to material content, one suitable slurry composition is bone particles suspended in pure water or saline without any functionally significant additional substances. The slurry may contain 20% to 85% bone by volume. At the lower end of this range, extrusion is more like that of the liquid carrier, and the particles may not interact appreciably in the catheter as the slurry is injected. At the higher end, there will be significant particle to particle contact when the slurry is forced through the catheter. This requires more force to extrude from the catheter, but the material being delivered is closer to its final compacted post-injection form. In some implementations, the slurry may be 40% to 60% bone by volume. Although saline alone can be advantageous, other carriers and/or supplemental substances can be included in some implementations such as blood, platelets, contrast agent, stem cells, and growth factor. Hyaluronic acid can be provided as an extrusion lubricant. As other examples, the particles can be impregnated with biphosphonates, forteo, prolia and fosemax on the surface or as separate substances mixed into the slurry. Other substances such as antibiotics (e.g. vancomycin), chemotherapeutic agents, and the like can also be added to the surface of the particles or as separate substances in the slurry. Particles made of materials other than bone can also form part of the slurry in some implementations.

The bone particles themselves may comprise cortical or cancellous bone, whether allograft, xenograft, or autologous. Cortical bone has favorable compressive strength to perform the desired structural support function. In some implementations, at least 90% of the bone particles are non-demineralized cortical bone particles. Regarding the size distribution of the particles, they can be no larger than the inner diameter of the catheter, and as noted above, may potentially be anywhere in the range of 1 micrometer to 1 millimeter. In some implementations, at least 90% of the bone particles have a characteristic size in the range of 50 to 1000 micrometers. Conceptually, bone particles in this size range may be analogized to grains of sand of varying coarseness. Because the particles may not be entirely spherical, the "characteristic size" of a given particle as defined herein is the diameter of a sphere having a volume equal to that of the actual particle.

A slurry containing substantially uniform particle characteristic sizes in the 50 to 1000 micrometer range may be used, wherein substantially uniform means that the distribution of characteristic sizes (full width at half maximum of a histogram) is within ±10% of the mean characteristic size of the particles in the mixture. Alternatively, the slurry may contain bone particles with two or more different sizes, where two particles are considered to have different sizes if the characteristic size of the larger divided by the characteristic size of the smaller is more than 1.5. Particle size distributions may be characterized by a parameter that may be referred to as the uniformity coefficient. This may be defined as D60/D10, where D60 means 60% of the particles by mass have equal to or smaller characteristic size. Similarly, D10 means that 10% of the particles by mass have equal to or smaller characteristic size. For example, a set of particles half of which (by mass) are 1000 micrometers and the other half (by mass) are 500 micrometers, would have a uniformity coefficient of 2. It can also be seen that a mixture of particles of uniform size would have a uniformity coefficient of 1. Generally, a higher uniformity coefficient corresponds to a greater range of particle characteristic sizes in the particle mixture.

Figure 4:
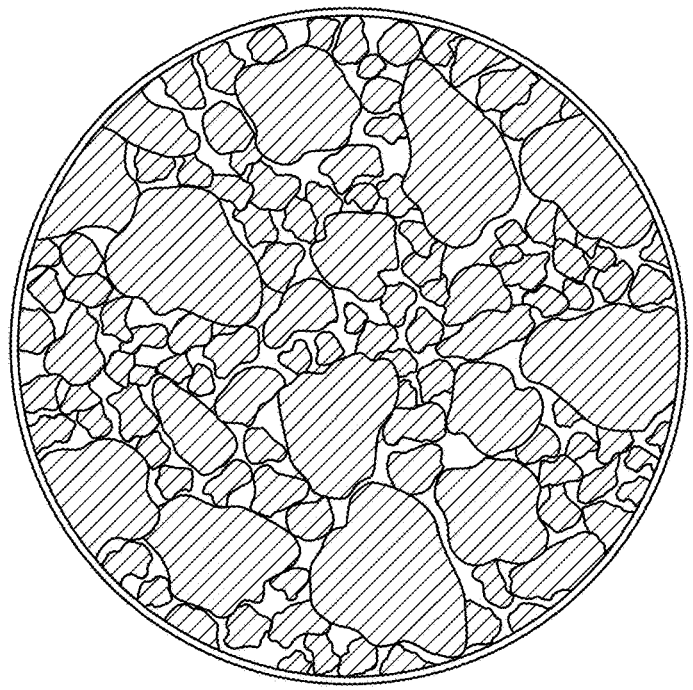
FIG. 4 illustrates a conceptual example of a bone particle size distribution, in accordance with some embodiments.

FIG. 4 shows a conceptual illustration of a particle distribution that may be suitable for the present application. The example of FIG. 4 may be referred to as "open graded," which generally means that there is a range of particle sizes, but there are few extremely small particles that would substantially fill in the voids between the larger and medium sized particles when they are packed together. In a packed mixture like this, structural support is provided by both the larger particles and the smaller particles. This may be more structurally sound than a substantially uniform particle mixture with fewer points of contact between particles.

In an open graded particle mixture, the open voids may comprise 15% to 25% of the total volume of the packed material. These voids can make the packed bone particle structure water permeable, making it easier and faster for the excess water from the injected slurry to be absorbed or removed as the bone particles pack together on the inside of the vertebral body. These voids also form pores that can be useful for bone ingrowth. Thus, it can be advantageous for the bone particles in the slurry to have a D60/D10 uniformity coefficient of at least 2. In some implementations, the uniformity coefficient is between 2 and 6. In some implementations, the uniformity coefficient is greater than 6. In some implementations, the range of characteristic sizes is limited to reliably produce pores in the packed material such as are shown in FIG. 4. For example, in some implementations, the mean characteristic size of the largest 10% by mass of the particles is no more than 5 times the mean characteristic size of the smallest 10% by mass of the particles.

It is possible to use more complex forms of bone particles as a component of the slurry as well. For example, flexible and compressible spongy webs of bone tissue that may be used as bioscaffolds have been created and are commercially available. Pieces of this type of bone material could be compressed while being injected in the slurry and can expand after exiting to the interior of the vertebral body.

The slurry pump 28 used for delivery of the particle slurry may be similar to a caulking gun or other pressurization device with a knob or trigger or the like to gradually and steadily pressurize the vertebral body with the slurry. The slurry pump may also have a pressure gauge to identify to the surgeon or treating physician how much pressure is being exerted by the slurry pump when performing the slurry injection. The slurry pump 28 should be able to create a pressure at the distal outlet(s) of the catheter inside the vertebral body of about 5-20 psi above ambient atmospheric pressure, similar to the intervertebral pressures that occur in conventional vertebroplasty and kyphoplasty procedures. How much pressure this requires at the proximal end of the catheter near or at the output of the slurry pump 28 will depend on the specific properties of the slurry such as viscosity, as well as the length, lumen diameter, and internal surface characteristics of the catheter. These factors will affect the pressure drop from the input to the output of the catheter. Balloon inflation syringes that are currently used in kyphoplasty procedures that have an output pressure capability of 200 to 700 psi and one of these types of inflation syringes could be used as the slurry pump 28. An electrical rotating auger drive pump could also be used as the slurry pump 28.

Figure 5:
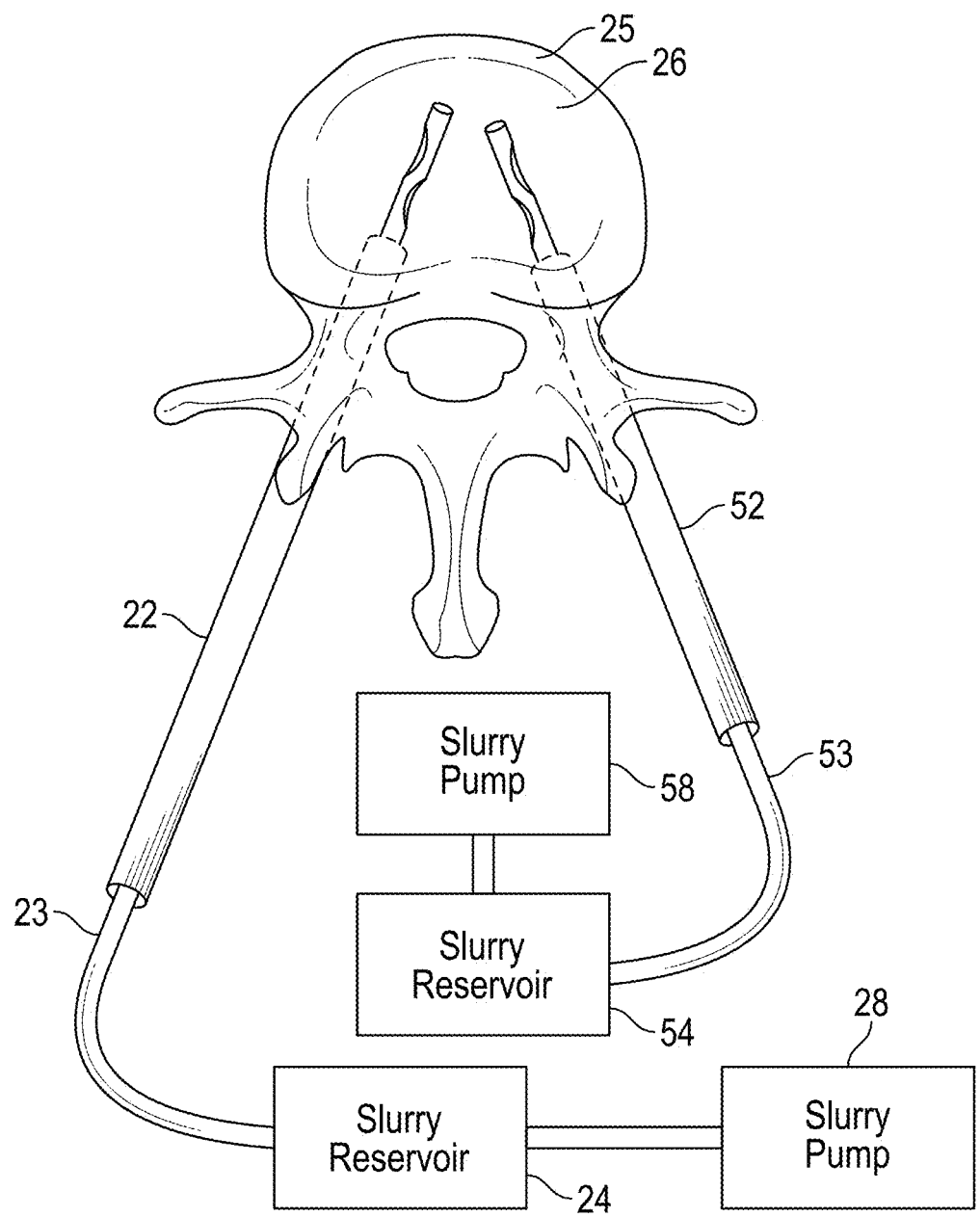
FIG. 5 is a schematic block diagram of another implementation of a system including two cannulas and two catheters, in accordance with some embodiments.

FIG. 5 illustrates a possible bi-pedicular approach, where two openings, two cannulas, and two catheters are used. In this implementation, slurry can be injected into the vertebra at the same time through two catheters. In FIG. 5 two slurry reservoirs 24, 54 and two slurry pumps 28, 58 are also illustrated. This may be convenient for separate monitoring and control of the slurry injection in the two catheters 23, 53. Also, it distributes the pressurization duty across two separate systems. It will be appreciated, however, that these could be combined into a single reservoir and single pump if desired.

Figure 6:
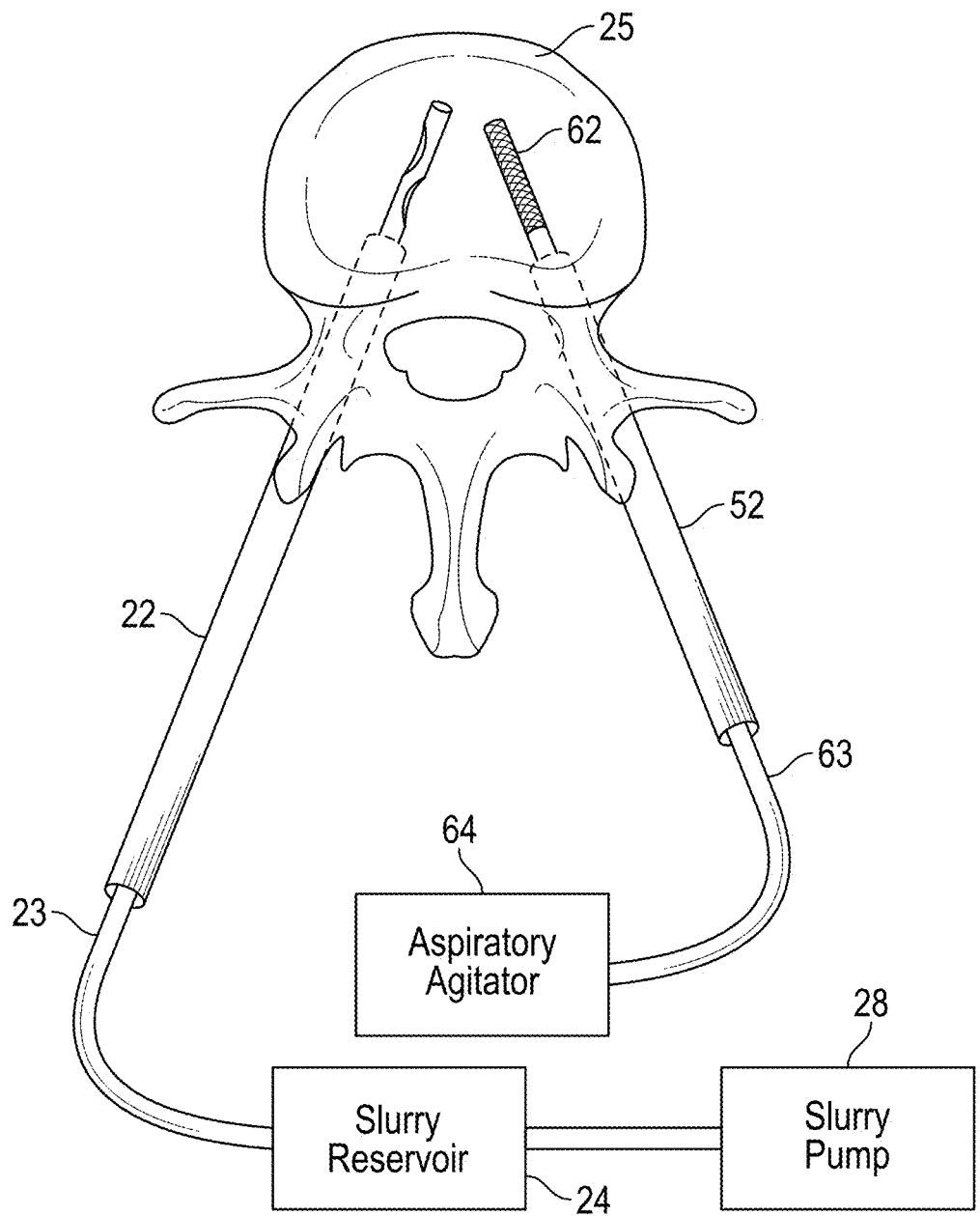
FIG. 6 is a schematic block diagram of another implementation of a system including an aspirator, in accordance with some embodiments.

FIG. 6 illustrates another implementation of the bi-pedicular access also illustrated in FIG. 5. In the implementation of FIG. 6, the second catheter 63 may not be used as another injection pathway for slurry. Instead, the distal end of the second catheter 63 comprises a filtered opening 62. The proximal end of the second catheter 63 is coupled to an aspirator 64 which can be used to aspirate excess slurry liquid as the bone particles of the slurry settle and pack within the vertebral body 25. Alternatively or additionally, the aspirator 64 can provide an agitation function that can agitate the injected slurry material within the vertebral body 25 as the bone particles of the slurry settle and pack within the vertebral body 25. This can help ensure that bone particles of different sizes in the slurry remain more homogeneously distributed settle and pack within the vertebral body 25. To perform agitation and aspiration, the aspirator/agitator 64 may alternate between fluid injection and fluid aspiration. For example, it may inject 0.1 cc, then aspirate 0.2 cc, and so on in rapid succession. The aspiration and agitation functions could also be completely separate. An implantation like this may include reciprocating fins on the second catheter for example. As a further technique for agitation of the slurry as it is injected, the slurry pump 28 could have a mechanism to vibrate or reciprocate the distal end of either or both of the first or second catheters 23, 63 and/or cannulas 22, 52 such as with ultrasound, piezoelectric transducers, or other mechanical means.

Example Systems and Methods—Bone Pellet Injection

In other implementations, rather than a relatively loose particle slurry as described above, bone pellets that contain little or even no fluid may be injected into the vertebral body either one at a time or in discrete sets. This configuration of injected material can be pushed easily through a narrow needle or cannula into the vertebral body. In some implementations, as described further below, the pellets can be a combination of cortical and cancellous bone. After injection of some pellets into the internal vertebral cavity, a kyphoplasty balloon can be inflated to push the pellets against the walls of the cavity, thereby crushing the pellets and filling the tissue interstices at the periphery of the cavity. The process of pellet injection followed by balloon inflation can be repeated to incrementally fill the cavity with layers of compacted bone particles. As the cavity is filled with pellets, each subsequent expansion of the balloon is smaller as the pellets are crushed against the inside of the cavity and the cavity is filled.

Figure 7A:
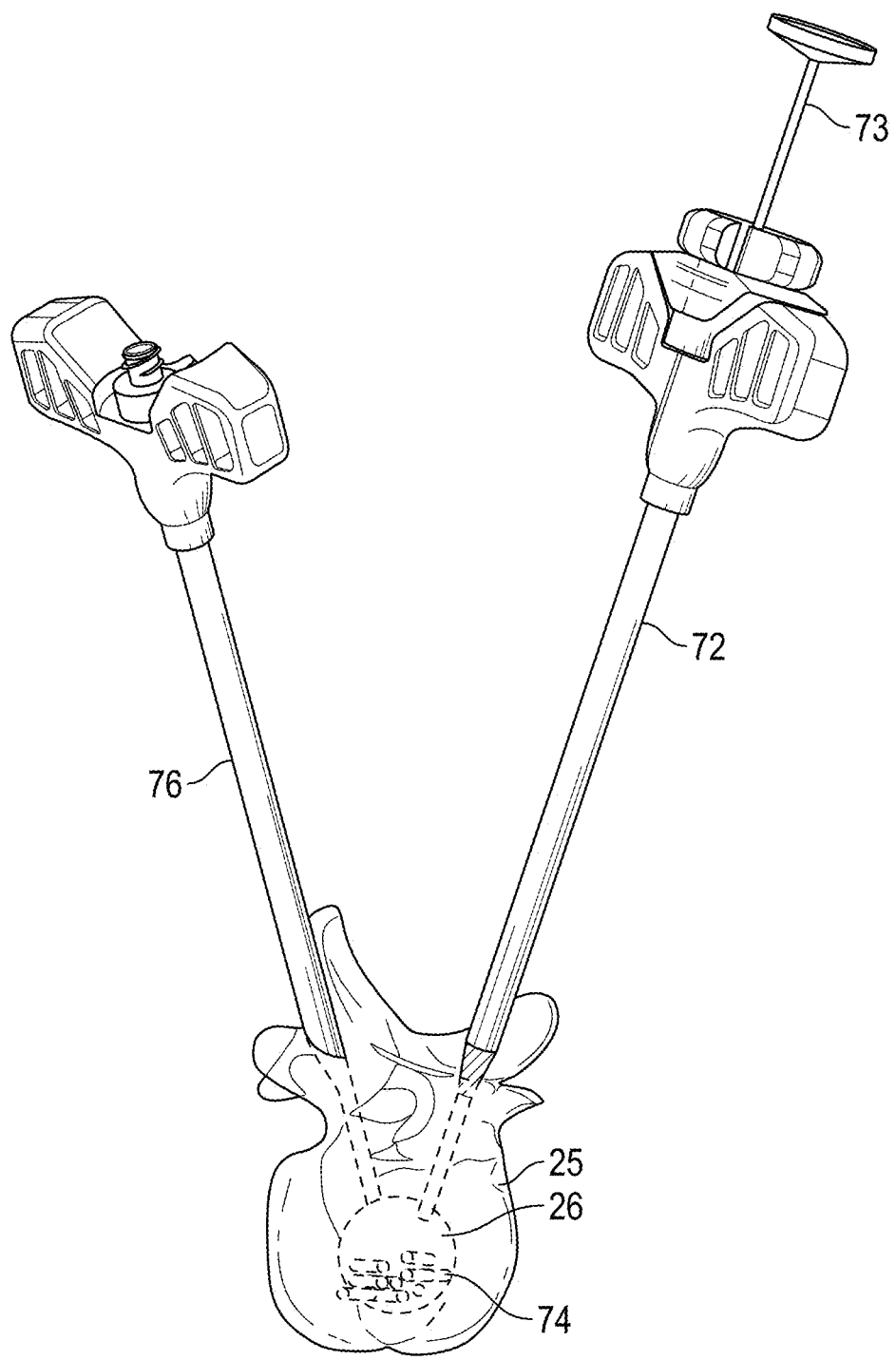
FIG. 7A illustrates a system for injecting bone pellets into a bone, in accordance with some embodiments.

Referring now to FIG. 7A, an example apparatus and system for performing such a procedure is illustrated. In FIG. 7A, a bone injector 72 has a plunger 73 that can be used to push pellets 74 out of the distal end of the injector which may be installed through the pedicle in a manner similar to the slurry injectors described above. As shown in FIG. 7A, the pellets 74 may be cylindrical in shape and may be pushed down a cylindrical lumen in the injection needle using the plunger 73. The lumen diameter may be slightly larger than the diameter of the pellets 74. The pellets 74 themselves may be formed in a variety of ways, as will be described in connection with at least FIGS. 7B-7D below.

Figure 7B:
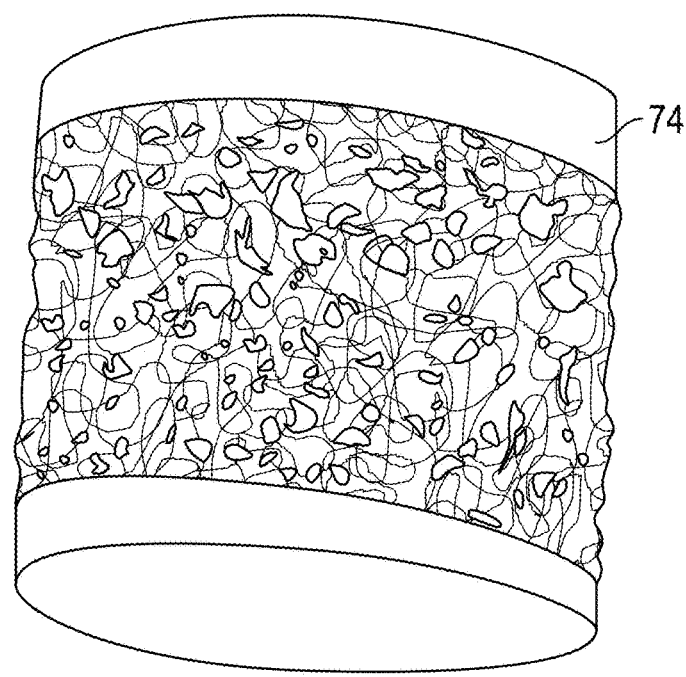
FIG. 7B illustrates a bone pellet, in accordance with some embodiments.

One possible embodiment is illustrated in FIG. 7B. In this embodiment, each pellet comprises a freeze dried bicortical dowel, comprising a cylinder of cancellous bone with cortical endcaps. Such dowels are commercially available and may be obtained by drilling cores through the thickness of donor ilium bone. In accordance with typical ilium thickness, these dowels are generally about 9 to 15 mm long. The diameter of the dowel will depend on the coring drill bit size. Such ilium dowels are conventionally made in diameters of 10-15 mm. In the present application, however, a diameter of 0.5-6 mm, or in some embodiments 1.5-5.0 mm, is desirable. These dowels have the desirable properties that they can be easily pushed down an injection tube having an inner diameter no less than, and typically slightly larger than (e.g. 0.01 to 1 mm larger than), the dowel diameter. Dowel diameters may be selected to be slightly smaller than the inner diameter of a standard needle gauge that will be used to introduce the pellets into the vertebral body, such as from 7 to 14 gauge.

Figure 7C:
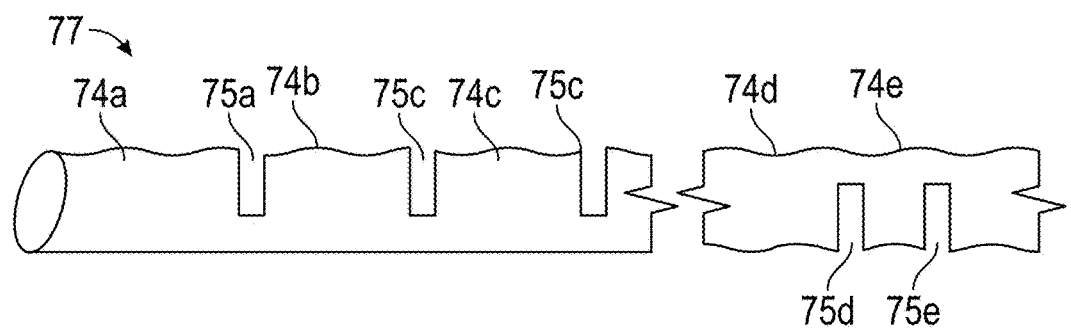
FIG. 7C illustrates a rod of bone configured to fragment into a plurality of bone pellets, in accordance with some embodiments.

Suitable pellets can be formed in other ways as well. For example, FIG. 7C illustrates an extended rod 77 of bone having a plurality of transverse cuts 75a-75e extending incompletely therethrough in a direction substantially transverse to the direction of extension of rod 77. In some embodiments, rod 77 can have a substantially cylindrical shape. However, the present disclosure is not so limited and rod 77 can have any cross-sectional shape. When forcefully driven into the vertebral body, rod 77 may fragment at cuts 75a-75e such that a plurality of bone pellets 74a-74e are formed within the vertebral body. In some embodiments, each of the plurality of transverse cuts 75a-75e may have a same, first orientation with respect to rod 77. In some other embodiments, some of the plurality of transverse cuts, e.g., 75a-75c, may be made to have a first orientation with respect to rod 77, while some other of the plurality of cuts, e.g., 75d and 75e, may be made to have at least a second orientation, different from the first orientation, with respect to rod 77. In some embodiments, making transverse cuts 75a-75e with multiple orientations with respect to rod 77 can help ensure proper fragmentation of rod 77 into pellets 74a-74e upon forceful insertion into the vertebral body.

Figure 7D:
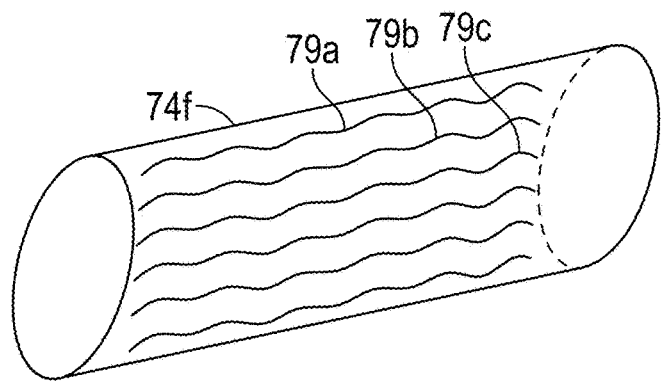
FIG. 7D illustrates a bone pellet formed from compressed bone strips, in accordance with some embodiments.
Figure 8A:
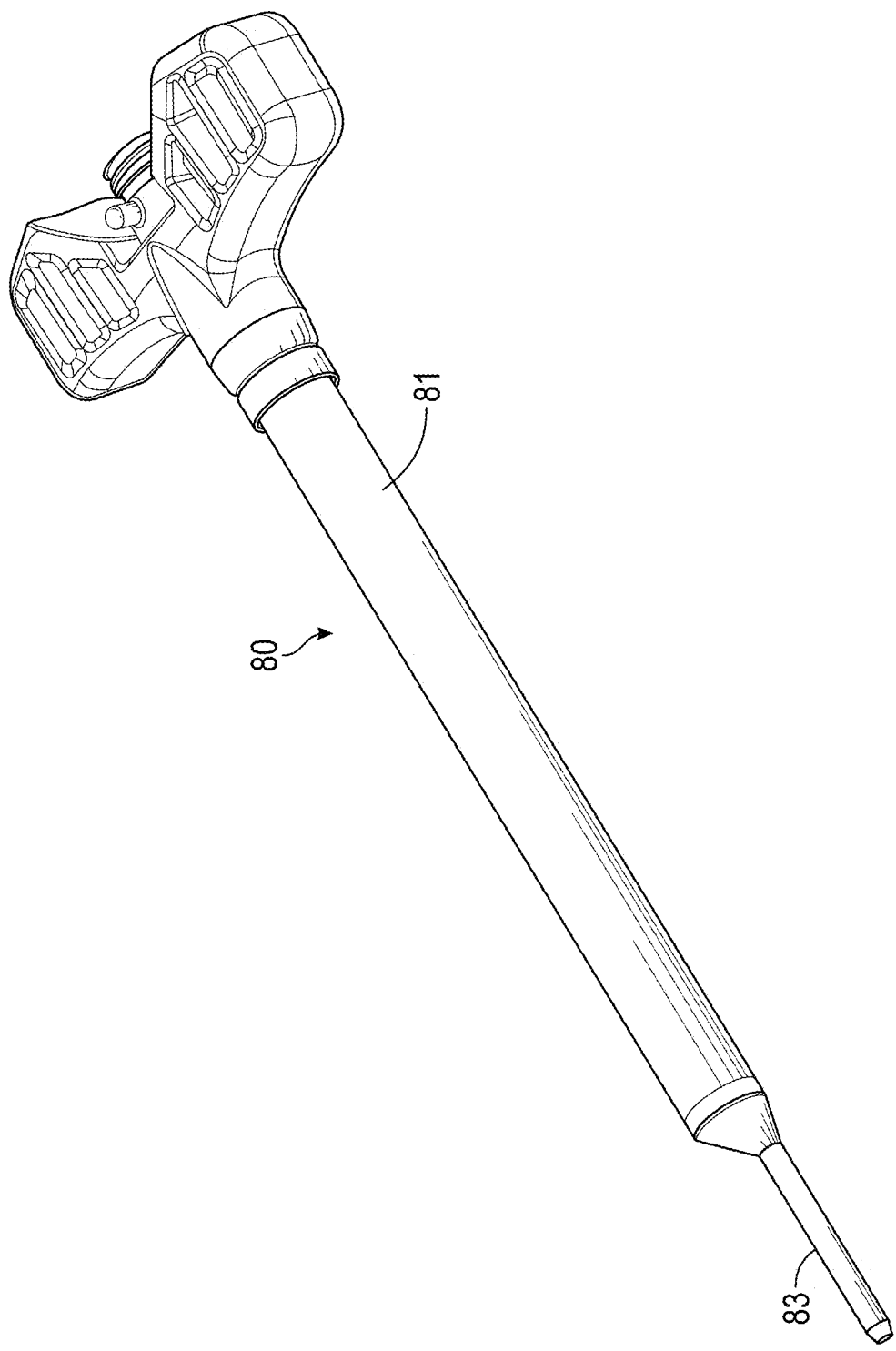
FIG. 8A illustrates a cartridge configured to hold a plurality of bone pellets, in accordance with some embodiments.
Figure 8B:
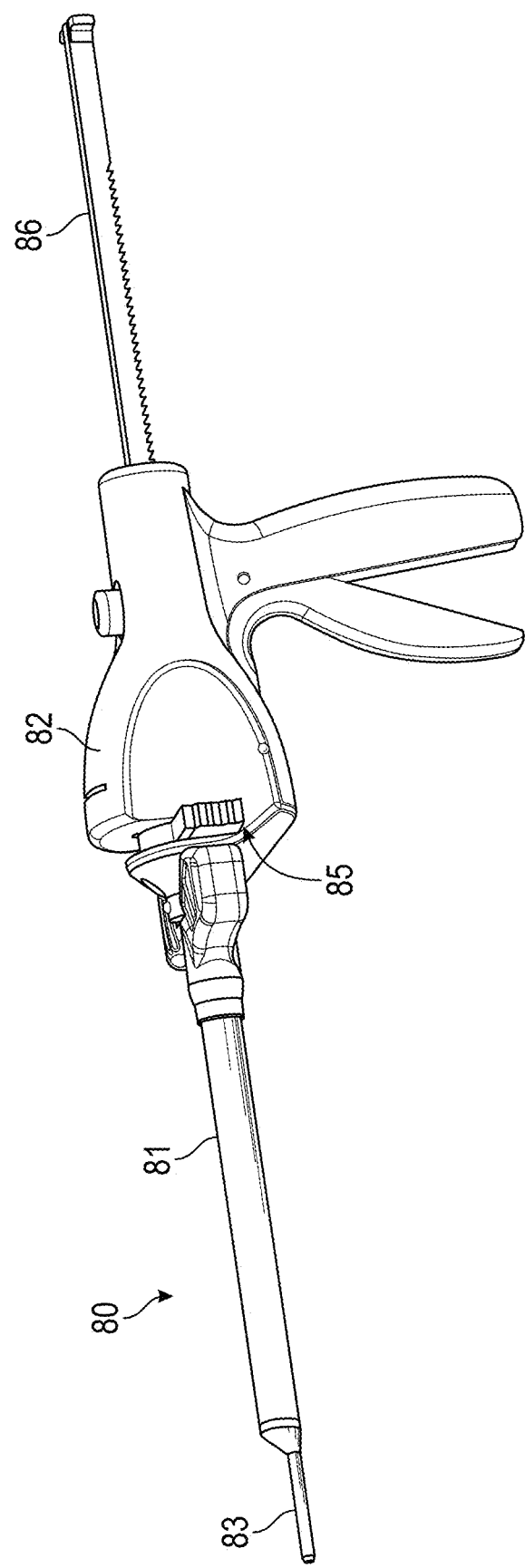
FIG. 8B illustrates the cartridge of FIG. 8A attached to a pellet delivery apparatus, in accordance with some embodiments.
Figure 8C:
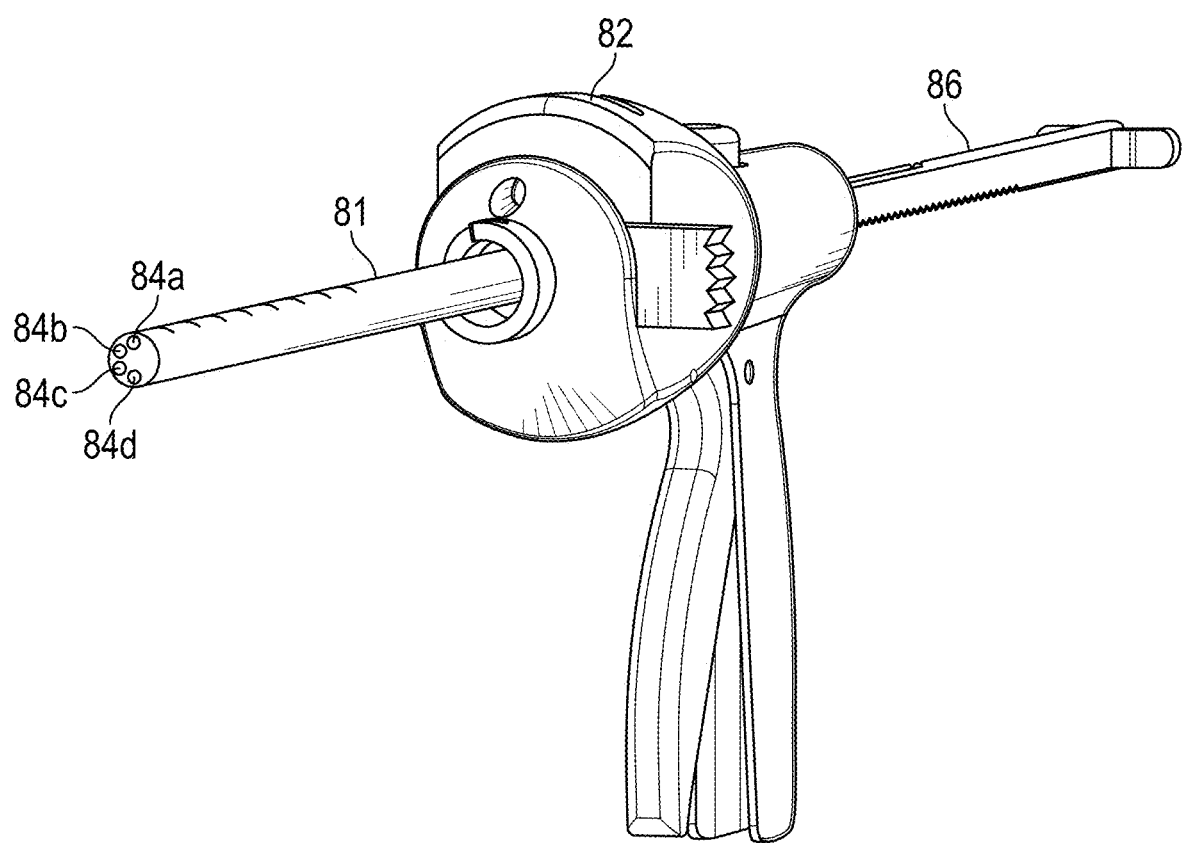
FIG. 8C illustrates a plurality of barrels within the cartridge of FIGS. 8A-8B, each configured to hold a plurality of bone pellets, in accordance with some embodiments.
Figure 8D:
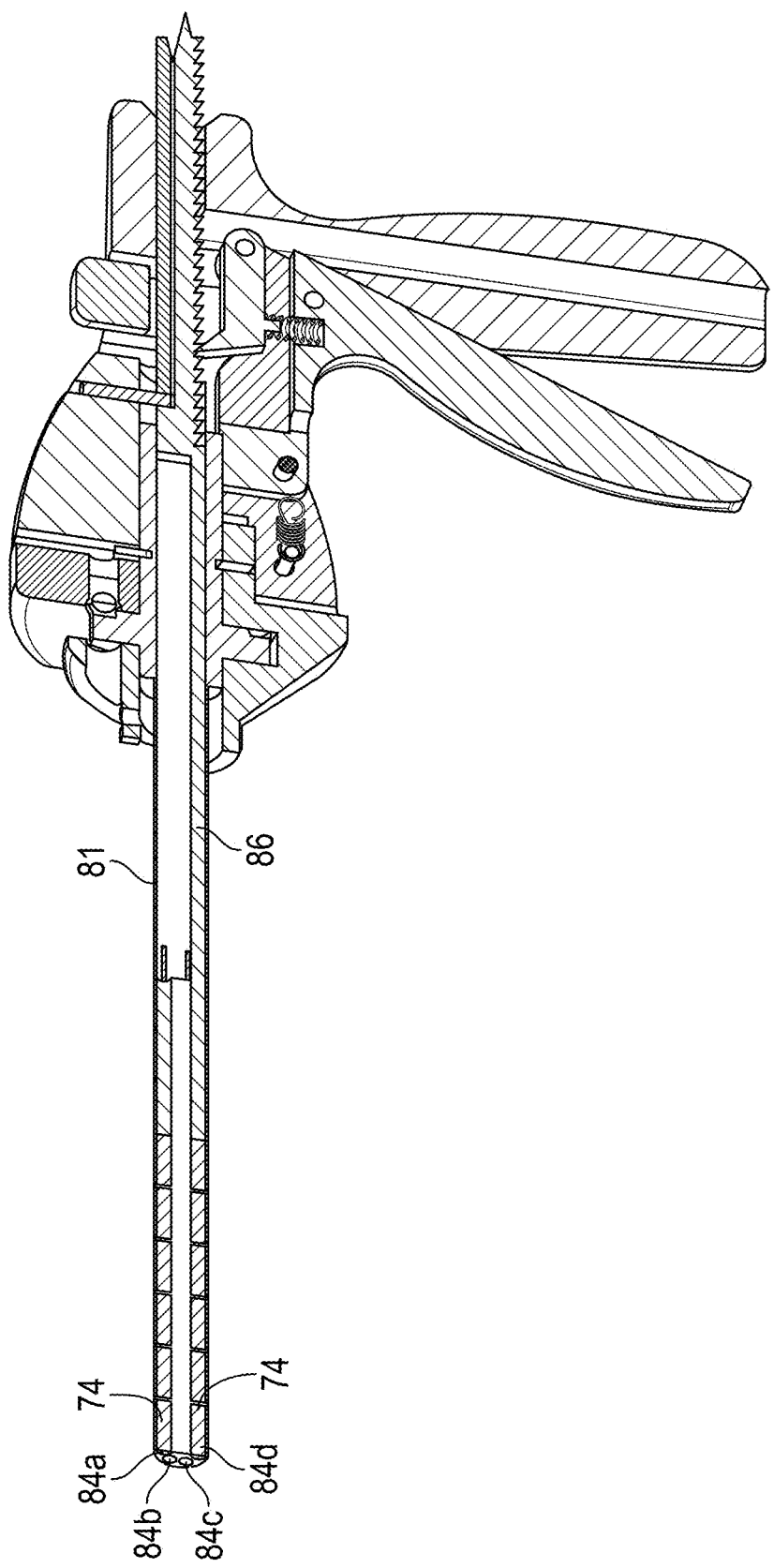
FIG. 8D illustrates a cutaway view of the cartridge and pellet delivery apparatus of FIGS. 8B-8C including a ratcheted plunger, in accordance with some embodiments.
Figure 8E:
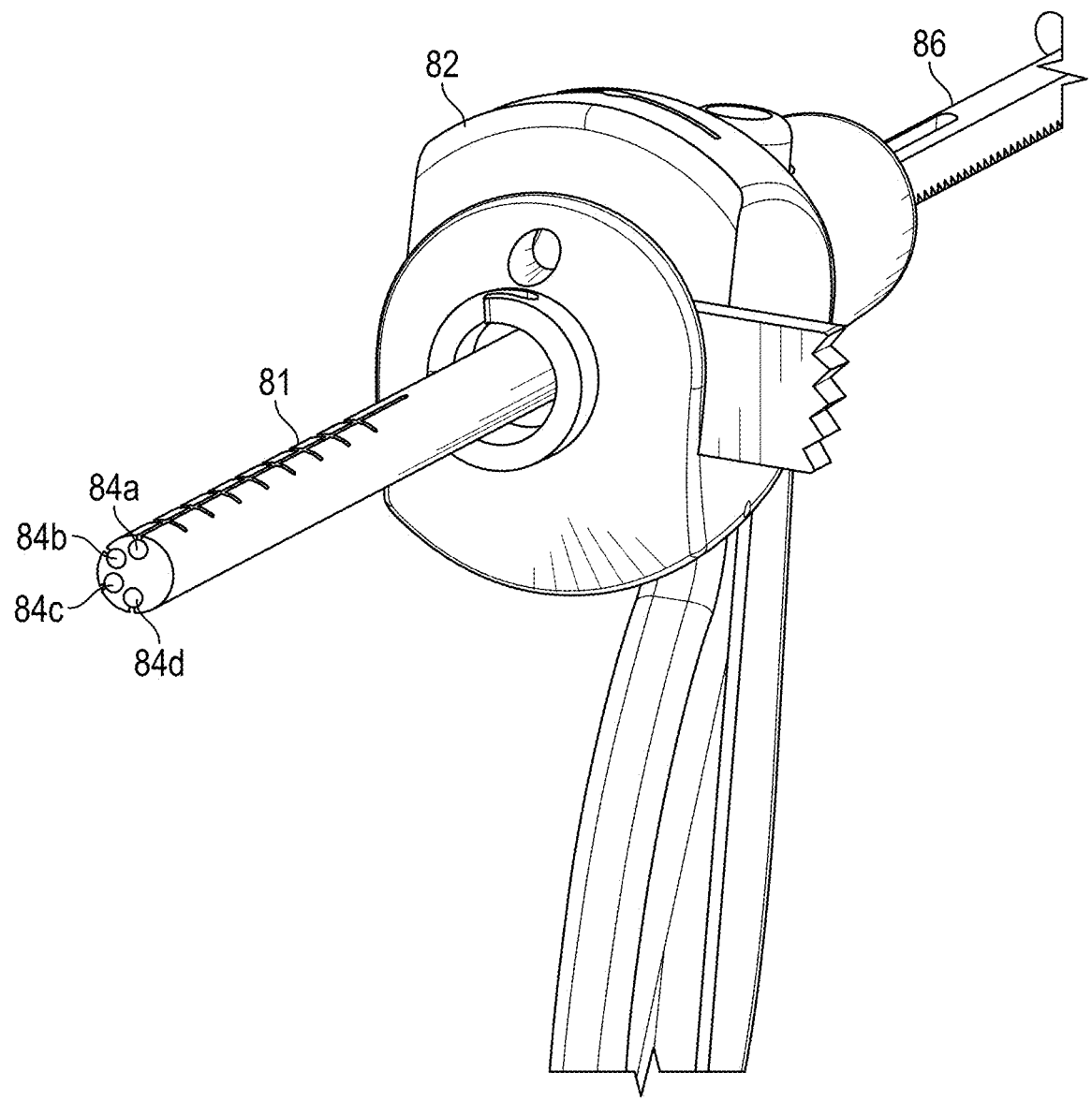
FIG. 8E illustrates a magnified view of the plurality of barrels of the cartridge coupled to the pellet delivery apparatus, in accordance with some embodiments.

As yet another example, as illustrated in FIG. 7D, loose cortical and/or cancellous bone chips and/or strips 79a-79c, or a mixture thereof, can be mechanically compressed into a pellet 74f having a cylindrical or other shape. When removed from such a compression mold, compressed strips 79a-79c may generally maintain their pellet shape until inserted and compressed/crushed inside a vertebral body. If desired, a binder material such as saline or perhaps cured or uncured PMMA can be introduced into the compression mold with strips 79a-79c to facilitate the maintenance of pellet shape prior to use. In some embodiments, strips 79a-79c can have substantially the same length or, alternatively, variable lengths with respect to one another. In some embodiments, pellets 74f may be molded such that their substantially circular faces are oriented substantially perpendicular to a length of extension of the pellet. However, the present disclosure is not so limited and any orientation of the faces of pellet 74f with respect to its length of extension and/or any shape are also contemplated.

Regardless of how the pellets are formed or their shape, pellets may also or alternatively be coated or dipped in binders, lubricants, and/or therapeutic substances such as BMP or anesthetic.

In one implementation, as shown in FIGS. 8A through 8E, a system/kit for stabilization of vertebral bodies may include a cartridge 80 that can be removably attached to a pellet delivery apparatus, e.g., gun, 82. In some embodiments, gun 82 may also be referred to as a pump. The cartridge 80 may include an internal shaft 81 with a plurality circumferentially spaced lumens or barrels 84a-84d (see FIGS. 8C, 8D, and 8E) containing bone pellets 74 in any form as described anywhere in this disclosure. When attached to the pellet delivery gun 82, the internal shaft 81 can be rotated with a handle 85 such that each barrel 84a-84d can be selectively aligned with an outlet needle 83 and a ratcheted plunger 86 in the pellet delivery gun 82. Each barrel 84a-84d may hold several pellets 74 (e.g. 5-15 pellets). In operation, a barrel 84d containing pellets 74 is aligned with the plunger 86 and outlet needle 83, and some or all of the pellets 74 in that barrel 84d are pushed down and out of the barrel 84d by the plunger 86 into the internal cavity 26 of the vertebral body 25. Then, the kyphoplasty balloon (not shown in FIGS. 8A-8E but see kyphoplasty balloon(s) 281,282 in at least FIG. 28) is inflated to compress and crush the pellets 74 into the surrounding tissue interstices as described above and/or below. This may be repeated until the barrel 84d is empty. When that barrel 84d is empty, the handle 85 is rotated to align the next barrel 84a with the outlet 83 and plunger 86 and the process is repeated. When a cartridge 80 is empty, it may be replaced with another cartridge 80. Multiple barrels 84a-84d of multiple cartridges 80 may be sequentially emptied of pellets 74 into a vertebral body 25, with the kyphoplasty balloon 351 being inflated between each increment of inserted pellets 74. In various embodiments, anywhere from 0.1 to 1 cc of bone pellets 74 may be inserted into the vertebral body 25 between each expansion of the kyphoplasty balloon 351.

A surgical kit may thus include one or more cartridges 80 each with one or more lumens, e.g., barrels, 84a-84d sized to accept bone pellets 74 described above. In some embodiments, the kit may include one or more cartridges 80 pre-loaded with bone pellets 74. As described above, each cartridge 80 may be removably attached to a pellet delivery gun 82 configured to push pellets 74 out of the cartridges 80.

In addition to or alternatively to bone pellets 74, other types of pellets such as PMMA or titanium spheres may be placed into the lumens, e.g., barrels, 84a-84d in the cartridges 80. Instead of the pellet delivery device 82 and kyphoplasty balloon 351 being separate devices, they could be combined into a common device. As a common device, two could be used at the same time, one through each pedicle.

Additional Specific Embodiments

Figure 9A:
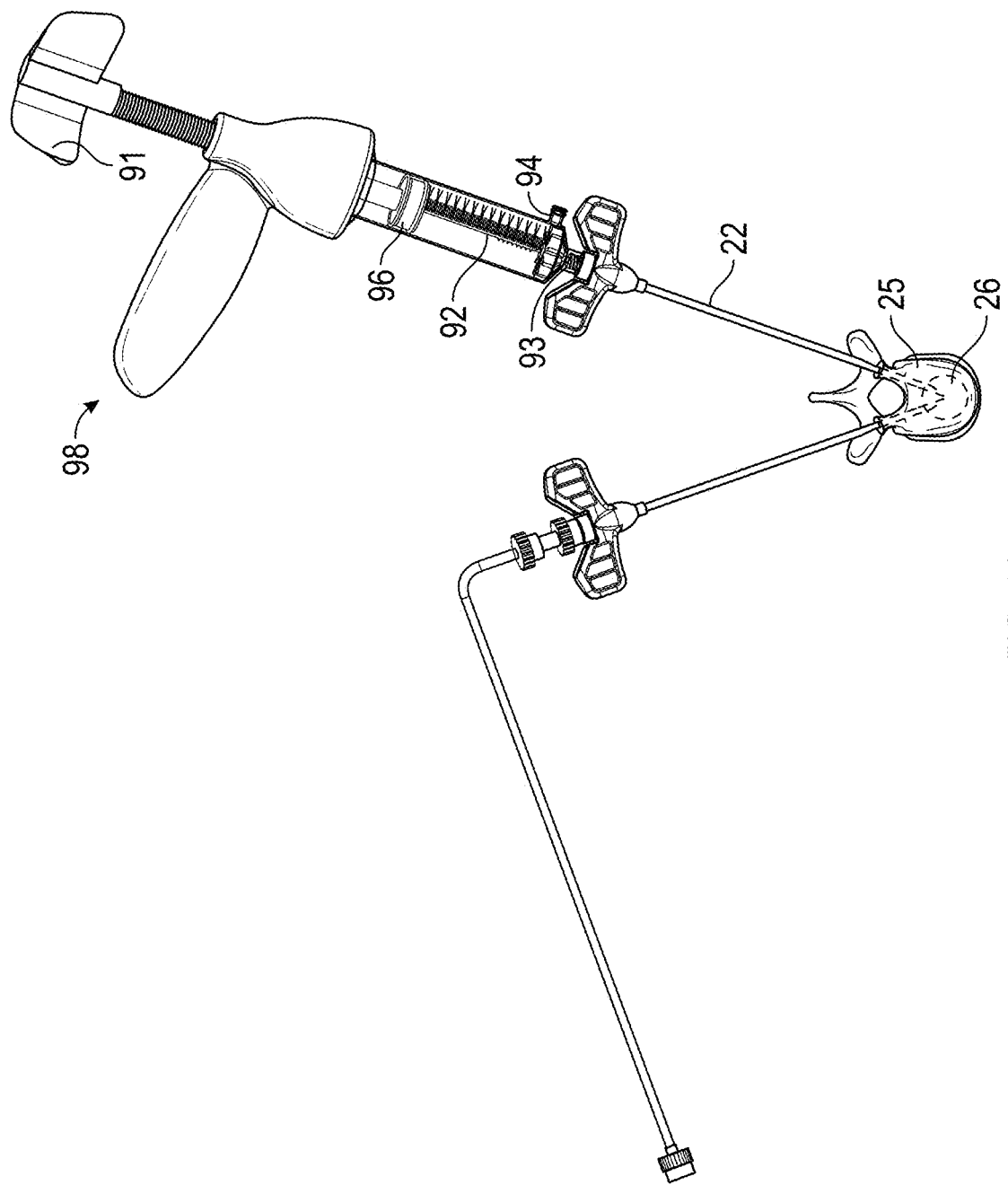
FIG. 9A illustrates a system for injecting bone slurry into a bone, in accordance with some embodiments.
Figure 9B:
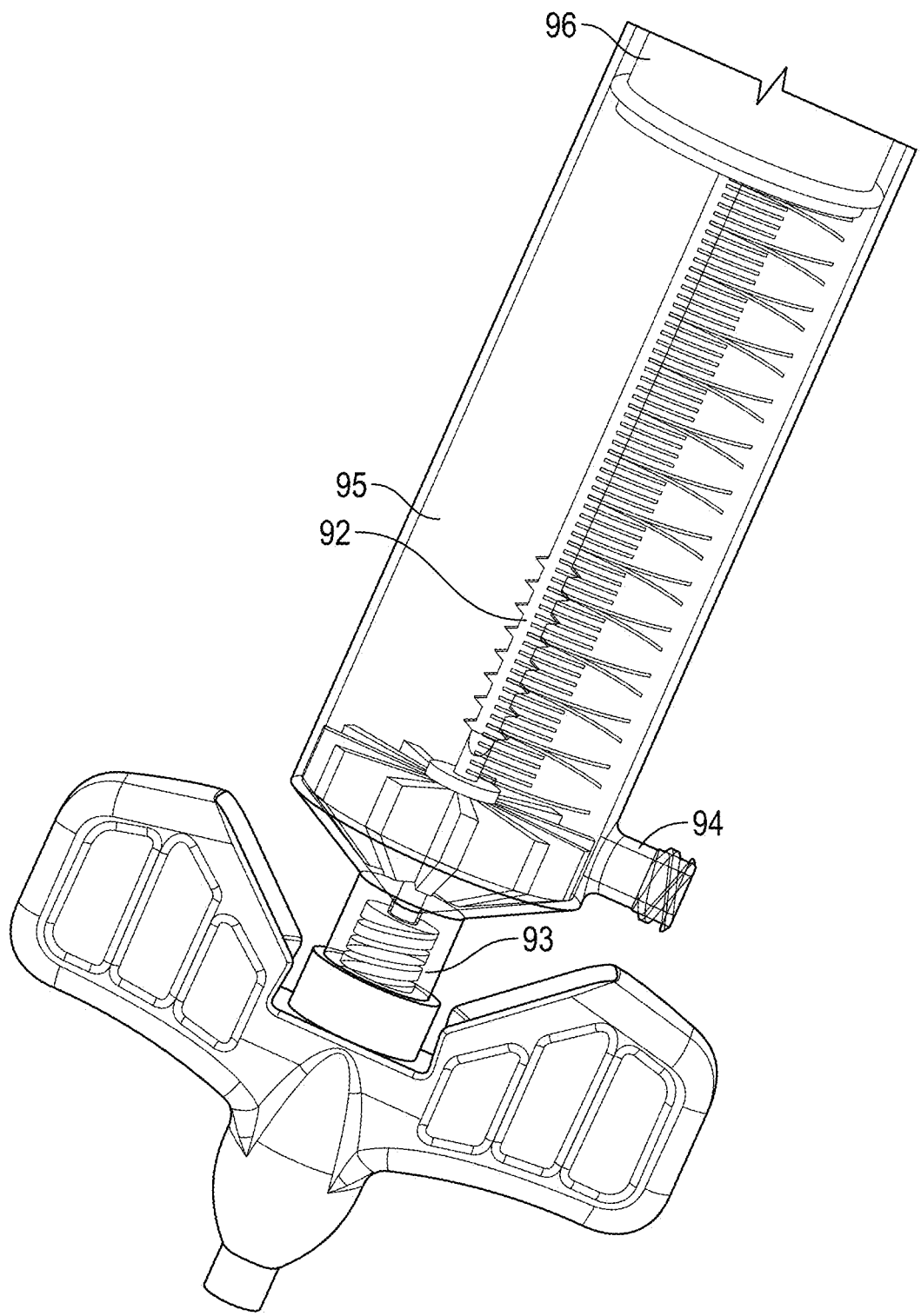
FIG. 9B illustrates a magnified view of portions of the system of FIG. 9A, in accordance with some embodiments.

FIGS. 9A and 9B illustrate an embodiment wherein a controlled amount of fluid can be added to dry bone particles 95 at the outlet 93 of a pump 98, which in this case is formed similar to a syringe. Twist action at the handle 91 works through a gear set in the plunger 96 to drive an internal augur 92. For example, as shown in the magnified view of FIG. 9B, twisting of the handle 91 turns auger 92 and causes the plunger 96 to push dry bone particles 95 toward the outlet 93 of the pump 98. A fluid inlet port 94 may feed fluid into the pump 98 such that the fluid and the dry bone particles 95 mix at or near outlet 93 to form a bone slurry as or similar to that previously described, which the pump 98 then forces through the cannula 22 and into the internal cavity 26 of the vertebral body 25.

Figure 10A:
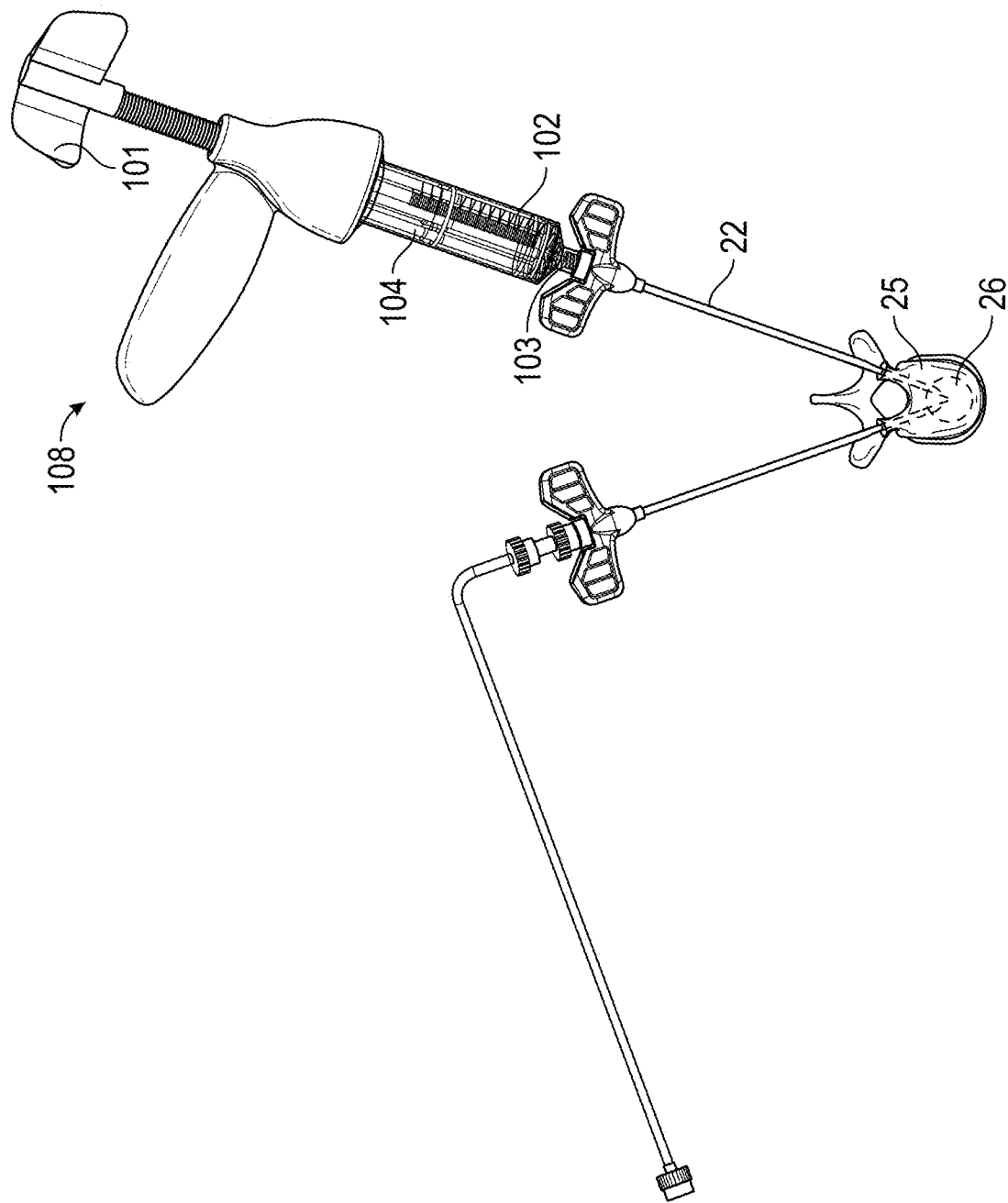
FIG. 10A illustrates another system for injecting bone slurry into a bone, in accordance with some embodiments.
Figure 10B:
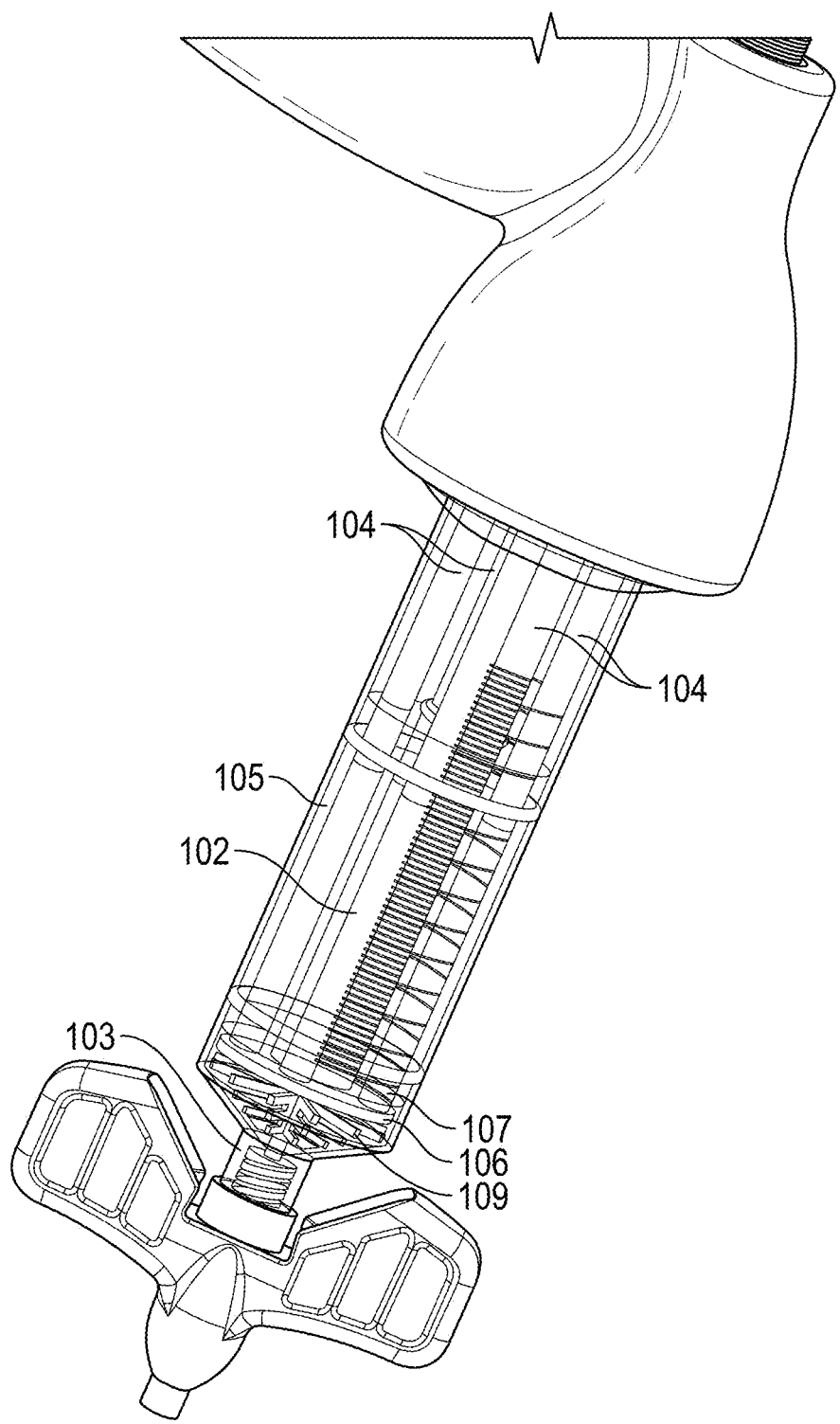
FIG. 10B illustrates a magnified view of portions of the system of FIG. 10A, in accordance with some embodiments.

FIGS. 10A and 10B also mixes bone particles 95 with fluid at the bottom of the syringe chamber. In this embodiment, separate fluid compartments 104 and dry bone compartments 105 are provided in the syringe chamber of pump 108. A rotating opening or openings 107 is provided in a disk 106 at the bottom above the mixing chamber 109. Twist action of a handle 101 rotates the disk 106, metering a controlled amount of bone particles and fluid to the outlet 103 to form a bone slurry as or similar to that previously described, which the pump 98 then forces through the cannula 22 and into the internal cavity 26 of the vertebral body 25.

Figure 11A:
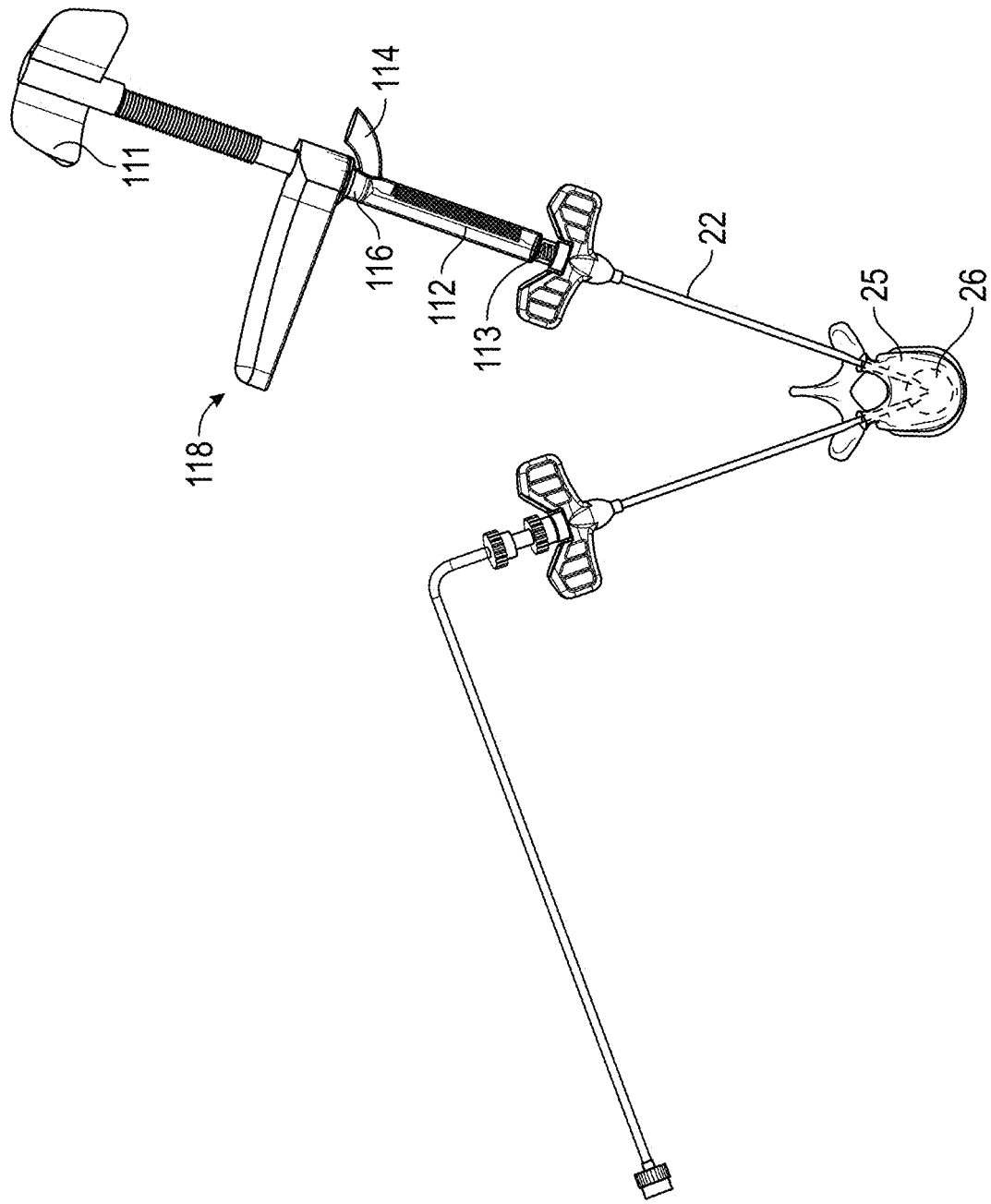
FIG. 11A illustrates yet another system for injecting bone slurry into a bone, in accordance with some embodiments.
Figure 11B:
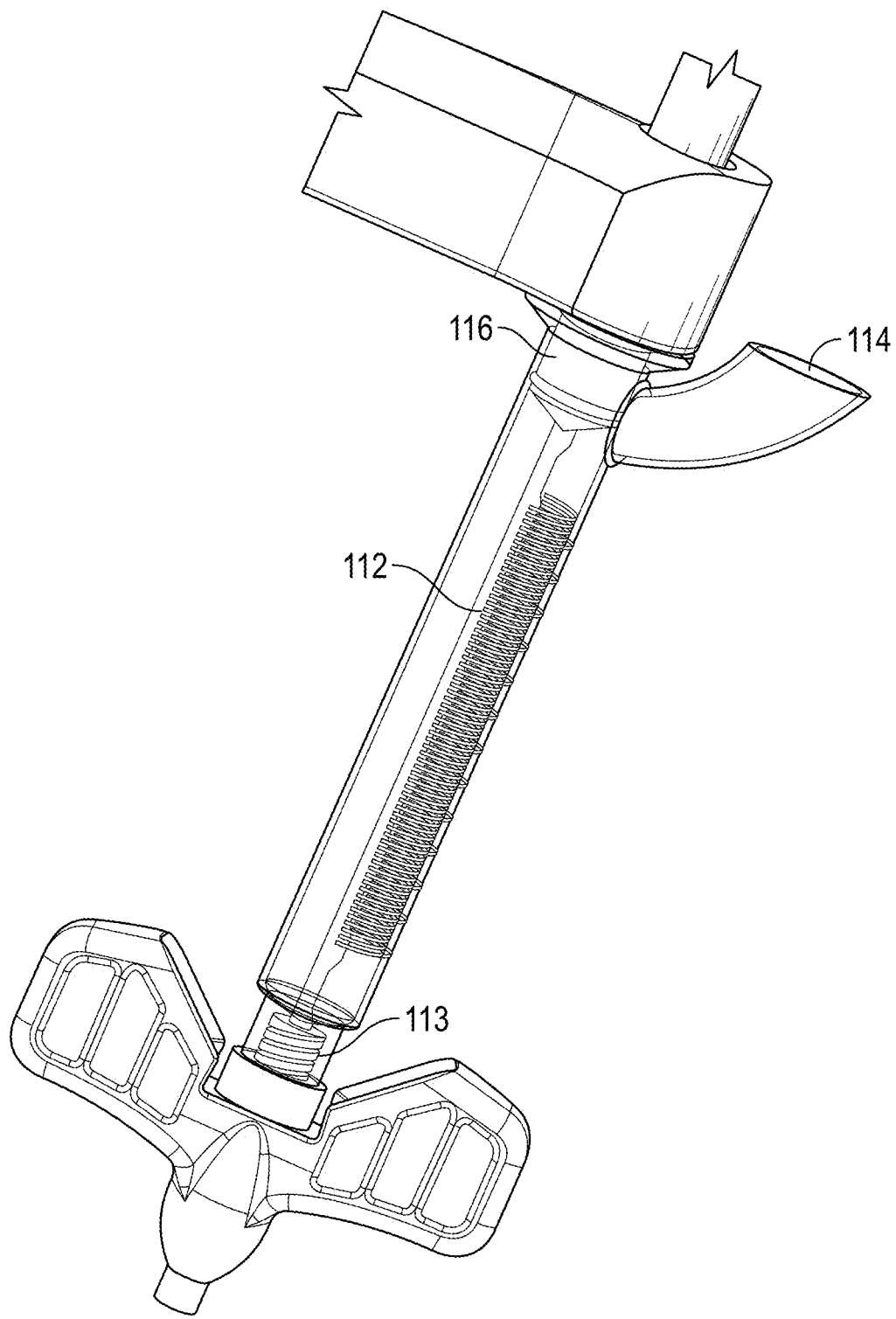
FIG. 11B illustrates a magnified view of portions of the system of FIG. 11A, in accordance with some embodiments.
Figure 12A:
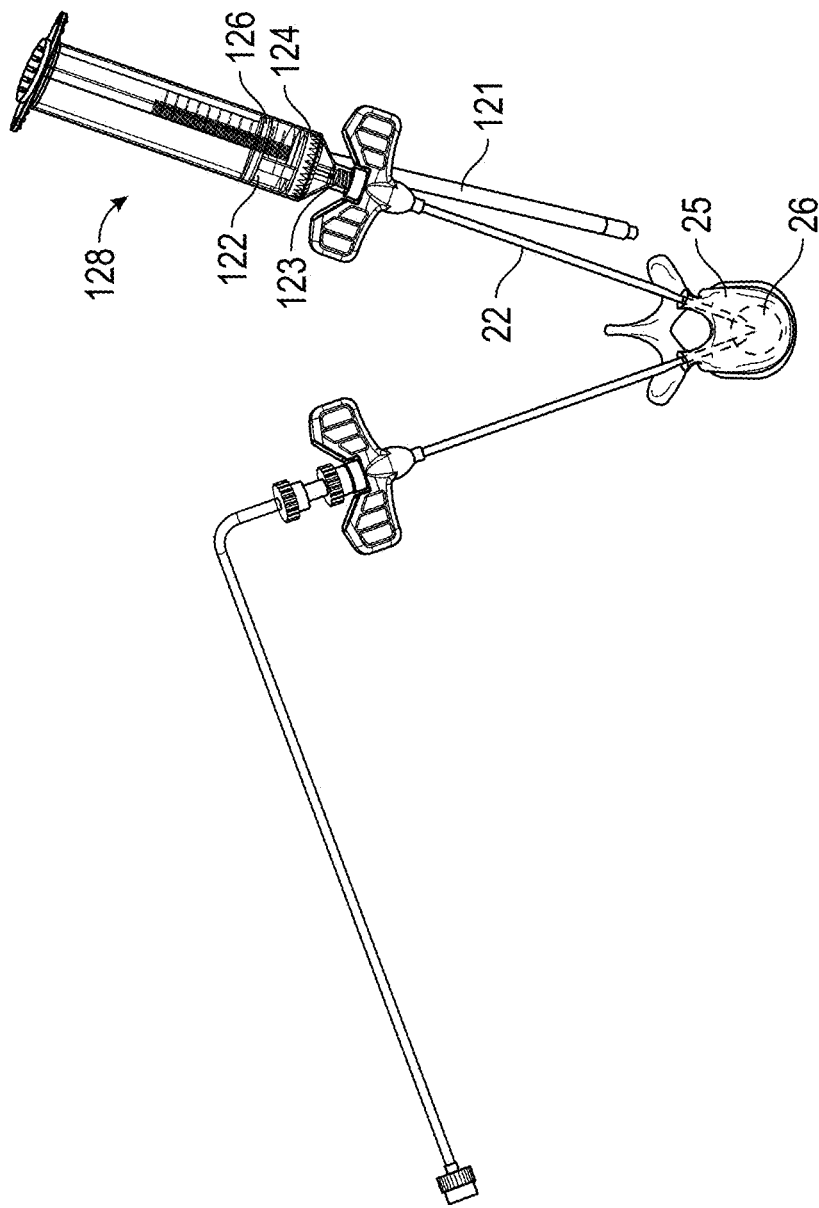
FIG. 12A illustrates yet another system for injecting bone slurry into a bone, in accordance with some embodiments.
Figure 12B:
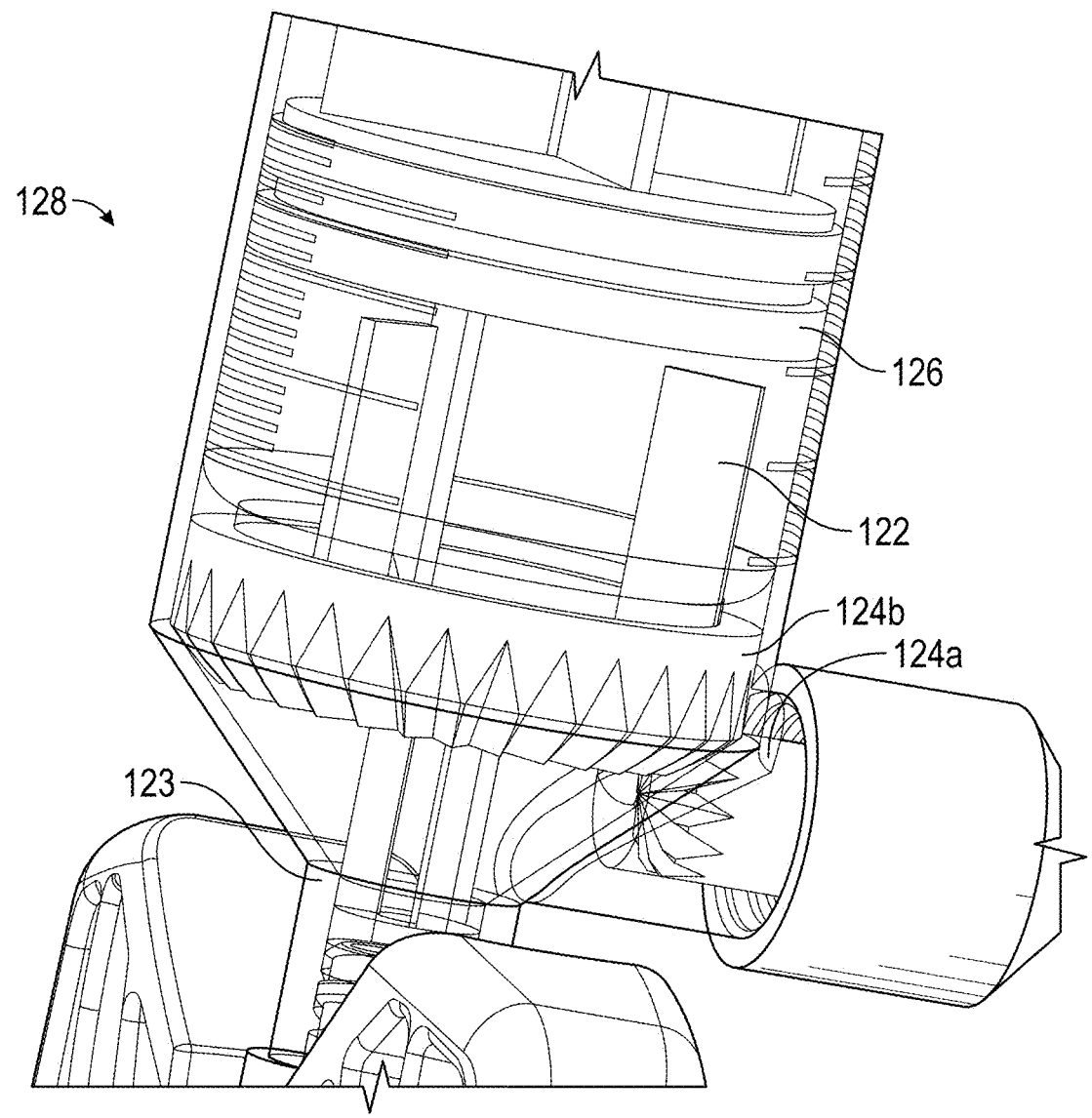
FIG. 12B illustrates a magnified view of portions of the system of FIG. 12A, in accordance with some embodiments.

FIGS. 11A, 11B, 12A and 12B show pumps 118, 128 with an internal augur 112, 122, where one pump 118 is hand driven (see FIGS. 11A and 11B) and where one pump 128 is driven with an external motor (see FIGS. 12A and 12B).

For example, FIGS. 11A and 11B illustrate an embodiment wherein a controlled amount of bone slurry can be added to the pump 118 via inlet port 114, which is illustrated as being disposed at or near an end of the pump 118 that is proximal to a plunger 116. Pump 118 is illustrated as formed similar to a syringe. Twist action at the handle 111 drives an auger 112 and moves the plunger 116 toward outlet 113. For example, as shown in the magnified view of FIG. 11B, twisting of the handle 111 turns auger 112 and causes the plunger 116 to push bone slurry toward the outlet 113 of the pump 118. The pump 118 then forces the bone slurry through the cannula 22 and into the internal cavity 26 of the vertebral body 25.

FIGS. 12A and 12B illustrate an embodiment wherein an external motor (not shown) is configured to rotate a drive shaft 121, which rotates a gear set 124, which causes a plunger 126 to pump a controlled amount of bone slurry out of the pump 128. Pump 128 is illustrated as formed similar to a syringe. For example, as shown in the magnified view of FIG. 12B, torque from the external motor rotates the drive shaft 121, which rotates a first gear 124a, which meshes with and rotates a second gear 124b, which turns auger 122 and causes the plunger 126 to advance toward and push bone slurry through the outlet 123 of the pump 128. The pump 128 then forces the bone slurry through the cannula 22 and into the internal cavity 26 of the vertebral body 25.

Figure 13A:
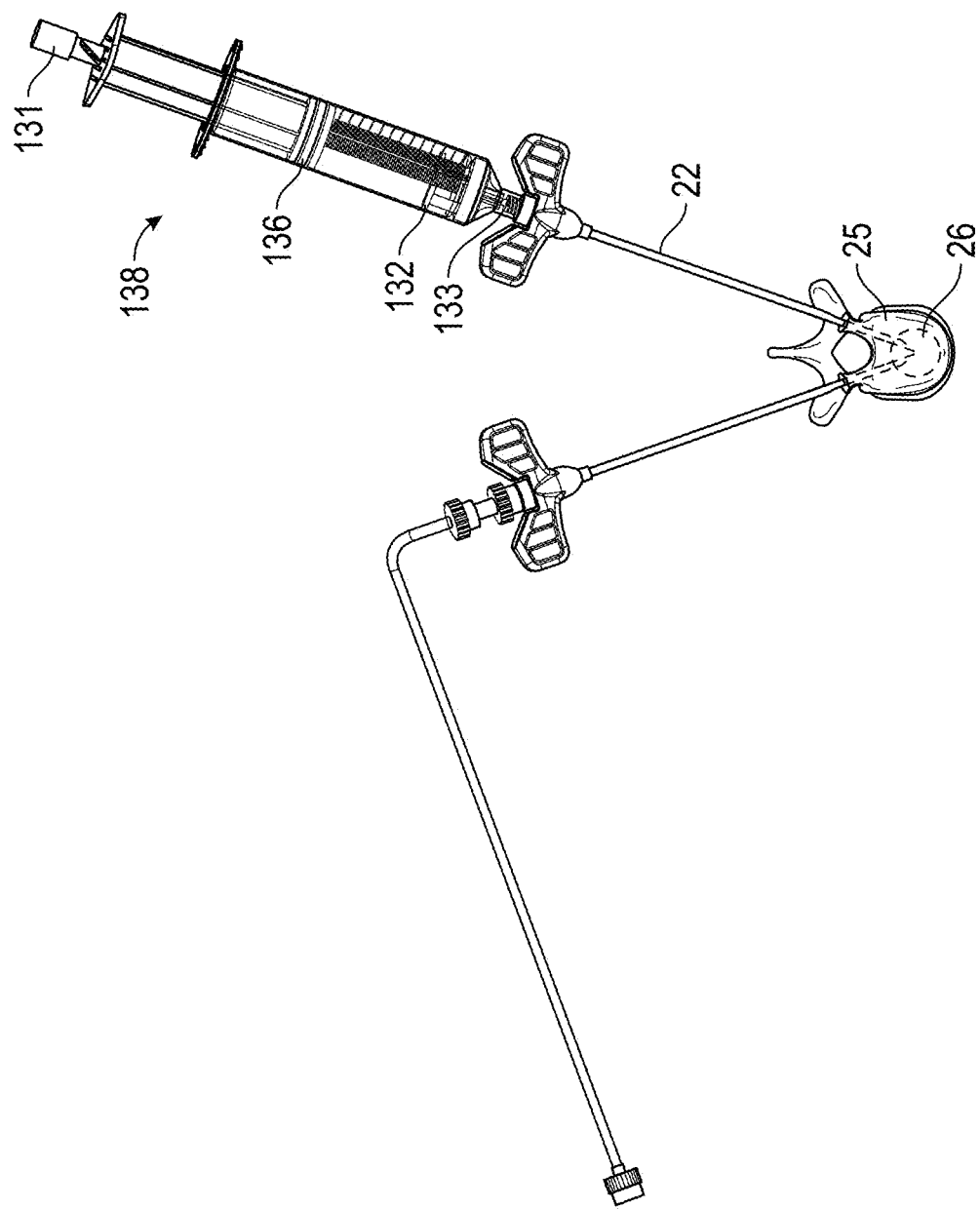
FIG. 13A illustrates yet another system for injecting bone slurry into a bone, in accordance with some embodiments.
Figure 13B:
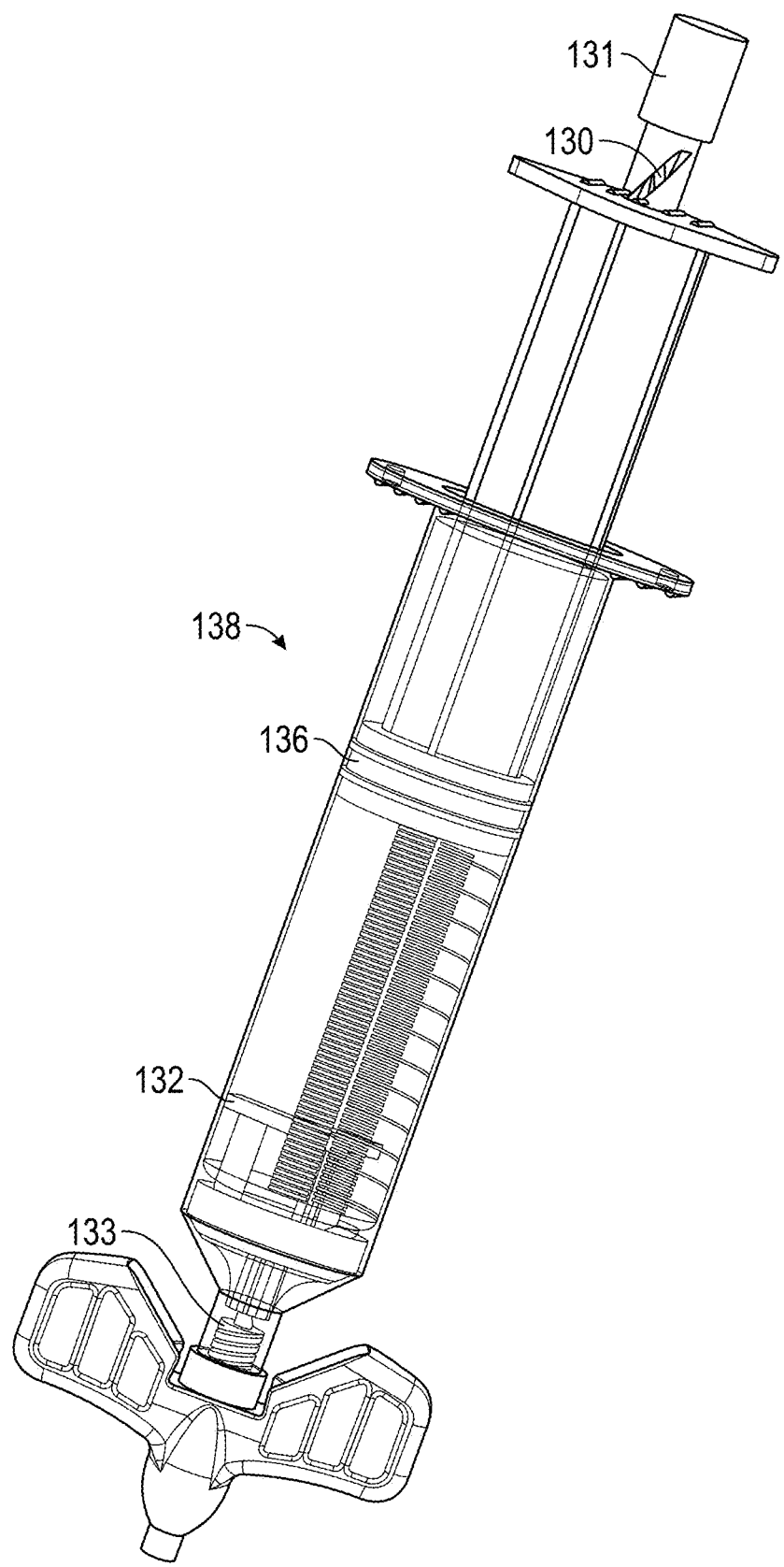
FIG. 13B illustrates a magnified view of portions of the system of FIG. 13A, in accordance with some embodiments.

FIGS. 13A and 13B illustrate a pump 138 with a button 131 on top connected, in a "Yankee screwdriver" style, to a mixing structure 132 at the bottom of the syringe chamber. Pump 138 is illustrated as formed similar to a syringe. For example, as shown in the magnified view of FIG. 13B, a spiral-shaped channel 130 in button 131 engages with at least a portion of pump 138 such that pushing the button 131 causes the mixing structure 132 to rotate, thereby mixing the material (e.g., a fluid and dry bone particles or, alternatively, a bone slurry comprising an already at least partially mixed slurry of fluid and bone particles) at the bottom prior to depressing the plunger 136. When depressed, the plunger 136 advances toward and pushes the mixed bone slurry through the outlet 133 of the pump 138. The pump 138 then forces the bone slurry through the cannula 22 and into the internal cavity 26 of the vertebral body 25.

Figure 14A:
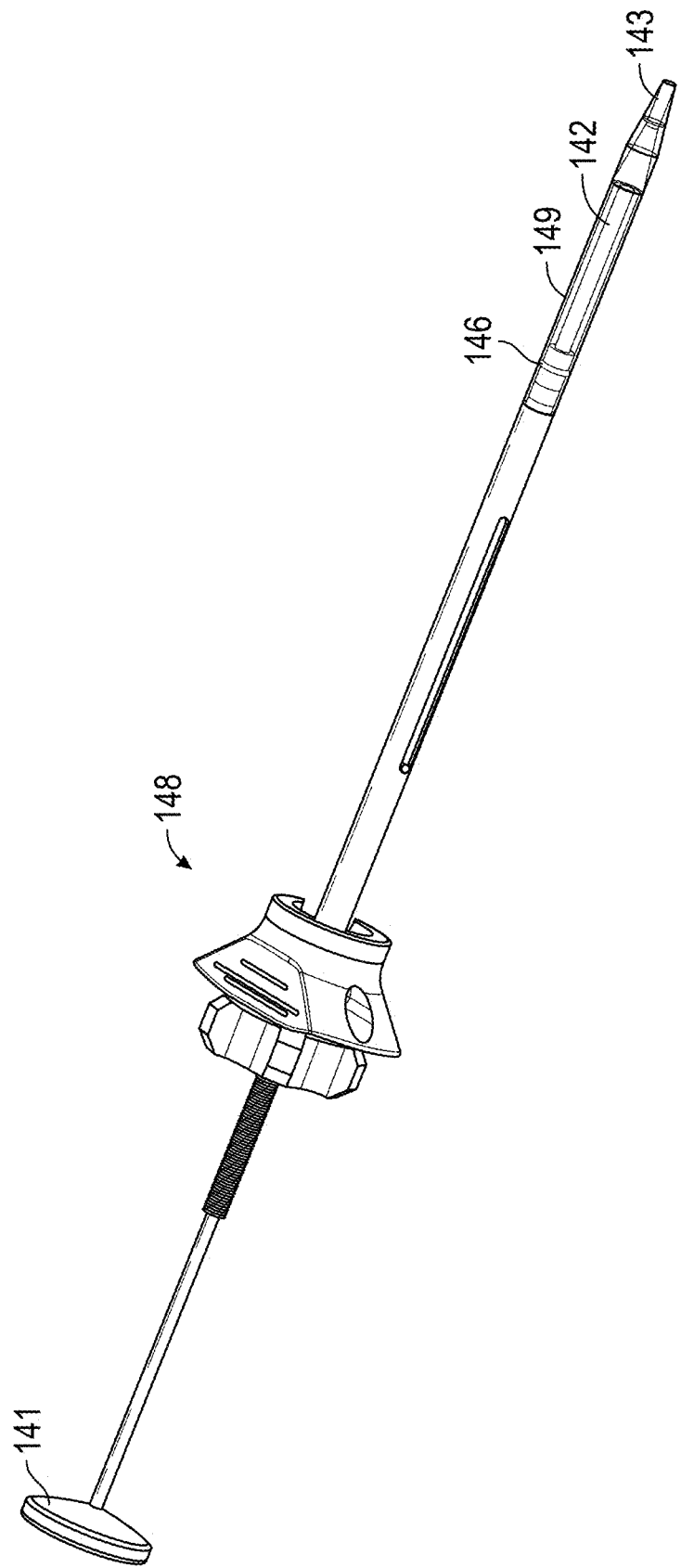
FIG. 14A illustrates yet another system for injecting bone slurry into a bone, in accordance with some embodiments.
Figure 14B:
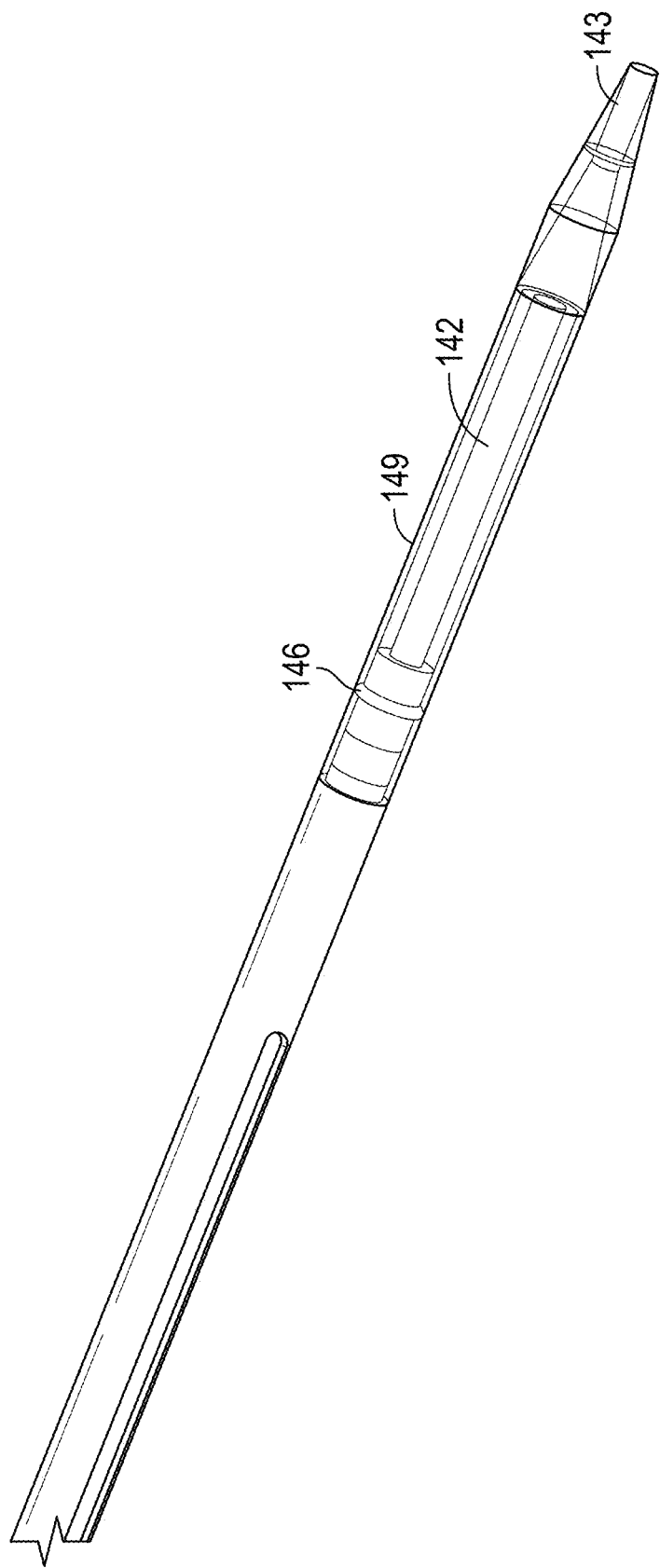
FIG. 14B illustrates a magnified view of portions of the system of FIG. 14A, in accordance with some embodiments.

FIGS. 14A and 14B illustrate an embodiment of a pump 148 comprising a handle 141 coupled to one or both of a thin, central plunger 142 disposed axially along a center of a pump/syringe chamber 149 and a larger plunger 146 disposed proximal of the thin, central plunger 142 with respect to the handle 141. Pushing the handle 141 causes the thin, central plunger 142 to push a small amount of the bone slurry out of a tip or outlet 143 of pump 148 that is narrower than the pump/syringe chamber 149. The larger plunger 146 is configured to push the remaining bone slurry in the chamber 149 down after each injection with the thin, central plunger 112. Accordingly, the pump 138 forces the bone slurry through the cannula 22 and into the internal cavity 26 of the vertebral body 25 (not shown in FIGS. 14A, 14B).

FIGS. 15 through 36 illustrate stages of a vertebroplasty procedure, in accordance with some embodiments. While one or more embodiments are described below, it is appreciated that such a procedure can also be performed utilizing any apparatus or system described in this disclosure without limitation.

Figure 15:
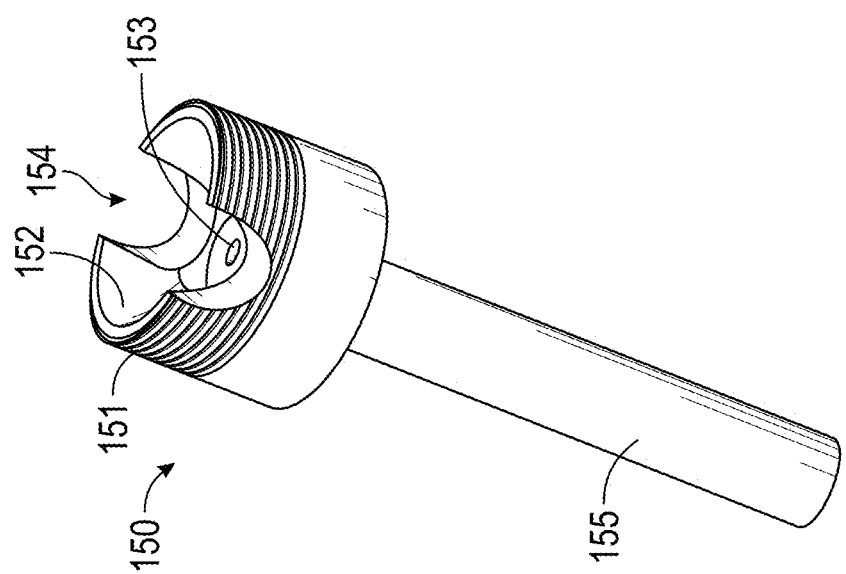
FIG. 15 illustrates a bone cartridge holder for filling a cartridge with bone particles, in accordance with some embodiments.

FIG. 15 illustrates a bone cartridge holder 150 for filling a cartridge 160 with bone particles, in accordance with some embodiments. In some embodiments, bone cartridge holder 150 includes an upper threaded portion 151 and a lower cylindrical portion 155. In some embodiments, upper threaded portion 151 has a larger diameter than the lower cylindrical portion 155. In some embodiments, upper threaded portion 151 comprises a beveled upper surface 152 that recesses toward the lower cylindrical portion 155, and a lumen 153 extending from a center of the beveled upper surface 152 through a center of lower cylindrical portion 155. Bone cartridge holder 150 is configured to receive cartridge 160 (see at least FIG. 16) in lumen 153 such that at least an upper portion of cartridge 160 rests within and against the beveled upper surface 152 of upper threaded portion 151. Upper threaded portion 151 may additionally have transversely-formed tabular recesses 154 that provide a space for grasping the upper portion of cartridge 160 to remove it from cartridge holder 150.

Figure 16:
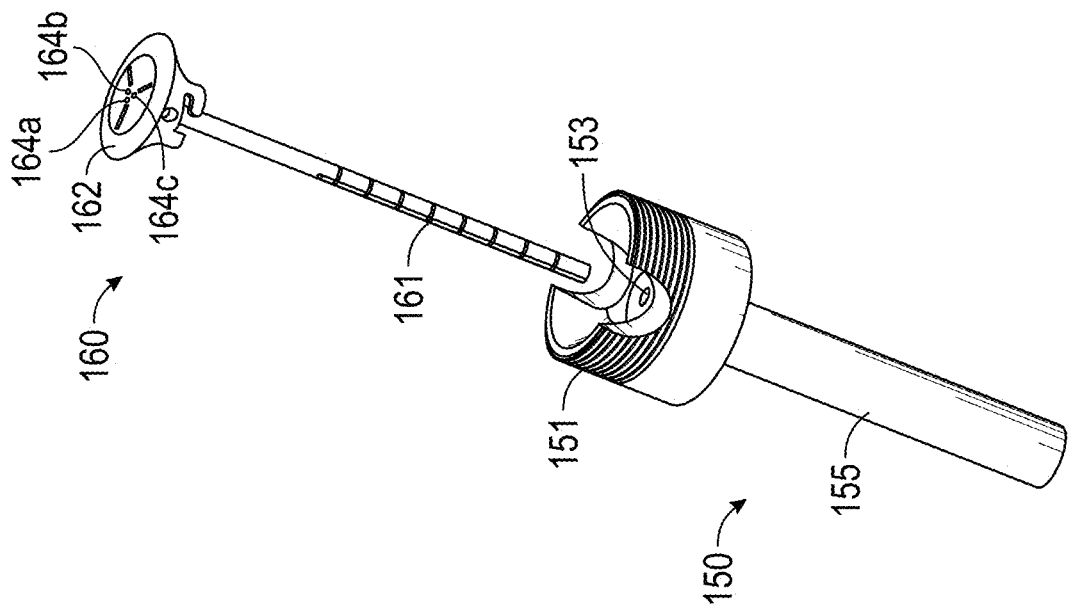
FIG. 16 illustrates the bone cartridge holder of FIG. 15 and a cartridge configured to hold bone particles, in accordance with some embodiments.
Figure 17:
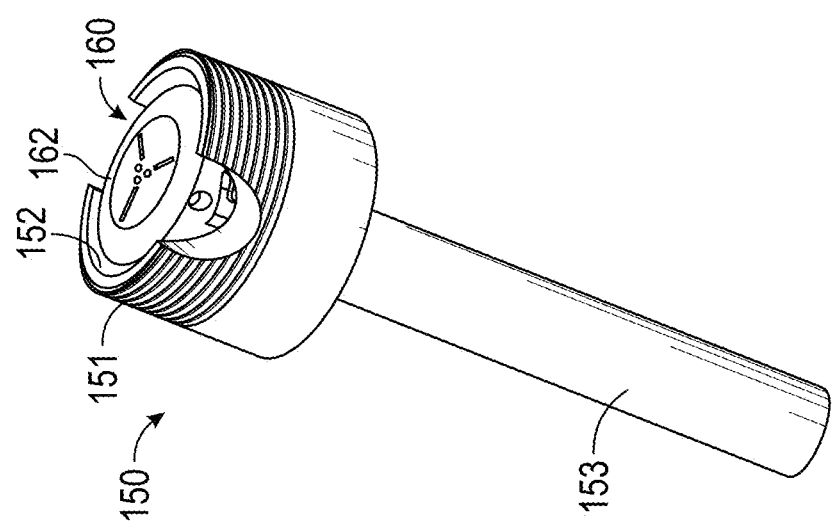
FIG. 17 illustrates the cartridge of FIG. 16 disposed within the bone cartridge holder of FIG. 15, in accordance with some embodiments.

FIG. 16 illustrates cartridge 160 disposed over bone cartridge holder 150, in accordance with some embodiments. As illustrated, cartridge 160 includes an upper portion 162 having a plurality of lumens or barrels 164a-164c that extend through a shaft 161 and that are configured to receive bone particles. In some embodiments, at least a part of upper portion 162 of cartridge 160 can have a shape that is complementary to the beveled upper surface 152 of cartridge holder 150 such that, when cartridge 160 is inserted into cartridge holder 150, shaft 161 extends into lumen 153 and upper portion 162 is seated on beveled upper surface 152 of threaded upper portion 151 of cartridge holder 150, as illustrated in FIG. 17.

Figure 18:
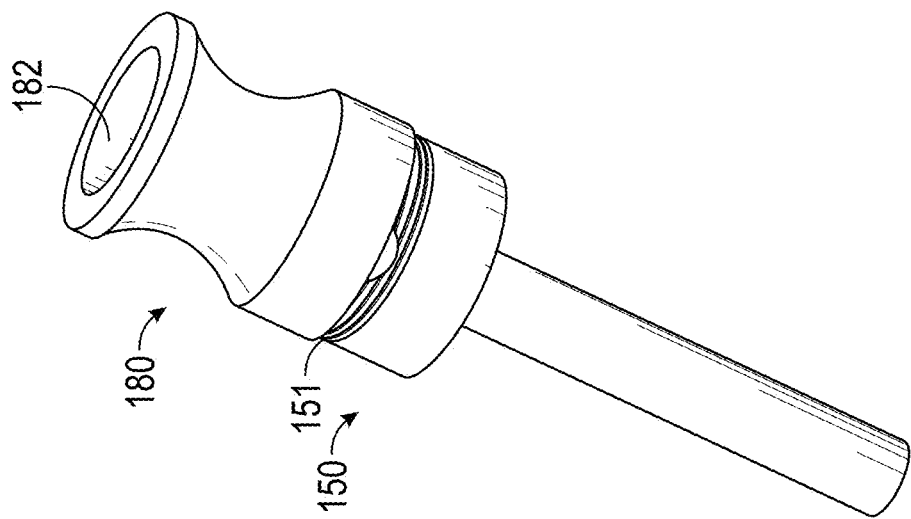
FIG. 18 illustrates the assembled bone cartridge holder and bone cartridge of FIG. 17 and a hollow filling cap disposed thereon, in accordance with some embodiments.
Figure 19:
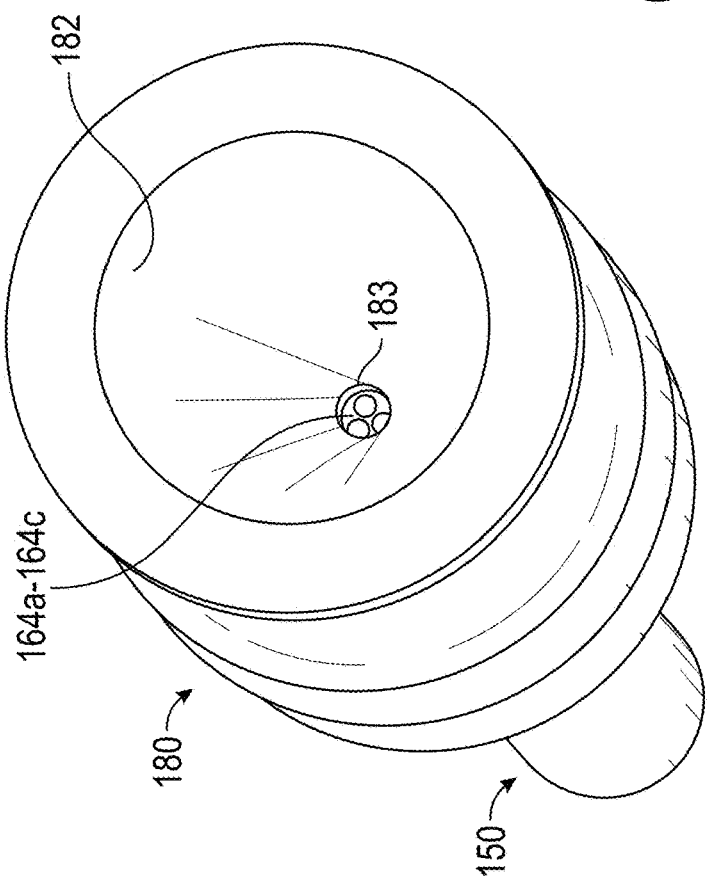
FIG. 19 illustrates the assembly of FIG. 18 from a different angle which shows the exposed openings for the barrels of the cartridge through the bottom of the hollow filling cap, in accordance with some embodiments.

In FIG. 18 a hollow cap 180 is placed on the holder 150, which is loaded with cartridge 160 (not visible in FIG. 18). For example, hollow cap 180 can include threads (not visible in FIG. 18) configured to mate with upper threaded portion 151 of cartridge holder 150. Hollow cap 180 can also include a beveled upper surface 182 that recesses toward a center of hollow cap 180 and that is configured to hold bone particles for loading into cartridge 160. A hole 183 in the central bottom of beveled upper surface 182 exposes the plurality of barrels 164a-164c of cartridge 160 when hollow cap 180 is properly disposed on holder 150. FIG. 19 illustrates a view of hollow cap 180 where barrels 164a-164c in cartridge 160 are visible.

Figure 20:
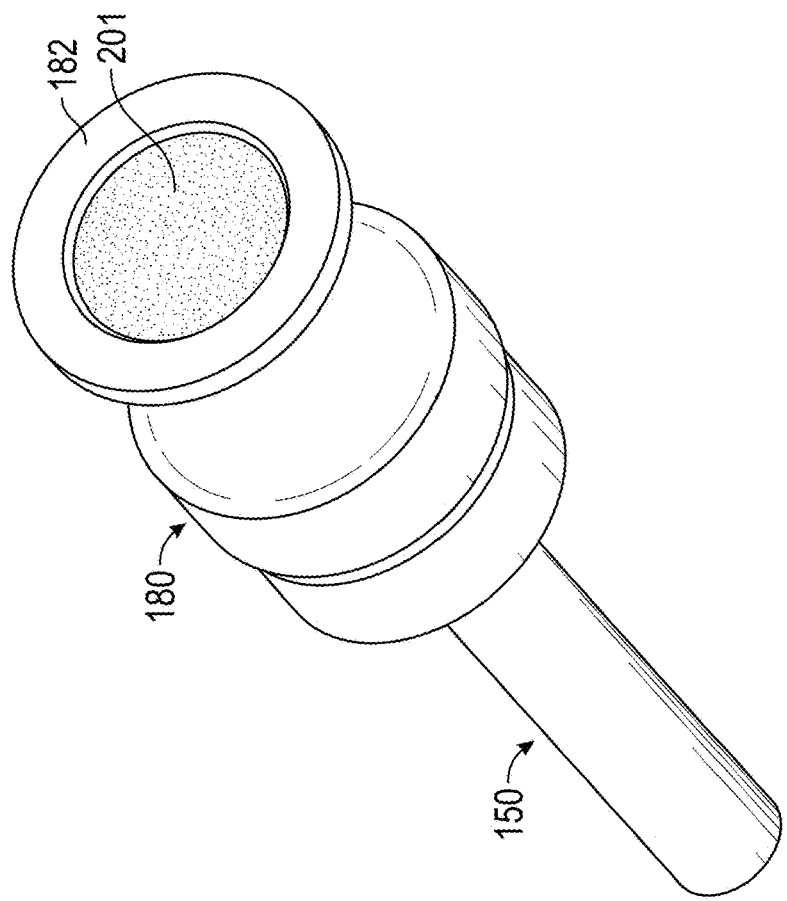
FIG. 20 illustrates the assembly of FIG. 19 further comprising bone particles disposed in the hollow filling cap, in accordance with some embodiments.

In some embodiments, a mix of cortical and cancellous bone particles can be loaded into hollow cap 180. FIG. 20 illustrates the assembly of FIG. 19 further comprising bone particles 201 disposed in hollow cap 180, in accordance with some embodiments.

Figure 21:
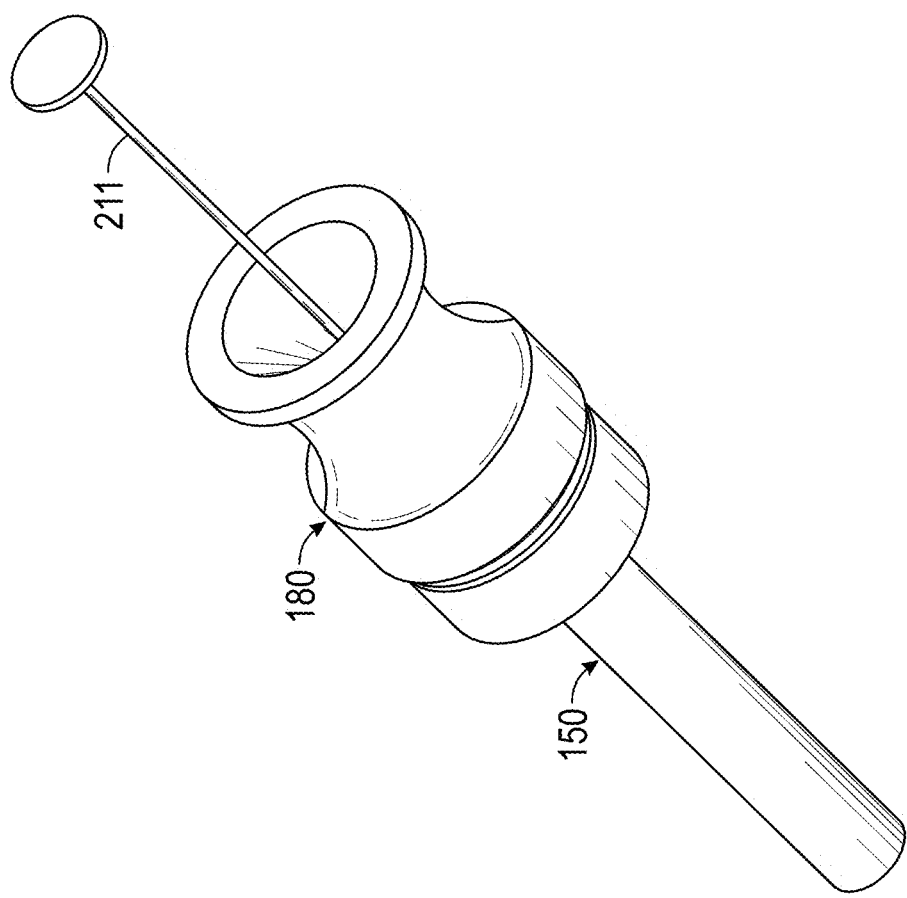
FIG. 21 illustrates the assembly of FIG. 20 and a tamp configured to push the bone particles from the hollow filling cap into barrels of the cartridge through the exposed openings, in accordance with some embodiments.

In FIG. 21, a tamp or plunger 211 is used to push the bone particles 201 into the barrels 164a-164c of cartridge 160. Accordingly, in some embodiments, tamp 211 can have an outer diameter that is slightly smaller than an inner diameter of barrels 164a-164c of cartridge 160.

Figure 22:
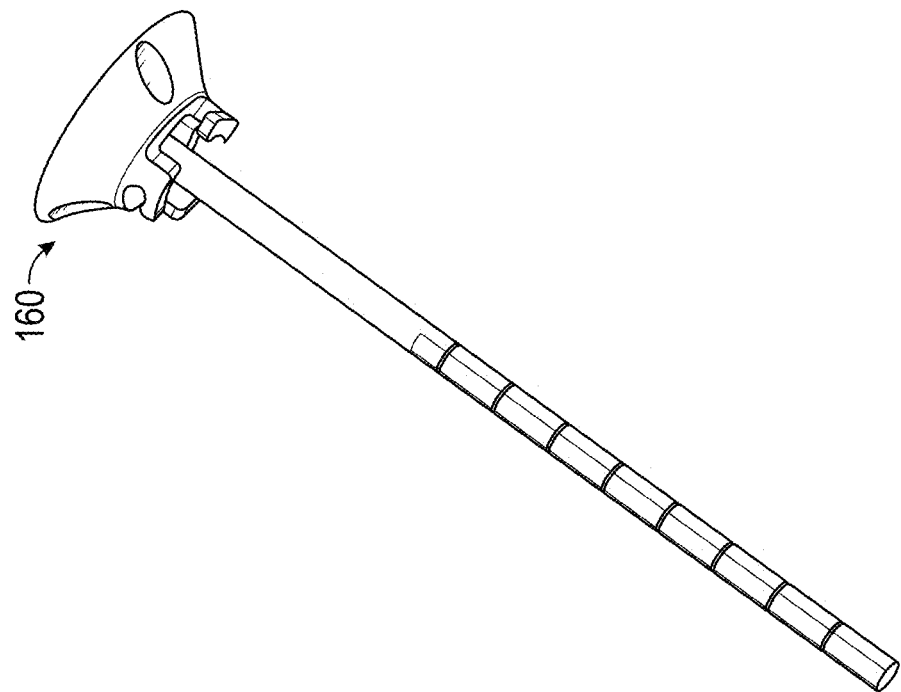
FIG. 22 illustrates the cartridge with its barrels filled with bone particles, in accordance with some embodiments.

Once filled with bone particles, hollow cap 180 and then cartridge 160 can be removed from cartridge holder 150. FIG. 22 illustrates cartridge 160 with its barrels 164a-164c filled with bone particles 201, in accordance with some embodiments. FIG. 23 illustrates a magnified portion of cartridge 160 showing bone particles 201 disposed in barrels 164a-164c, in accordance with some embodiments.

Figure 24:
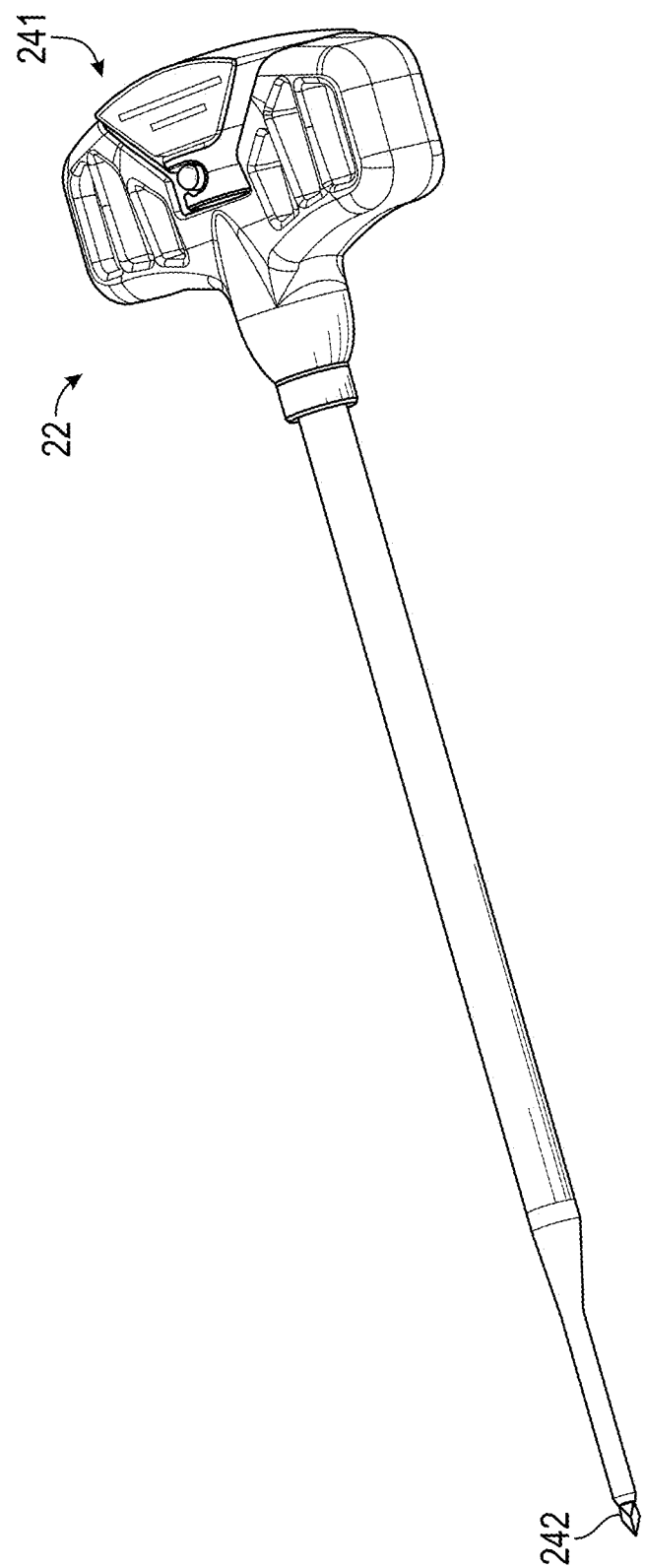
FIG. 24 illustrates installation of a stylet into a cannula for insertion into a vertebral body, in accordance with some embodiments.
Figure 25:
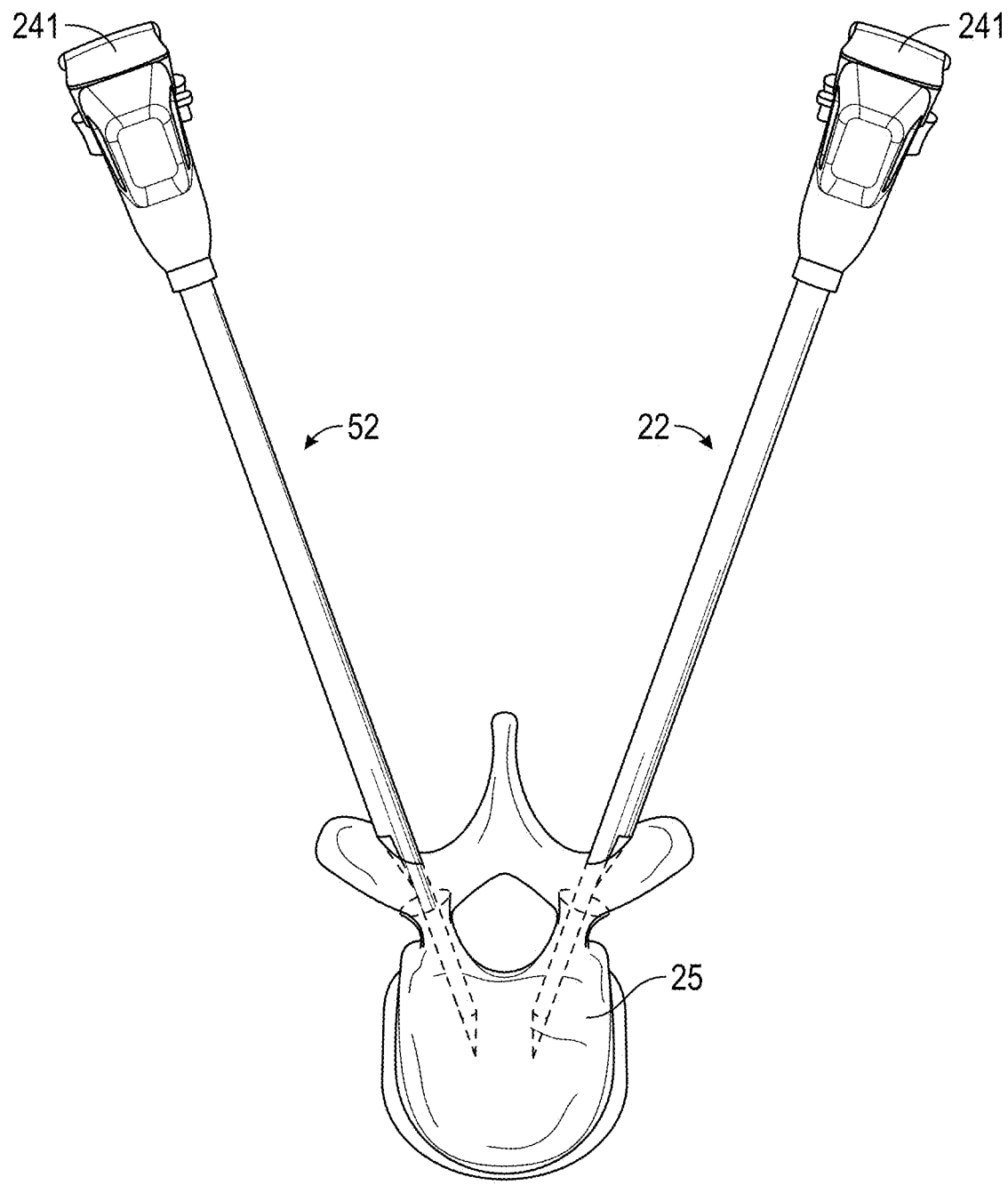
FIG. 25 illustrates the insertion of distal ends of two cannulas, having respective stylets installed therein, into a vertebral body, in accordance with some embodiments.
Figure 26:
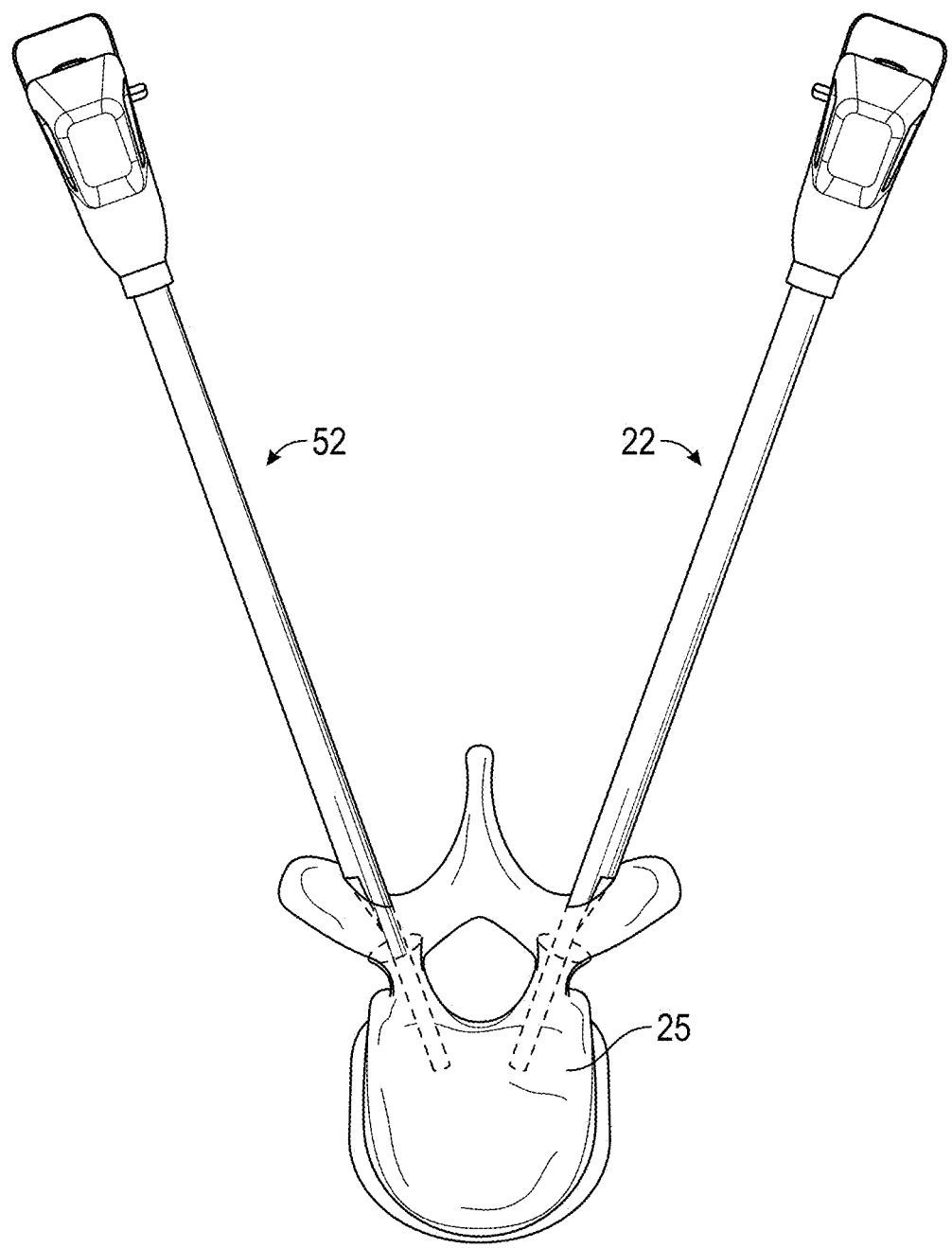
FIG. 26 illustrates the distal ends of the cannulas of FIG. 25 disposed in the vertebral body with the respective stylets removed, in accordance with some embodiments.

FIG. 24 illustrates installation of a stylet or other sharp or needle-like tool 241 into cannula 22 such that a sharp end 242 of stylet 241 protrudes from a distal end of cannula 22. FIG. 25 illustrates disposing the cannula 22 and stylet 241 of FIG. 24 and another similarly arranged cannula 52 and stylet 241 such that distal ends of cannulas 22, 52 protrude into vertebral body 25, thereby forming respective openings to a central portion of vertebral body 25. As previously described, openings into vertebral body 25 can be formed utilizing sharp end 242 of stylet 241 and/or a bone drill, for example. FIG. 26 illustrates removal of stylets 241 from each of cannulas 22, 52, while the distal ends of cannulas 22, 52 remain disposed within vertebral body 25.

Figure 27:
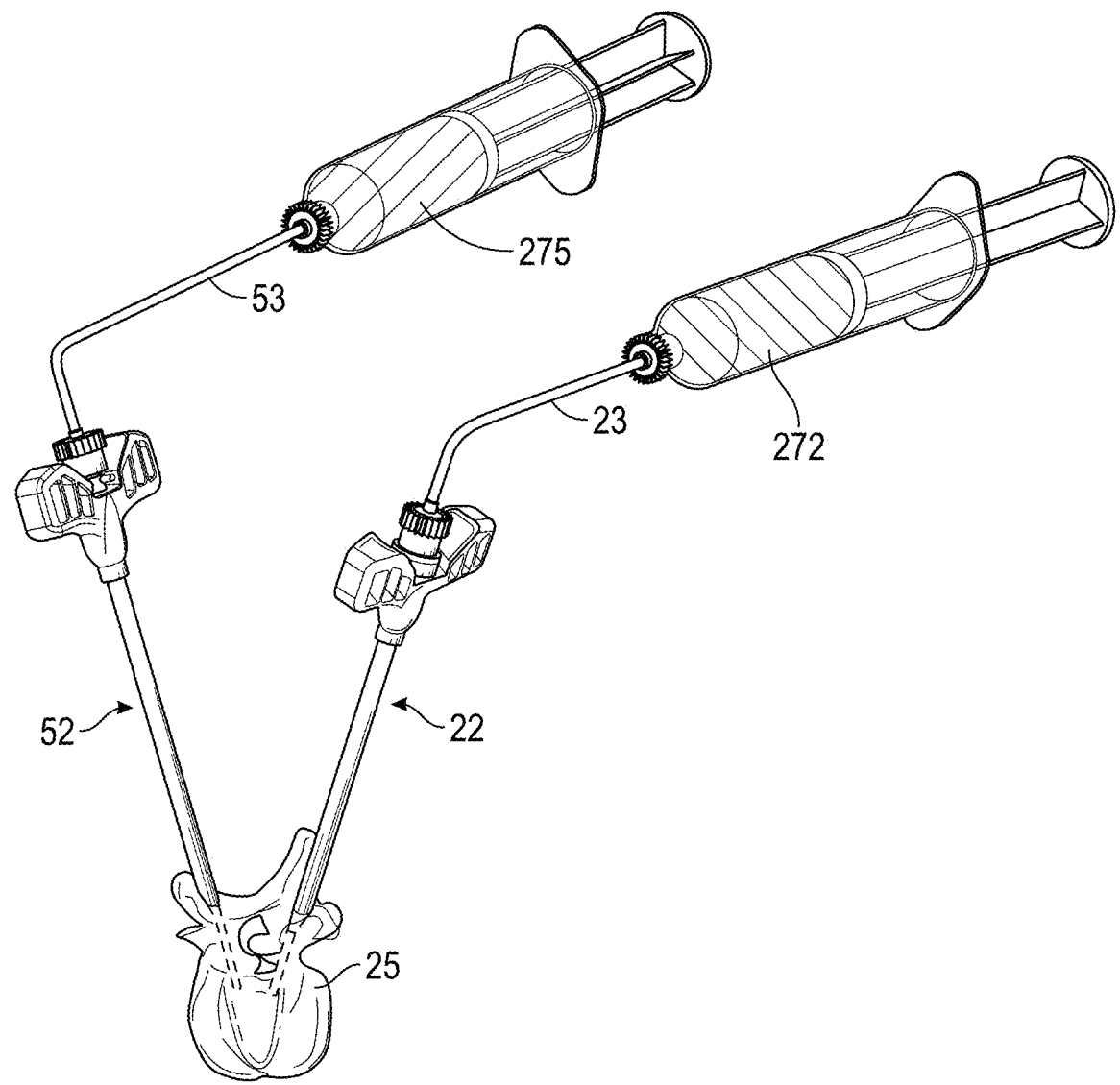
FIG. 27 illustrates aspiration of the interior of a vertebral body, according to some embodiments.

FIG. 27 illustrates aspiration of the interior of the vertebral body 25, according to some embodiments. For example, catheters 23, 53 may be installed into respective cannulas 22, 52 and coupled to respective aspirating devices 272, 275. In some embodiments, aspirating devices 272, 275 can comprise syringe-like devices, pump-like devices, or any other type of device configured to remove material, e.g., fluid and/or bone, from inside vertebral body 25 and/or pump material, e.g., fluid and/or bone, into vertebral body 25 through catheters 23, 53.

Figure 28:
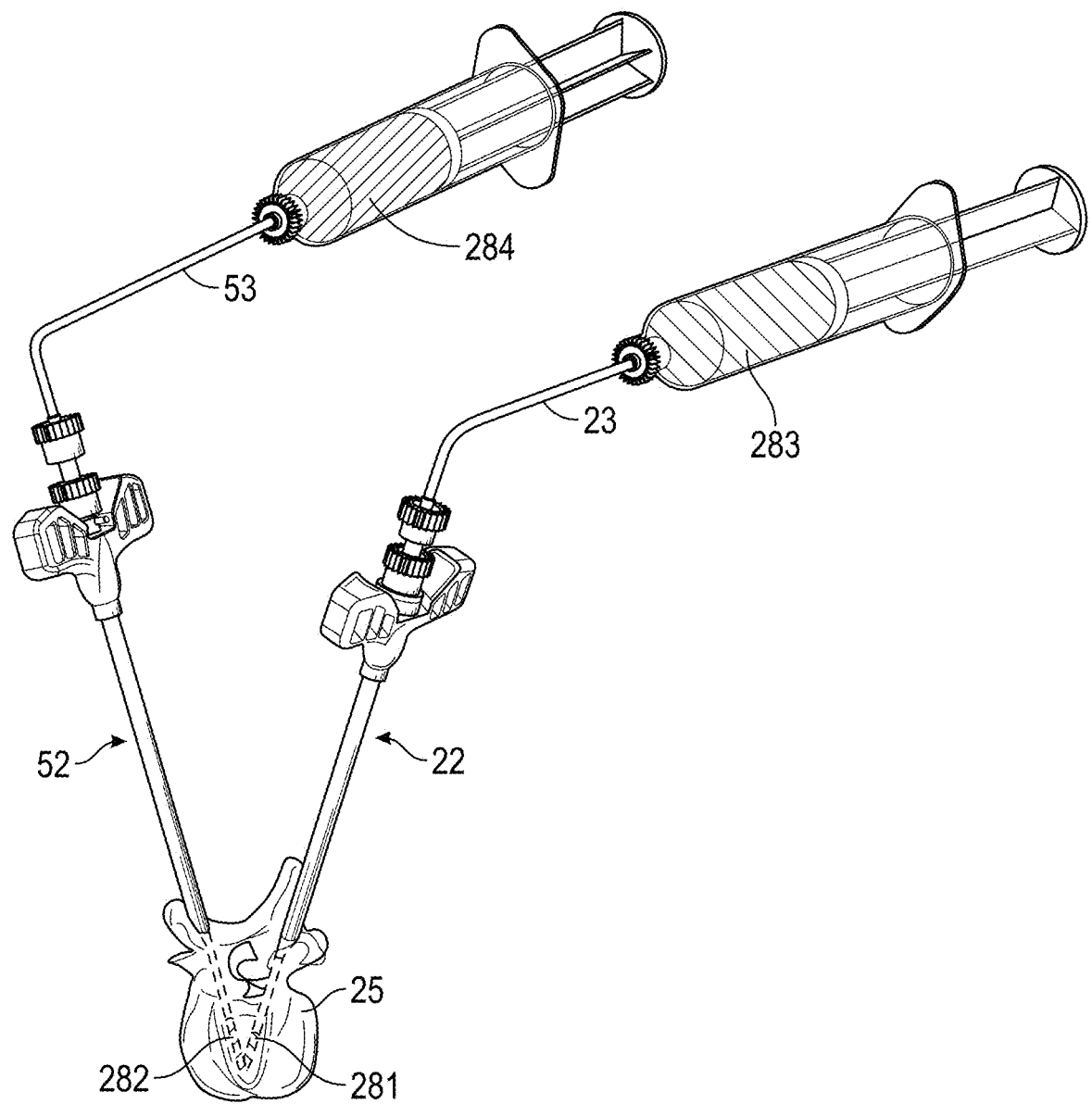
FIG. 28 illustrates deployment of kyphoplasty balloons into an interior cavity of a vertebral body through respective cannulas, according to some embodiments.

FIG. 28 illustrates deployment of kyphoplasty balloons 281, 282 through respective cannulas 22, 52, according to some embodiments. For example, kyphoplasty balloon 281 may be attached to one end of catheter 23 and an inflating device 283 may be attached to the other end of catheter 23. Similarly, in some embodiments, kyphoplasty balloon 282 may be attached to one end of catheter 53 and an inflating device 284 may be attached to the other end of catheter 53. In some embodiments, inflating devices 283, 284 can comprise syringe-like devices, pump-like devices, or any other type of devices configured to pump fluid into kyphoplasty balloons 281, 282 through catheters 23, 53.

Figure 29:
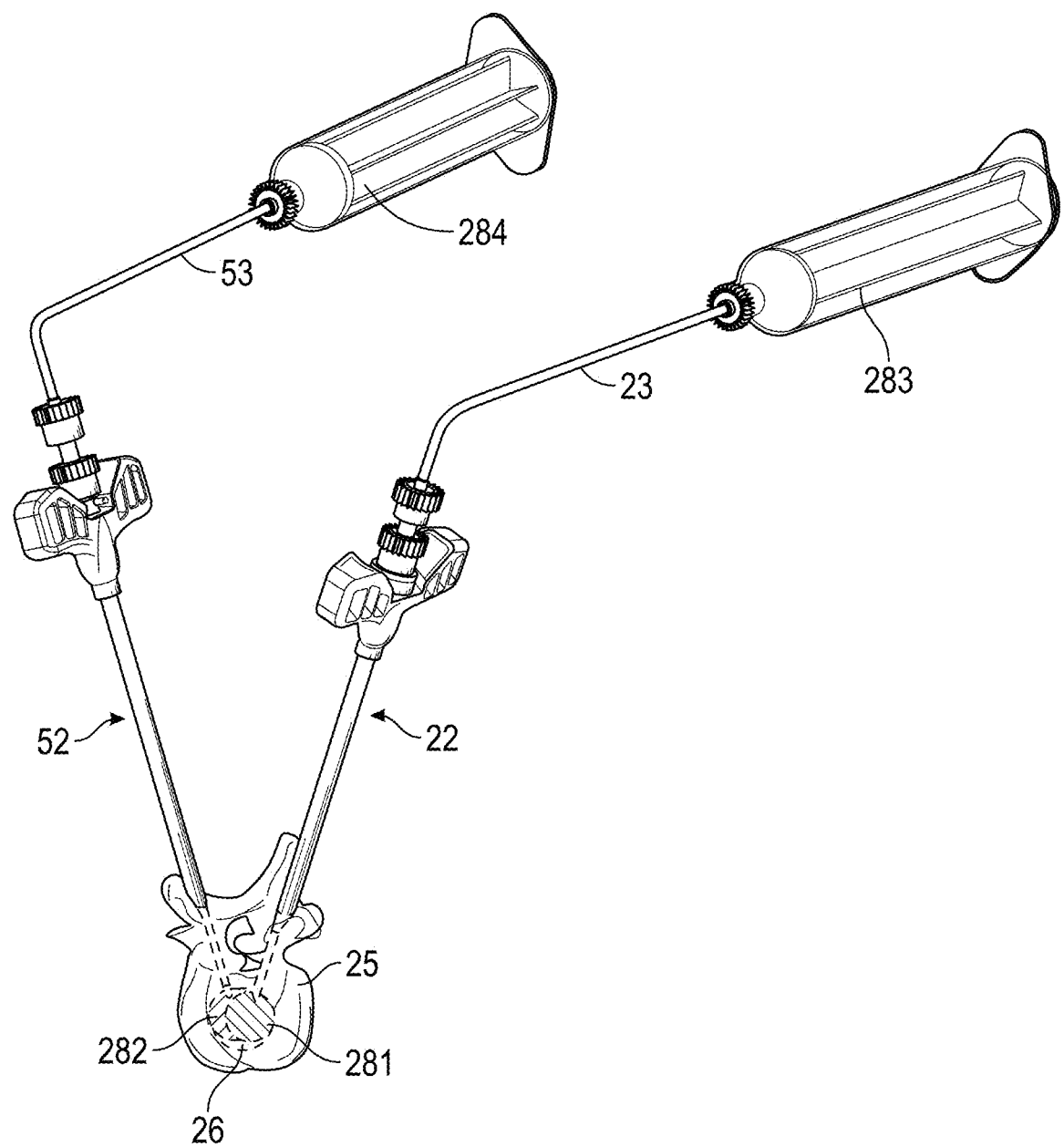
FIG. 29 illustrates the kyphoplasty balloons of FIG. 29 in their inflated states within the vertebral body, according to some embodiments.

FIG. 29 illustrates kyphoplasty balloons 281, 282 in their inflated states within vertebral body 25, according to some embodiments. As illustrated, inflating one or both of kyphoplasty balloons 281, 282 helps to create internal cavity 26 in vertebral body 25.

Figure 30:
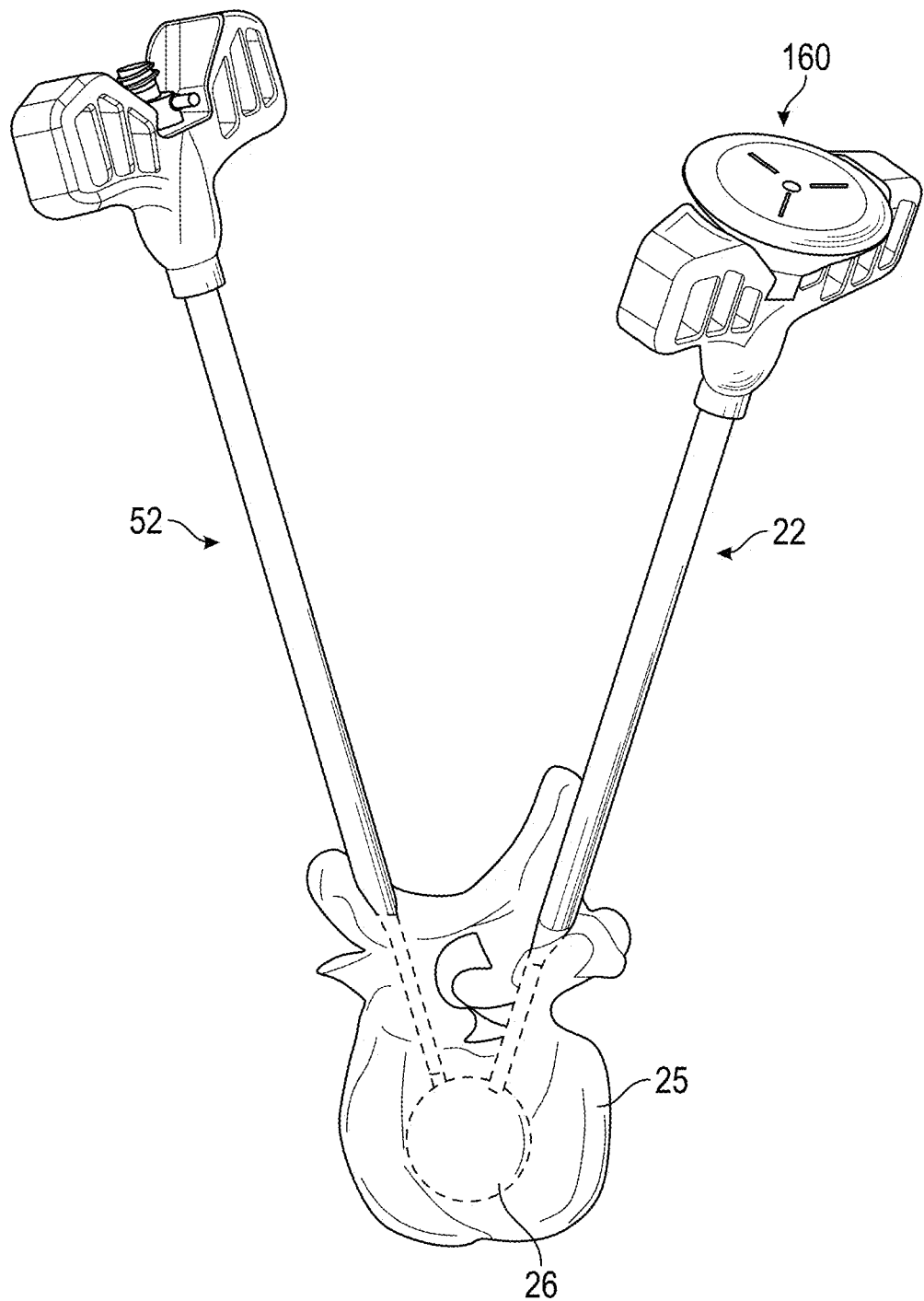
FIG. 30 illustrates insertion of a loaded bone particle cartridge into a cannula, according to some embodiments.
Figure 31:
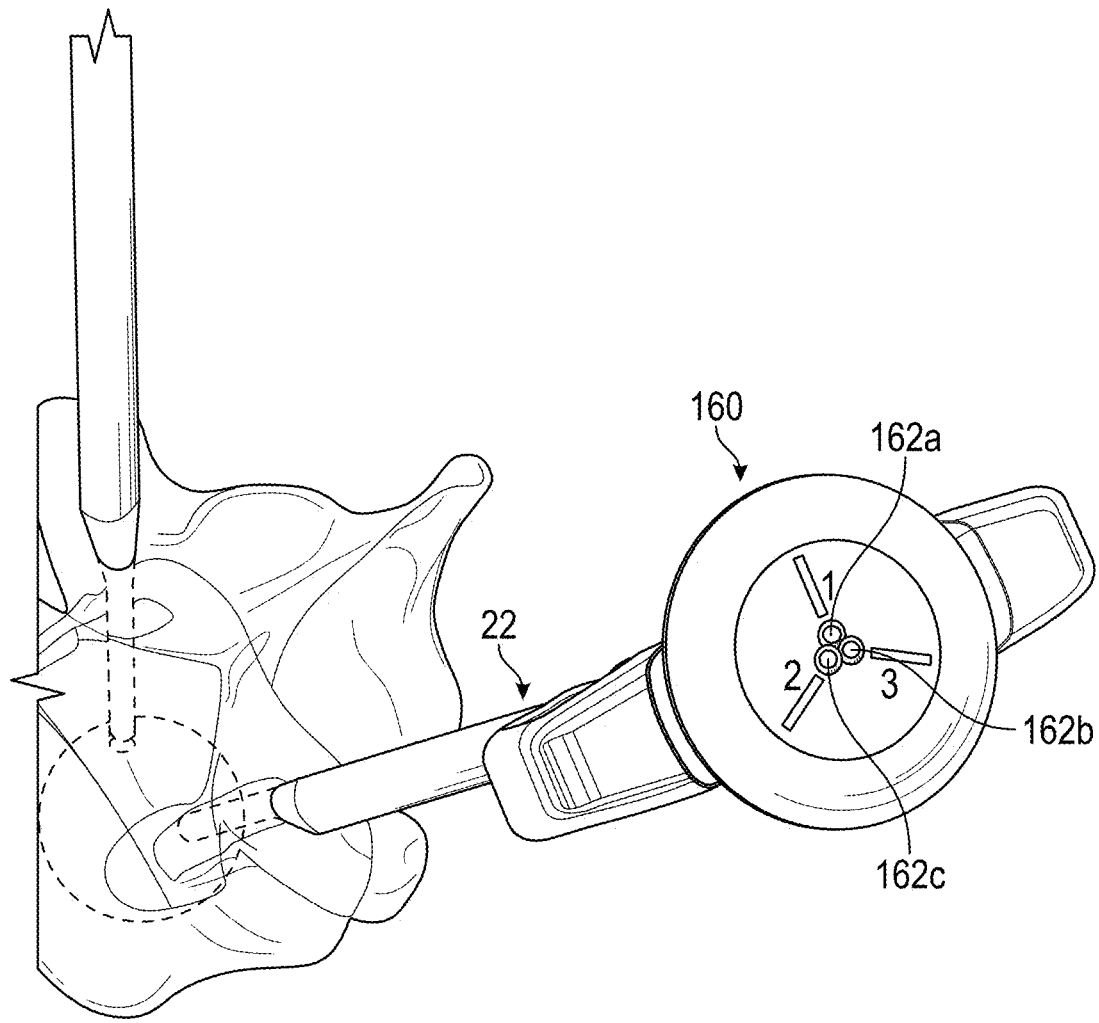
FIG. 31 illustrates another view of the cartridge of FIG. 31 in which the plurality of barrels loaded with bone particles are visible, according to some embodiments.

FIG. 30 illustrates insertion of cartridge 160, loaded with bone particles, into cannula 22, according to some embodiments. For example, shaft 161 of cartridge 160 is disposed within cannula 22 and upper portion 162 of cartridge 160 rests against a proximal end of cannula 22. FIG. 31 illustrates another view of cartridge 160 inserted in cannula 22 in which the plurality of barrels 162a-162c are visible, according to some embodiments.

Figure 32:
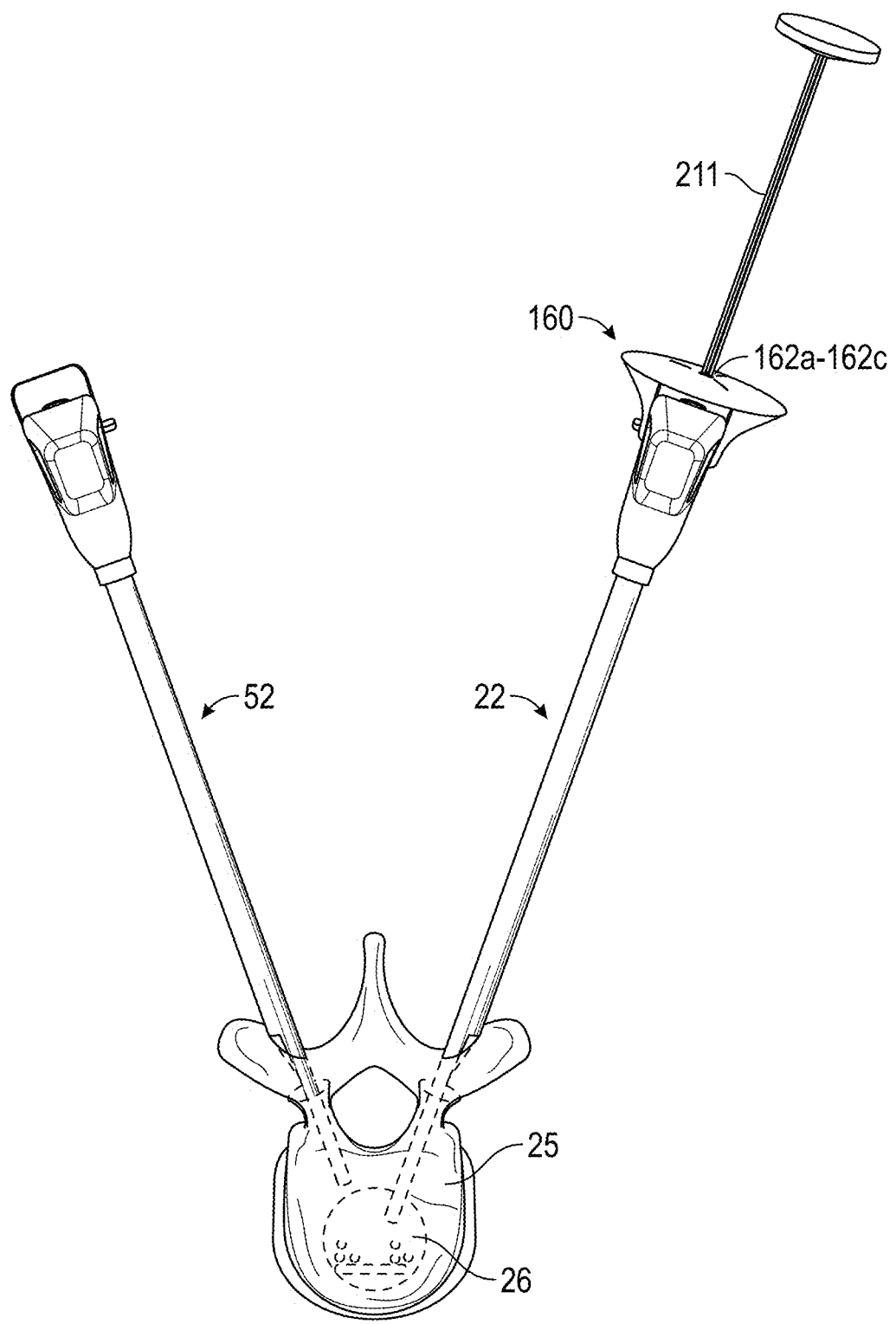
FIG. 32 illustrates utilization of a bone tamp to inject bone particles from one or more of the plurality of barrels of FIG. 31 into the interior cavity of the vertebral body through the cannula, in accordance with some embodiments.
Figure 33:
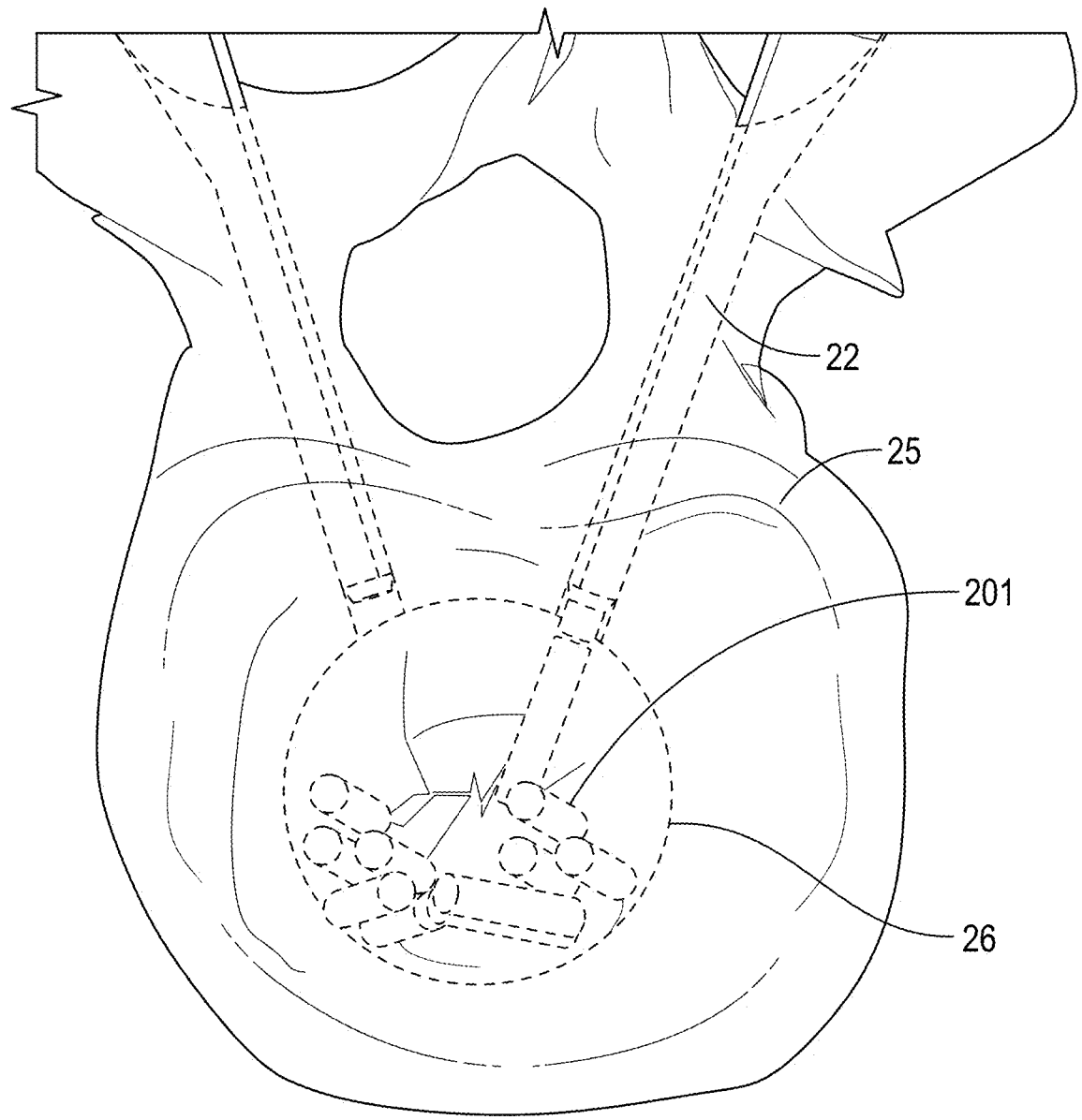
FIG. 33 illustrates a magnified portion of FIG. 32 showing the bone particles being injected into the interior cavity of the vertebral body, in accordance with some embodiments.

FIG. 32 illustrates utilization of bone tamp or plunger 211, pushed down into one or more of the plurality of barrels 162a-162c, to inject bone particles into 201 interior cavity 26 of vertebral body 25 through cannula 22, in accordance with some embodiments. In some embodiments, cartridge 160, with or without bone tamp 211, may comprise or also be referred to as a bone particle pump, since it is configured to deliver bone particles 201 into interior cavity 26. FIG. 33 illustrates a magnified portion of FIG. 32 showing bone particles 201 being injected into interior cavity 26 of vertebral body 25, in accordance with some embodiments.

While bone particles 201 are illustrated in FIGS. 30-34, the present disclosure is not so limited and a bone slurry or bone pellets, according to any embodiments of this disclosure, may also or alternatively be injected into interior cavity 26 of vertebral body 25 substantially as shown here, or anywhere else in this disclosure, utilizing any bone particle, pellet, and/or slurry injecting gun, device or pump described within the present disclosure.

Figure 34:
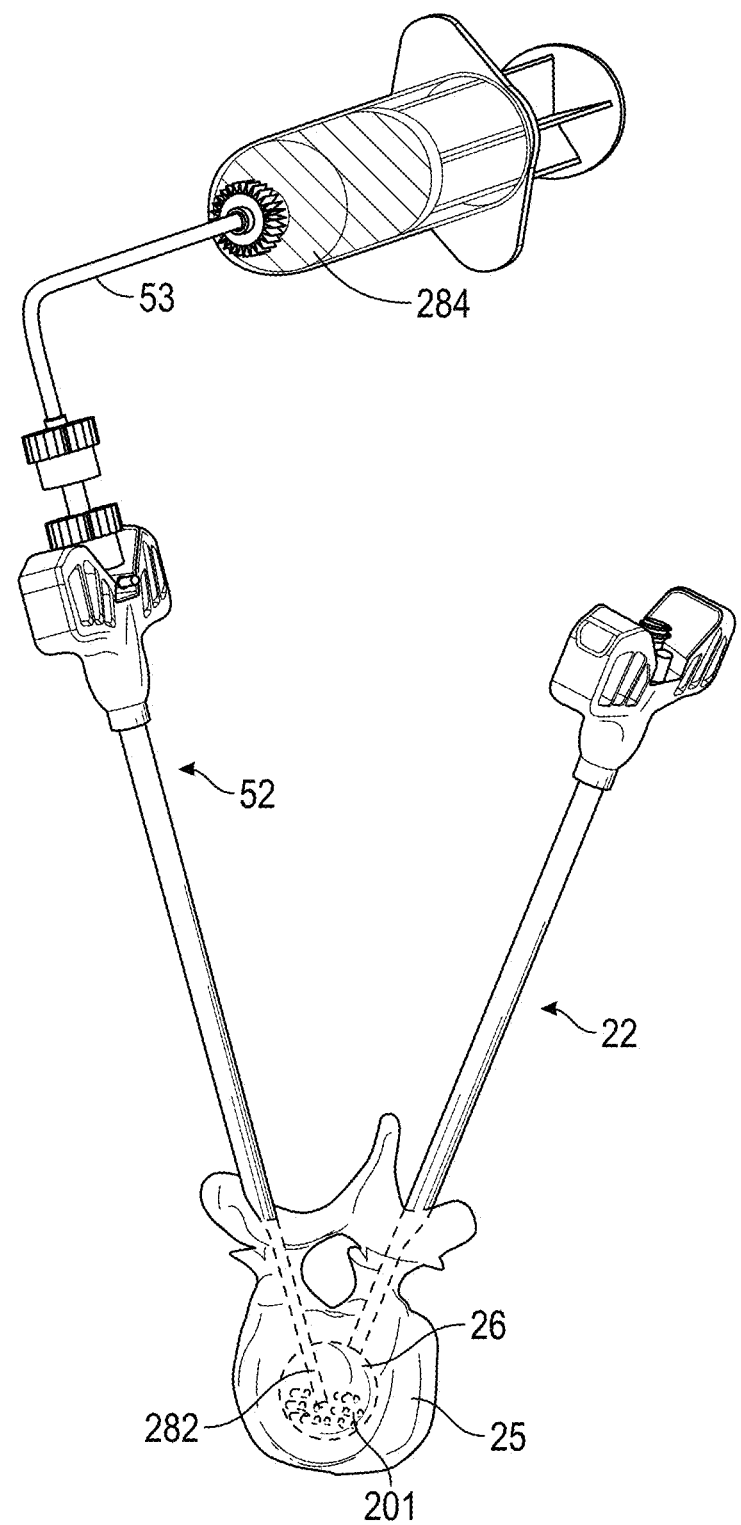
FIG. 34 illustrates application of balloon kyphoplasty and aspiration to pack the bone particles into the internal cavity of the vertebral body, in accordance with some embodiments.

FIG. 34 illustrates application of balloon kyphoplasty and aspiration to pack bone particles 201 into internal cavity 26 of vertebral body 25, in accordance with some embodiments. For example, kyphoplasty balloon 282 may be attached to one end of catheter 53 and inflating device 284 may be attached to the other end of catheter 53. Kyphoplasty balloon 282 is then fed through cannula 52, into interior cavity 26 of vertebral body 25, and inflated. Inflation of kyphoplasty balloon 282 crushes bone particles 201 and packs them tightly against the sides of interior cavity, as illustrated in FIG. 35 for example.

Figure 35:
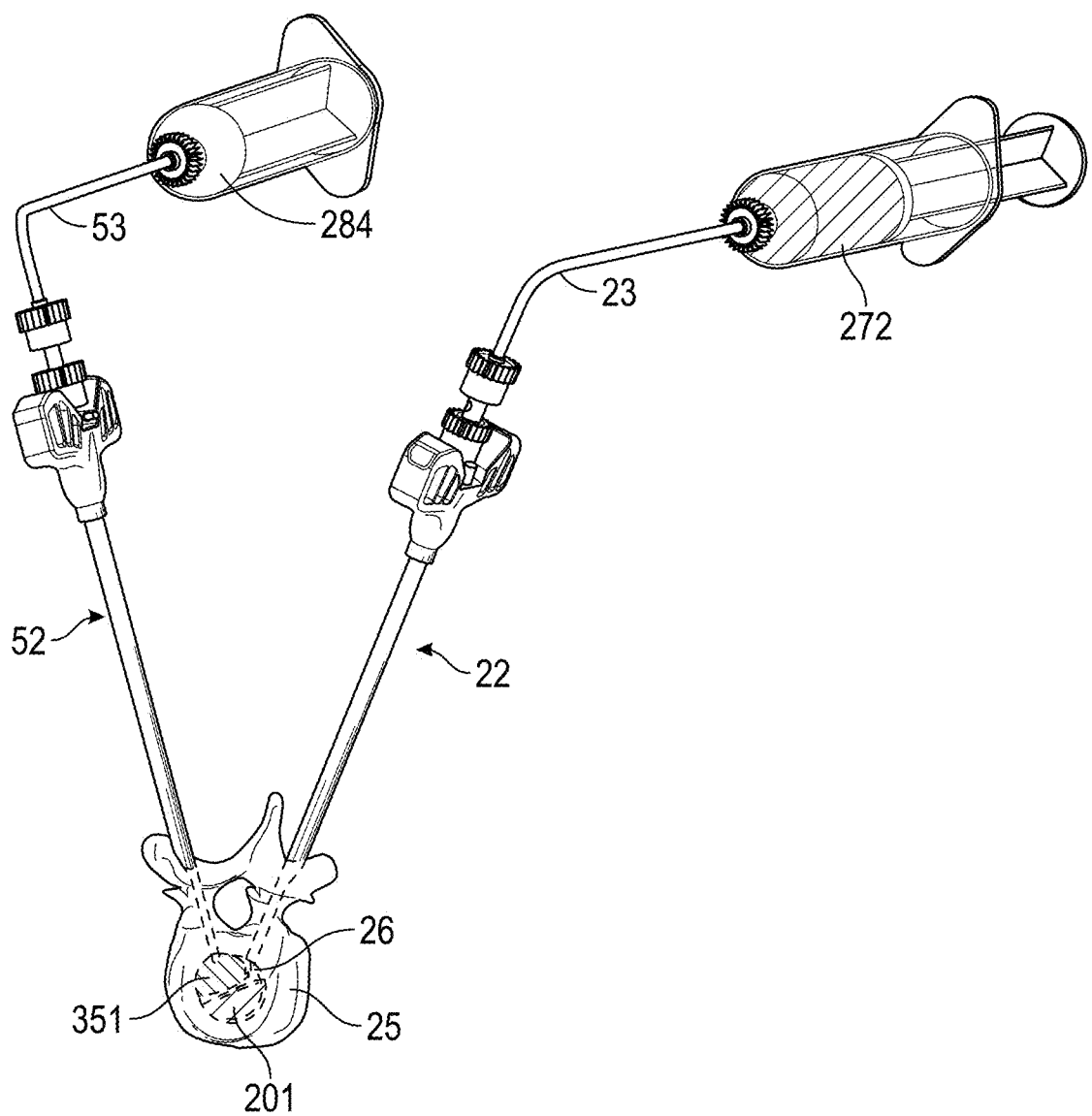
FIG. 35 illustrates inflation of the kyphoplasty balloon of FIG. 34 and aspiration of the interior cavity of the vertebral body, according to some embodiments.

FIG. 35 illustrates inflation of kyphoplasty balloon 282 and aspiration of interior cavity 26 of vertebral body 25, according to some embodiments. For example, inflating device 284 pumps fluid into kyphoplasty balloon 282, inflating it. Catheter 23 may be installed into cannula 22 and coupled to aspirating device 272. Aspirating device 272 can be configured to generate suction that aspirates interior cavity 26 of vertebral body 25 through catheter 23 disposed through cannula 22. This balloon kyphoplasty may be repeated with aspiration as desired to crush bone particles 201 against the cavity walls. And bone particle injection followed by kyphoplasty and, in some cases aspiration as describe above, may be repeated multiple times.

Figure 36:
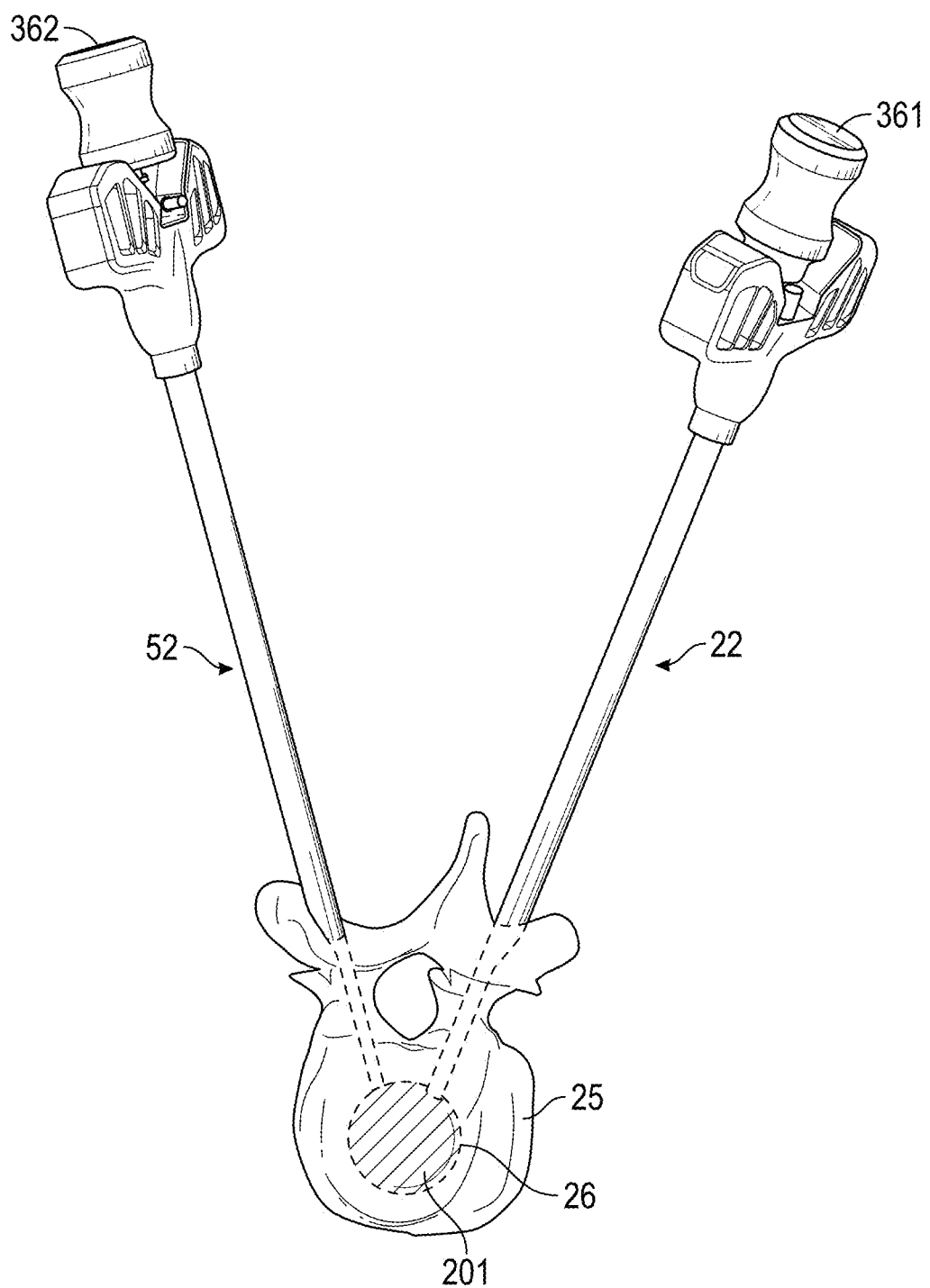
FIG. 36 illustrates application of manual tamping to clear any remaining bone particles from the cannulas as previously described in connection with at least any of FIGS. 15-35, in accordance with some embodiments.

FIG. 36 illustrates application of manual tamping to clear any remaining bone particles from cannulas 23, 53, in accordance with some embodiments. For example, catheters 23, 53 may be removed from cannulas 22, 52 and manual tampers 361, 362 may be inserted into cannulas 22, 52, respectively. Such insertion causes manual tampers 361, 362 to clear any remaining bone particles 201 from cannulas 23, 53.

In some embodiments, one or both of cannulas 22, 52 or stylets 241 may also or alternatively have a distraction device configured to create interior cavity 26 within vertebral body 25, if need be. However, with gradual pressurization and movement of stylets 241 in multiple directions, such cavitation may not be necessary. Such cavitation if performed, can be carried out utilizing a spring within the stylet sheath to expand the stylet in multiple directions, utilizing a kyphoplasty balloon to expand the fractured vertebra cancellous bone, or utilizing a cortical cap that can be placed onto the shaft of the stylet or the cannula that can be used to distract the endplates that have fractured and fill in the bone interstices with cortical allograft or autologous microspheres. This cortical bone cap may be disposed on the stylet or the cannula and can be deployed with spring loaded compression to push the endplates back into normal position. This would be the first time that bone would be utilized to distract the compressed vertebra and allow the microspheres to maintain its height and eventually allow the vertebral body to heal. This method of incremental bone impaction can also be utilized at the cephalad or caudal end of a surgical construct such as a posterolateral instrumented fusion to prevent proximal junctional kyphosis or minimize fracture of the sacrum, ileum or lower lumbar spine or any bone.

In the above described specific implementation, there may be a separate slurry injection catheter that is inserted into the vertebral body through a cannula placed in the access opening to the inside of the vertebral body. It will be appreciated that it would also be possible to use the cannula directly as an injection and/or aspiration path without using a separate catheter within a cannula, combining the functions of both described above, for any embodiment(s), into one element.

In some implementations, the bone particle slurry may additionally contain particles of material other than bone. For example, these non-bone particles incorporated into the bone particle slurry may comprise metal particles such as titanium particles or polymer particles such as PMMA particles, or any mixture of non-bone particles of different types. In some implementations, these non-bone particles may be of relatively small size, such as having a characteristic size of less than 100 micrometers, less than 50 micrometers, or less than 20 micrometers. In these implementations, multiple non-bone particles can become incorporated into the voids, as illustrated in FIG. 4. In some implementations, such a slurry may be "gap graded" where there are bone particles having a relatively narrow range of large characteristic sizes, and non-bone particles having a relatively narrow range of much smaller characteristic sizes. For example, the mean characteristic size of the smallest 10% of the bone particles in the slurry may be at least five time larger than the mean characteristic size of the largest 10% of the non-bone particles. In these implementations, the non-bone particles can be configured to elute therapeutic substances such as chemotherapy drugs, antibiotics, or the like. Some or all of the non-bone particles may be resorbable. Such a mixture of bone and non-bone particles can provide a desirable combination of structural support with bone material having good compressive modulus properties, and therapeutic support with non-bone material that may easily be made to incorporate therapeutic substances in know manners.

Figure 37:
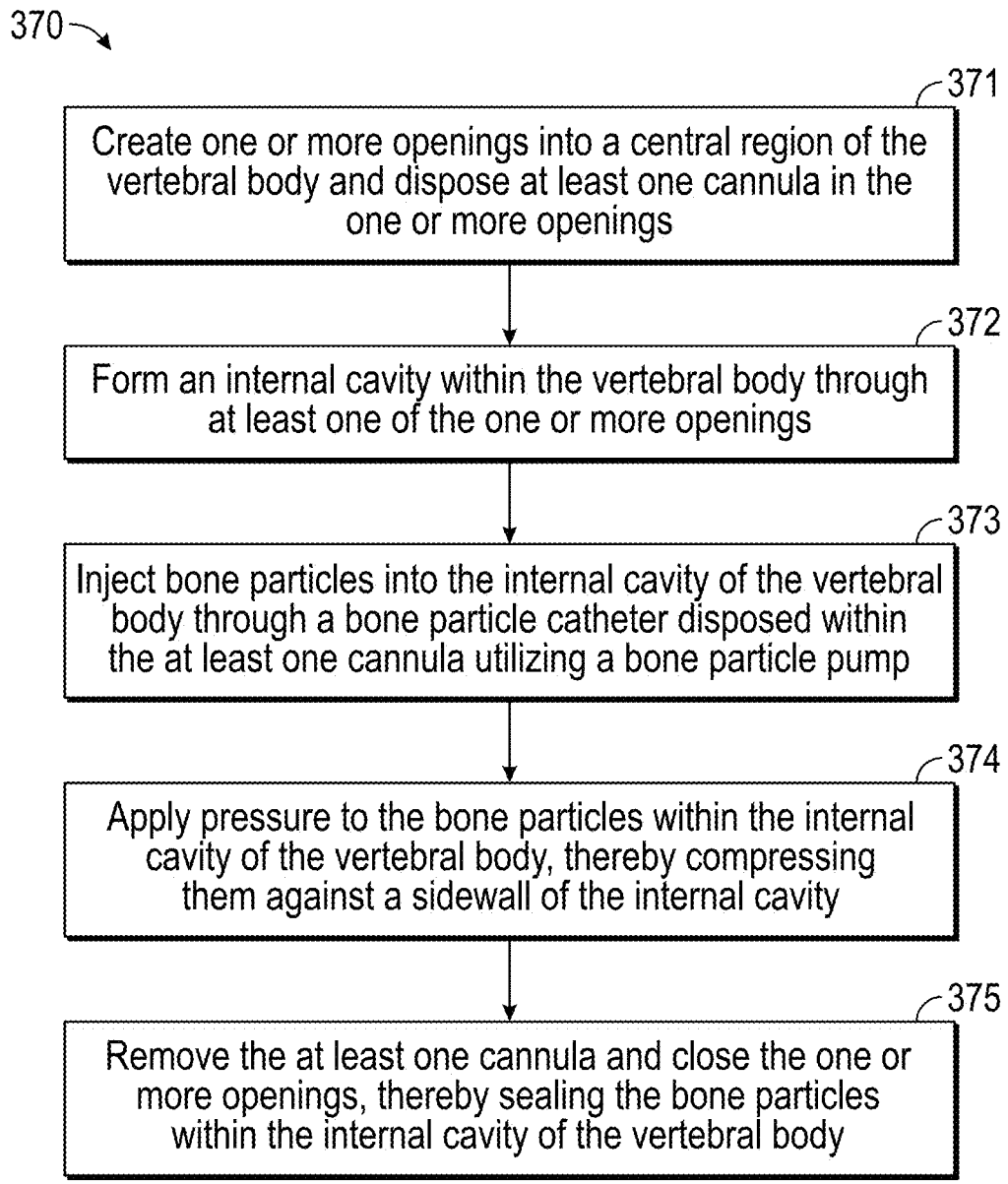
FIG. 37 illustrates a block diagram of a method that may be performed with any apparatus, system or kit described herein, in accordance with some embodiments.

FIG. 37 illustrates a block diagram 370 of a surgical method that can be performed with any bone particle injecting system, device and/or apparatus described in the present disclosure.

Block 371 includes creating one or more openings into a central region of the vertebral body and dispose at least one cannula in the one or more openings. For example, as previously described in connection with several figures throughout the disclosure, one or more openings can be created into a central region of vertebral body 25. At least one cannula 22, 52 can be disposed in those one or more openings. As previously described, creating the one or more openings can comprise one or more of drilling through a pedicle of vertebral body 25 utilizing a drill bit, and/or inserting one of a sharp end 242 of stylet 241 through the at least one cannula 22, 52 and through a pedicle of vertebral body 25, for example.

Block 372 includes forming an internal cavity within the vertebral body through at least one of the one or more openings. For example, as previously described in connection with at least FIGS. 2, 5, 6 and/or 27-29, internal cavity 26 can be formed within vertebral body 25 through the one or more openings. In some embodiments, forming internal cavity 26 within vertebral body 25 includes at least one of utilizing an aspirating device 64, 272, 275 to remove material from inside vertebral body 25 through an aspirating catheter 23, 53, 63 disposed within the one or more cannulas 22, 52, and utilizing an inflating device 283, 284 to inflate a kyphoplasty balloon 281, 282 inside vertebral body 25 through an inflating catheter 23, 53 disposed within the at least one cannula 22, 52.

In some embodiments, for example as previously described in connection with at least FIG. 6, forming internal cavity 26 within vertebral body 25 further comprises vibrating a distal end 23*b* of the aspirating catheter 23 inside vertebral body 25 to thereby agitate the material inside vertebral body 25 before removing that material from inside vertebral body 25.

Block 373 includes injecting bone particles into the internal cavity of the vertebral body through a bone particle catheter disposed within the at least one cannula utilizing a bone particle pump. In some embodiments, for example as previously described in connection with at least FIGS. 2, 5, 6 and 9A-14B, the bone particles can be injected in the form of a bone particle slurry comprising the bone particles and a liquid carrier. In some embodiments, the bone particle slurry comprises 20% to 85% bone particles by volume. In some embodiments, at least 90% of the bone particles have a size in the range of 50 to 1000 micrometers. In some embodiments, for example as previously described in connection with FIGS. 2, 5, 6 and 9A-14B, the bone particle pump can include a bone slurry pump 28, 58, 98, 108, 118, 128, 138, 148 and a pressure gauge configured to detect an amount of pressure being exerted by the bone slurry pump while injecting the bone particle slurry. In some such embodiments, the amount of pressure can be monitored while injecting the bone particle slurry. In some embodiments, a distal end 23*b* of the bone particle catheter 23 comprises at least one opening 29*a*, 29*b* disposed in a side of the catheter 23 such that at least some of the bone particles are injected into internal cavity 26 in a direction substantially perpendicular to a longitudinal extent of the catheter 23.

In some embodiments, a method according to FIG. 37 can additionally include mixing bone particles 201 with the liquid carrier to form the bone particle slurry utilizing an auger 92, 102, 112, 122, 132 disposed within the bone particle pump 98, 108, 118, 128, 138, for example as previously described in connection with at least FIGS. 9A-13B. In some such embodiments, bone particles 201 are disposed within a dry bone compartment 105 within bone particle pump 108, and the liquid carrier is disposed within a liquid compartment 104 different from the dry bone compartment before mixing bone particles 201 with the liquid carrier. In some embodiments, mixing the bone particles with the liquid carrier to form the bone particle slurry can include activating one of a handle 91, 101, 111 or a button 131 of the bone particle pump 98, 108, 118, 138 configured to turn the auger 92, 102, 112, 132, and driving a plunger 96, 106, 116, 136 configured to push the bone particles toward an outlet of the bone particle pump.

In some embodiments, the bone particles are injected in the form of a plurality of bone pellets 74. In some embodiments, for example as previously described in connection with at least FIG. 7B, the plurality of bone pellets 74 comprise substantially cylindrical bicortical dowels of cancellous bone having cortical endcaps. In some embodiments, for example as previously described in connection with at least FIG. 7C, the plurality of bone pellets 74a-74e are formed by injecting a rod 77 of bone, having a plurality of transverse cuts 75a-75e extending incompletely therethrough, into internal cavity 26 of vertebral body 25, thereby causing the rod 77 of bone to fragment into the plurality of bone pellets 74a-74e. In some embodiments, for example as previously described in connection with at least FIG. 7D, the plurality of bone pellets 74f comprise a plurality of compressed bone strips 79a-79c pressed into the form of the plurality of bone pellets 74f.

Block 374 includes applying pressure to the bone particles within the internal cavity of the vertebral body, thereby compressing them against a sidewall of the internal cavity. For example, as previously described in connection with at least FIGS. 2, 5, 6 and 9A-14B, the bone slurry itself can be pressurized, e.g., to increase the height of the vertebral body as the slurry is injected. In some embodiments, it can be advantageous to pressurize the bone slurry without a bag or other structure enclosing or confining the slurry that is being injected. As an additional or alternative example, as previously described in connection with at least FIGS. 34 and 35, applying pressure to the bone particles within the internal cavity of the vertebral body can include inflating kyphoplasty balloon(s) 281, 282 inside internal cavity 26, thereby crushing the plurality of bone pellets 74 against a wall of internal cavity 26.

Block 375 includes removing the at least one cannula and closing the one or more openings, thereby sealing the bone particles within the internal cavity of the vertebral body. For example, as previously described throughout this disclosure, a plug may be placed in the opening(s) of vertebral body 25 through which the one or more cannula(s) 22, 52 entered vertebral body 25. Such a plug can be made of a variety of materials including, but not limited to, stainless steel, titanium, cobalt chrome molybdenum, TLA, PGA, PMMA, methylcellulose, or cortical allograft bone.

In some embodiments, a method according to FIG. 37 can also include loading at least one barrel 84a-84c, 164a-164c of a bone particle cartridge 80, 160, with the bone particles 201, 74, loading the bone particle cartridge onto the bone particle pump 82, 160, and pushing a plunger 86, 211 of the bone particle pump down the at least one barrel, thereby injecting the bone particles into internal cavity 26 of vertebral body 25 through the bone particle catheter 23, 53 disposed within the at least one cannula 22, 52, for example, as previously described in connection with at least FIGS. 8A-8E and 15-36.

In some embodiments, a method according to FIG. 37 can also include loading at least a portion of bone particle cartridge 160 into a cartridge holder 150, fastening, over cartridge 160 and cartridge holder 150, filling cap 180 comprising beveled upper surface 182 that recesses toward a center of filling cap 180 and a hole 183 in the central bottom of beveled upper surface 182 that exposes the at least one barrel 164a-164c of cartridge 160, disposing bone particles 201 in the recess of beveled upper surface 182, and utilizing a tamp 211 to push bone particles 201 from the recess of beveled upper surface 182 through hole 183 and into the at least one barrel 164a-164c, for example as previously described in connection with FIGS. 15-23.

General Interpretive Principles for the Present Disclosure

Various aspects of the novel systems, apparatuses, and methods are described more fully hereinafter with reference to the accompanying drawings. The teachings disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the novel systems, apparatuses, and methods disclosed herein, whether implemented independently of or combined with any other aspect of the disclosure. For example, a system or an apparatus may be implemented, or a method may be practiced using any one or more of the aspects set forth herein. In addition, the scope of the disclosure is intended to cover such a system, apparatus or method which is practiced using other structure, functionality, or structure and functionality in addition to or other than the various aspects of the disclosure set forth herein. It should be understood that any aspect disclosed herein may be set forth in one or more elements of a claim. Although some benefits and advantages of the preferred aspects are mentioned, the scope of the disclosure is not intended to be limited to particular benefits, uses, or objectives. The detailed description and drawings are merely illustrative of the disclosure rather than limiting, the scope of the disclosure being defined by the appended claims and equivalents thereof.

With respect to the use of plural vs. singular terms herein, those having skill in the art can translate from the plural to the singular and/or from the singular to the plural as is appropriate to the context and/or application. The various singular/plural permutations may be expressly set forth herein for sake of clarity.

When describing an absolute value of a characteristic or property of a thing or act described herein, the terms "substantial," "substantially," "essentially," "approximately," and/or other terms or phrases of degree may be used without the specific recitation of a numerical range. When applied to a characteristic or property of a thing or act described herein, these terms refer to a range of the characteristic or property that is consistent with providing a desired function associated with that characteristic or property.

In those cases where a single numerical value is given for a characteristic or property, it is intended to be interpreted as at least covering deviations of that value within one significant digit of the numerical value given.

If a numerical value or range of numerical values is provided to define a characteristic or property of a thing or act described herein, whether or not the value or range is qualified with a term of degree, a specific method of measuring the characteristic or property may be defined herein as well. In the event no specific method of measuring the characteristic or property is defined herein, and there are different generally accepted methods of measurement for the characteristic or property, then the measurement method should be interpreted as the method of measurement that would most likely be adopted by one of ordinary skill in the art given the description and context of the characteristic or property. In the further event there is more than one method of measurement that is equally likely to be adopted by one of ordinary skill in the art to measure the characteristic or property, the value or range of values should be interpreted as being met regardless of which method of measurement is chosen.

It will be understood by those within the art that terms used herein, and especially in the appended claims (e.g., bodies of the appended claims) are intended as "open" terms unless specifically indicated otherwise (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

In those instances where a convention analogous to "at least one of A, B, and C" is used, such a construction would include systems that have A alone, B alone, C alone, A and B together without C, A and C together without B, B and C together without A, as well as A, B, and C together. It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include A without B, B without A, as well as A and B together."

Various modifications to the implementations described in this disclosure can be readily apparent to those skilled in the art, and generic principles defined herein can be applied to other implementations without departing from the spirit or scope of this disclosure. Thus, the disclosure is not intended to be limited to the implementations shown herein but is to be accorded the widest scope consistent with the claims, the principles and the novel features disclosed herein. The word "exemplary" is used exclusively herein to mean "serving as an example, instance, or illustration." Any implementation described herein as "exemplary" is not necessarily to be construed as preferred or advantageous over other implementations.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

What is claimed is:

1. A system for stabilizing a vertebral body, the system comprising:
    a pellet delivery apparatus comprising a plunger;
    a cartridge having a first end configured to be removably attached to the pellet delivery apparatus and a second end comprising an outlet, the cartridge comprising at least one elongated shaft having at least one barrel formed therein, wherein the at least one barrel contains pre-loaded solid pellets configured to stabilize the vertebral body, wherein the cartridge comprises a plurality of barrels;
    a kyphoplasty balloon;
    an inflating catheter; and
    an inflating device configured to inflate the kyphoplasty balloon inside the vertebral body through the inflating catheter, thereby crushing the plurality of pellets against a wall of the internal cavity;
    wherein the plunger is configured to push at least some of the pellets from the cartridge through the outlet and into an internal cavity in the central region of the vertebral body.

2. The system of claim 1, wherein the pellets comprise a plurality of bone pellets.

3. The system of claim 2, wherein the plurality of bone pellets comprise substantially cylindrical bicortical dowels of cancellous bone having cortical endcaps.

4. The system of claim 2, wherein the bone pellets are formed as a rod of bone having a plurality of transverse cuts extending incompletely therethrough, the rod configured to fragment into a plurality of separated bone pellets when injected forcefully into the internal cavity of the vertebral body.

5. The system of claim 2, wherein the plurality of bone pellets comprise a plurality of compressed bone strips pressed into the form of the plurality of bone pellets.

6. The system of claim 1, wherein the plunger is ratcheted.

7. The system of claim 6, wherein the ratchet is advanced with a trigger of the pellet delivery apparatus.

8. The system of claim 1, wherein the pellets comprise PMMA.

9. The system of claim 1, wherein the pellets comprise titanium.

10. The system of claim 9, wherein the pellets are spherical.

11. A system for stabilizing a vertebral body, the system comprising:
- a pellet delivery apparatus comprising a plunger;
- a cartridge having a first end configured to be removably attached to the pellet delivery apparatus and a second end comprising an outlet, the cartridge comprising at least one elongated shaft having at least one barrel formed therein, wherein the at least one barrel contains pre-loaded solid pellets configured to stabilize the vertebral body, wherein the cartridge comprises a plurality of barrels;
- a cartridge holder configured to hold the cartridge;
- a filling cap configured to be fastened over the cartridge and the cartridge holder, the filling cap comprising:
  - a beveled upper surface that recesses toward a center of the filling cap and that is configured to receive the pellets, and
  - a hole in the central bottom of beveled upper surface configured to expose the at least one barrel of the cartridge when the filling cap is fastened over the cartridge; and
- a tamp configured to push the pellets from the recess of the beveled upper surface through the hole and into the at least one barrel of the cartridge, wherein the plunger is configured to push at least some of the pellets from the cartridge through the outlet and into an internal cavity in the central region of the vertebral body.

* * * * *